US010656117B2

(12) United States Patent
Mayer et al.

(10) Patent No.: US 10,656,117 B2
(45) Date of Patent: *May 19, 2020

(54) NANOPORE-BASED DETERMINATION OF PROTEIN CHARGE, SHARP, VOLUME, ROTATIONAL DIFFUSION COEFFICIENT, AND DIPOLE MOMENT

(71) Applicant: THE REGENTS OF THE UNIVERSITY OF MICHIGAN, Ann Arbor, MI (US)

(72) Inventors: Michael Mayer, Ann Arbor, MI (US); Erik Yusko, Seattle, WA (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/436,591

(22) Filed: Jun. 10, 2019

(65) Prior Publication Data
US 2019/0323990 A1 Oct. 24, 2019

Related U.S. Application Data

(63) Continuation of application No. 15/416,522, filed on Jan. 26, 2017, now Pat. No. 10,317,361, which is a continuation of application No. 14/188,164, filed on Feb. 24, 2014, now Pat. No. 9,557,292.

(60) Provisional application No. 61/789,196, filed on Mar. 15, 2013, provisional application No. 61/768,795, filed on Feb. 25, 2013.

(51) Int. Cl.
G01N 27/447 (2006.01)
G01N 33/487 (2006.01)
C12Q 1/6869 (2018.01)

(52) U.S. Cl.
CPC ....... *G01N 27/4473* (2013.01); *C12Q 1/6869* (2013.01); *G01N 27/44791* (2013.01); *G01N 33/48721* (2013.01)

(58) Field of Classification Search
CPC ......... G01N 27/3278; G01N 33/48721; G01N 15/1209; G01N 2015/0038; C12Q 1/6869; C12Q 2565/631; B82Y 30/00
See application file for complete search history.

(56) References Cited

U.S. PATENT DOCUMENTS

| 2,656,508 | A | 10/1953 | Coulter |
| 7,521,225 | B2 | 4/2009 | Smirnov |
| 7,777,505 | B2 | 8/2010 | White et al. |
| 9,347,929 | B2 | 5/2016 | Mayer et al. |
| 9,557,292 | B2 | 1/2017 | Mayer et al. |
| 10,254,271 | B2 | 4/2019 | Mayer et al. |
| 10,317,361 | B2 | 6/2019 | Mayer et al. |
| 2006/0183112 | A1 | 8/2006 | Min et al. |
| 2007/0298511 | A1 | 12/2007 | Kang et al. |
| 2008/0254995 | A1 | 10/2008 | Kim et al. |
| 2008/0286750 | A1 | 11/2008 | Xu et al. |
| 2009/0184047 | A1 | 7/2009 | Thayumanavan et al. |
| 2010/0148126 | A1 | 6/2010 | Guan et al. |
| 2011/0159601 | A1 | 6/2011 | Golovchenko et al. |
| 2011/0177498 | A1 | 7/2011 | Clarke et al. |
| 2011/0250705 | A1 | 10/2011 | Polonsky et al. |
| 2012/0133354 | A1 | 5/2012 | Canas et al. |
| 2019/0234930 | A1 | 8/2019 | Mayer et al. |

FOREIGN PATENT DOCUMENTS

| WO | WO-2006137891 A2 | 12/2006 |
| WO | WO-2007127327 A2 | 11/2007 |
| WO | WO-2008102120 A1 | 8/2008 |
| WO | WO-2008102121 A1 | 8/2008 |
| WO | WO-2009020682 A2 | 2/2009 |
| WO | WO-2009077734 A2 | 6/2009 |
| WO | WO-2010004265 A1 | 1/2010 |
| WO | WO-2010004273 A1 | 1/2010 |
| WO | WO-2010086602 A1 | 8/2010 |
| WO | WO-2010086603 A1 | 8/2010 |
| WO | WO-2010086622 A1 | 8/2010 |
| WO | WO-2010122293 A1 | 10/2010 |
| WO | WO-2014074922 A1 | 5/2014 |

OTHER PUBLICATIONS

Yusko et al. Nature Nanotechnology, 2011, 6, 253-260 (Year: 2011).*
Ali et al., "Biosensing and Supramolecular Bioconjugation in Single Conical Polymer Nanochannels. Facile Incorporation of Biorecognition Elements into Nanoconfined Geometries." Journal of the American Chemical Society, vol. 130, No. 48, pp. 16351-16357 (2008).
Axelrod et al., "Mobility measurement by analysis of fluorescence photobleaching recovery kinetics." Biophysical Journal, vol. 16, No. 9, pp. 1055-1069 (1976).
Bayley et al., "Stochastic sensors inspired by biology." Nature, vol. 413, pp. 226-230 (2001).
Benner et al., "Sequence-specific detection of individual DNA polymerase complexes in real time using a nanopore." Nature Nanotechnology, vol. 2, No. 11, pp. 718-724 (2007).
Branton et al., "The potential and challenges of nanopore sequencing." Nature Biotechnology, vol. 26, No. 10, pp. 1146-1153 (2008).
Clarke et al., "Continuous base identification for single-molecule nanopore DNA sequencing." Nature Nanotechnology, vol. 4, pp. 265-270 (2009).
Cremer et al., "Formation and Spreading of Lipid Bilayers on Planar Glass Supports." The Journal of Physical Chemistry B, vol. 103, No. 13, pp. 2554-2559 (1999).
DeBlois et al., "Counting and Sizing of Submicron Particles by the Resistive Pulse Technique." The Review of Scientific Instruments, vol. 41, No. 7, pp. 909-915 (1970).

(Continued)

*Primary Examiner* — Gurpreet Kaur
(74) *Attorney, Agent, or Firm* — Harness, Dickey & Pierce, P.L.C.

(57) ABSTRACT

Physical parameters of macromolecules are determined by measuring electrical current I over time for translocation events as the macromolecules in solution move between two liquid compartments that are separated by and fluidically coupled through a synthetic nanopore. Values of charge, volume, shape, rotational diffusion coefficient, and dipole moment are derived from the measurements.

20 Claims, 23 Drawing Sheets

(56) References Cited

OTHER PUBLICATIONS

Dekker, "Solid-state nanopores." Nature Nanotechnology, vol. 2, pp. 209-215 (2007).
Erickson, "Size and Shape of Protein Molecules at the Nanometer Level Determined by Sedimentation, Gel Filtration, and Electron Microscopy." Biological Procedures Online, vol. 11, No. 1, pp. 32-51 (2009).
Fologea et al., "Electrical characterization of protein molecules by a solid-state nanopore." Applied Physics Letters, vol. 91, No. 5, pp. 053901-1-053901-3 (2007).
Gennis, "Biomembranes: Molecular Structure and Function." Springer, New York, NY, pp. 60-65 (1989).
Golibersuch, "Observation of Aspherical Particle Rotation in Poiseuille Flow via the Resistance Pulse Technique: I. Application to Human Erythrocytes." Biophysical Journal, vol. 13, No. 3, pp. 265-280 (1973).
Griffiths, "The realm of the nanopore: Interest in nanoscale research has skyrocketed, and the humble pore has become a king." Analytical Chemistry, vol. 80, No. 1, pp. 23-27 (2008).
Grover et al., "Electrical Sizing of Particles in Suspensions: I. Theory." Biophysical Journal, vol. 9, No. 11, pp. 1398-1414 (1969).
Grover et al., "Electrical Sizing of Particles in Suspensions: II. Experiments with Rigid Spheres." Biophysical Journal, vol. 9, No. 11, pp. 1415-1425 (1969).
Guo et al., "Charge substitution shows that repulsive electrostatic interactions impede the oligomerization of Alzheimer amyloid peptides." FEBS Letters, vol. 579, No. 17, pp. 3574-3578 (2005).
Hall et al., "Electrophoretic Force on a Protein-Coated DNA Molecule in a Solid-State Nanopore." Nano Letters, vol. 9, No. 12, pp. 4441-4445 (2009).
Han et al., "Label-Free Detection of Single Protein Molecules and Protein-Protein Interactions Using Synthetic Nanopores." Analytical Chemistry, vol. 80, No. 12, pp. 4651-4658 (2008).
Han et al., "Sensing protein molecules using nanofabricated pores." Applied Physics Letters, vol. 88, pp. 093901-1-093901-3 (2006).
Hansen et al., "Development of an automation technique for the establishment of functional lipid bilayer arrays." Journal of Micromechanics and Microengineering, vol. 19, No. 2, pp. 025014-1025014-11 (2009).
Hernández-Ainsa et al., "Lipid-coated nanocapillaries for DNA sensing." Analyst, vol. 138, pp. 104-106 (2013).
Hille, "Ionic Channels in Excitable Membranes." Biophysical Journal, vol. 22, No. 2, pp. 283-294 (1978).
Howorka et al., "Nanopore analytics: sensing of single molecules." Chemical Society Reviews, vol. 38, No. 8, pp. 2360-2384 (2009).
Hurley, "Sizing Particles with a Coulter Counter." Biophysical Journal, vol. 10, No. 1, pp. 74-79 (1970).
Ito et al., "Simultaneous Determination of the Size and Surface Charge of Individual Nanoparticles Using a Carbon Nanotube-Based Coulter Counter." Analytical Chemistry, vol. 75, No. 10, pp. 2399-2406 (2003).
Jachimska et al, "Characterization of Globular Protein Solutions by Dynamic Light Scattering, Electrophoretic Mobility, and Viscosity Measurements." Langmuir, vol. 24, No. 13, pp. 6866-6872 (2008).
Jan et al., "Preparation and characterization of toxic Aβ aggregates for structural and functional studies in Alzheimer's disease research." Nature Protocols, vol. 5, No. 6, pp. 1186-1209 (2010).
Janssen et al., "Electromagnetic Torque Tweezers: A Versatile Approach for Measurement of Single-Molecule Twist and Torque." Nano Letters, vol. 12, No. 7, pp. 3634-3639 (2012).
Kasianowicz et al., "Characterization of individual polynucleotide molecules using a membrane channel." Proceedings of the National Academy of Sciences, vol. 93, No. 24, pp. 13770-13773 (1996).
Kellermayer et al., "Stepwise dynamics of epitaxially growing single amyloid fibrils." Proceedings of the National Academy of Sciences, vol. 105, No. 1, pp. 141-144 (2008).
Li et al., "Ion-beam sculpting at nanometre length scales." Nature, vol. 412, pp. 166-169 (2001).
Li et al., "The distribution of DNA translocation times in solid-state nanopores." Journal of Physics: Condensed Matter, vol. 22, No. 45, pp. 454129-1-454129-8 (2010).
Macrae et al., "A Semi-Synthetic Ion Channel Platform for Detection of Phosphatase and Protease Activity." ACS Nano, vol. 3, No. 11, pp. 3567-3580 (2009).
Majd et al., "Gramicidin Pores Report the Activity of Membrane-Active Enzymes." Journal of the American Chemical Society, vol. 131, No. 44, pp. 16119-16126 (2009).
Martin et al., "Learning Nature's Way: Biosensing with Synthetic Nanopores." Science, vol. 317, No. 5836, pp. 331-332 (2007).
Mathé et al., "Orientation discrimination of single-stranded DNA inside the α-hemolysin membrane channel." Proceedings of the National Academy of Sciences, vol. 102, No. 35, pp. 12377-12382 (2005).
Movileanu et al., "Detecting protein analytes that modulate transmembrane movement of a polymer chain within a single protein pore." Nature Biotechnology, vol. 18, No. 10, pp. 1091-1095 (2000).
Movileanu, "Interrogating single proteins through nanopores: challenges and opportunities." Trends in Biotechnology, vol. 27, No. 6, pp. 333-341 (2009).
Nilsson et al., "Localized functionalization of single nanopores." Advanced Materials, vol. 18, No. 4, pp. 427-431 (2006).
Oukhaled et al., "Unfolding of Proteins and Long Transient Conformations Detected by Single Nanopore Recording." Physical Review Letters, vol. 98, No. 15, pp. 158101-1-158101-4 (2007).
Pandey et al., "Proteomics to study genes and genomes." Nature, vol. 405, No. 6788, pp. 837-846 (2000).
Pedone et al., "Data Analysis of Translocation Events in Nanopore Experiments." Analytical Chemistry, vol. 81, No. 23, pp. 9689-9694 (2009).
Prangkio, "Investigation of Cytotoxicity and Ion Flux Induced by Various Aggregation States of Amyloid-Beta Peptides." Ph.D. Dissertation, The University of Michigan (2011).
Qin et al., "Effects of particle's off-axis position, shape, orientation and entry position on resistance changes of micro Coulter counting devices." Measurement Science and Technology, vol. 22, No. 4, pp. 045804-1-045804-10 (2011).
Raillon et al., "Nanopore Detection of Single Molecule RNAP-DNA Transcription Complex." Nano Letters, vol. 12, No. 3, pp. 1157-1164 (2012).
Reimhult et al., "Intact Vesicle Adsorption and Supported Biomembrane Formation from Vesicles in Solution: Influence of Surface Chemistry, Vesicle Size, Temperature, and Osmotic Pressure." Langmuir, vol. 19, No. 5, pp. 1681-1691 (2003).
Robertson et al., "Single-molecule mass spectrometry in solution using a solitary nanopore." Proceedings of the National Academy of Sciences, vol. 104, No. 20, pp. 8207-8211 (2007).
Rosenstein et al., "Integrated nanopore sensing platform with sub-microsecond temporal resolution." Nature Methods, vol. 9, No. 5, pp. 487-492 (2012).
Rotem et al., "Protein Detection by Nanopores Equipped with Aptamers." Journal of the American Chemical Society, vol. 134, No. 5, pp. 2781-2787 (2012).
Sackmann, "Supported Membranes: Scientific and Practical Applications." Science, vol. 271, No. 5245, pp. 43-48 (1996).
Schar et al., "Sulfates of ethoxylated tridecyl alcohol in dishwashing formulations." Journal of the American Oil Chemists' Society, vol. 37, No. 9, pp. 427-430 (1960).
Sexton et al., "An Adsorption-Based Model for Pulse Duration in Resistive-Pulse Protein Sensing." Journal of the American Chemical Society, vol. 132, No. 19, pp. 6755-6763 (2010).
Sexton et al., "Resistive-Pulse Studies of Proteins and Protein/Antibody Complexes Using a Conical Nanotube Sensor." Journal of the American Chemical Society, vol. 129, No. 43, pp. 13144-13152 (2007).
Skinner et al., "Distinguishing Single- and Double-Stranded Nucleic Acid Molecules Using Solid-State Nanopores." Nano Letters, vol. 9, No. 8, pp. 2953-2960 (2009).
Solomentsev et al., "Electrophoretic transport of spheroidal colloids in nonhomogeneous electric fields." Industrial & Engineering Chemistry Research, vol. 34, No. 10, pp. 3231-3238 (1995).

(56) References Cited

OTHER PUBLICATIONS

Soni et al., "Detection of Nucleosomal Substructures using Solid-State Nanopores." Nano Letters, vol. 12, No. 6, pp. 3180-3186 (2012).

Starr et al., "Formation and Characterization of Planar Phospholipid Bilayers Supported on $TiO_2$ and $SrTiO_3$ Single Crystals." Langmuir, vol. 16, No. 26, pp. 10301-10308 (2000).

Studer, "Investigations on planar lipid bilayers in nano-pores to study the function of membrane proteins." Doctoral Thesis No. 18473, ETH Zürich (2009).

Talaga et al., "Single-Molecule Protein Unfolding in Solid State Nanopores." Journal of the American Chemical Society, vol. 131, No. 26, pp. 9287-9297 (2009).

Timbs et al., "Slow rotational mobilities of antibodies and lipids associated with substrate-supported phospholipid monolayers as measured by polarized fluorescence photobleaching recovery." Biophysical Journal, vol. 58, No. 2, pp. 413-428 (1990).

Uram et al., "Label-Free Affinity Assays by Rapid Detection of Immune Complexes in Submicrometer Pores." Angewandte Chemie International Edition, vol. 45, No. 14, pp. 2281-2285 (2006).

Uram et al., "Noise and Bandwidth of Current Recordings from Submicrometer Pores and Nanopores." ACS Nano, vol. 2, No. 5, pp. 857-872 (2008).

Uram et al., "Submicrometer Pore-Based Characterization and Quantification of Antibody-Virus Interactions." Small, vol. 2, No. 8-9, pp. 967-972 (2006).

Venkatesan et al., "Lipid bilayer coated Al2O3 nanopore sensors: towards a hybrid biological solid-state nanopore." Biomedical Microdevices, vol. 13, No. 4, pp. 671-682 (2011).

Wang et al., "Nanopore Analysis of β-Amyloid Peptide Aggregation Transition Induced by Small Molecules." Analytical Chemistry, vol. 83, No. 5, pp. 1746-1752 (2011).

Wei et al., "Stochastic sensing of proteins with receptor-modified solid-state nanopores." Nature Nanotechnology, vol. 7, No. 4, pp. 257-263 (2012).

Woodside et al., "Direct Measurement of the Full, Sequence-Dependent Folding Landscape of a Nucleic Acid." Science, vol. 314, No. 5801, pp. 1001-1004 (2006).

Yusko et al., "Lipid Bilayers in Nanopores to Vary their Diameter, Characterize Amyloid-β Aggregates and Monitor the Activity of Membrane-Active Enzymes." Biophysical Journal, vol. 98, No. 2, p. 598a (2010).

Yusko et al., "Nanopore Recordings to Quantify Activity-Related Properties of Proteins." Nanopores: Sensing and Fundamental Biological Interactions, Springer Science + Business Media, LLC, pp. 203-225 (2011).

Yusko et al., "Single-Particle Characterization of Aβ Oligomers in Solution." ACS Nano, vol. 6, No. 7, pp. 5909-5919 (2012).

Zhao et al., "Real-Time Monitoring of Peptide Cleavage Using a Nanopore Probe." Journal of the American Chemical Society, vol. 131, No. 18, pp. 6324-6325 (2009).

\* cited by examiner

NANOPORE-BASED DETERMINATION OF PROTEIN CHARGE, SHARP, VOLUME, ROTATIONAL DIFFUSION COEFFICIENT, AND DIPOLE MOMENT

CROSS-REFERENCE TO RELATED APPLICATIONS

This application is a continuation of U.S. application Ser. No. 15/416,522, filed on Jan. 26, 2017, which is a continuation of U.S. application Ser. No. 14/188,164, filed on Feb. 24, 2014, now U.S. Pat. No. 9,557,292, issued on Jan. 31, 2017, which claims the benefit of U.S. Provisional Application No. 61/789,196, filed on Mar. 15, 2013, and U.S. Provisional Application No. 61/768,795, filed on Feb. 25, 2013. The entire disclosures of the above applications are incorporated herein by reference.

GOVERNMENT SUPPORT

This invention was made with government support under GM081705 awarded by the National Institutes of Health. The government has certain rights in the invention.

INTRODUCTION

Proteins orchestrate cell behavior, serve as functional biomarkers, and are the targets of almost all drugs; consequently, methods for rapid analysis of proteins are necessary to reduce health care costs and continue the advancement of personalized medicine[1]. Arguably, the best techniques for characterizing proteins (i.e. two-dimensional polyacrylamide gel electrophoresis and mass spectroscopy) are inefficient and require biochemical steps that modify, denature, or fragment proteins[1]. Few techniques characterize proteins in their native environment. Here, we describe the use of electrolyte-filled nanopores for determining the shape and volume of single native proteins in situ; for non-spherical proteins, we describe methods for determining their rotational diffusion coefficients and dipole moments while in the nanopore.

Established methods for measuring the shape and rotational diffusion coefficients of native proteins in solution include depolarized dynamic light scattering[2], sedimentation by ultracentrifugation[3], small-angle X-ray scattering[4], and neutron scattering after modification of the proteins with deuterium[5]. Since for many proteins obtaining a complete crystal structure is improbable, protein structures are often constructed using complementary data from several techniques (e.g. electron microscopy, small-angle X-ray scattering, and NMR). Consequently, additional technologies for determining the general shape of proteins quickly and in aqueous solution would facilitate determining the structures of many proteins.

Electrolyte-filled nanopores through an insulating membrane are an emerging technology for characterizing macromolecules in their native environment[6-29]. These single-molecule experiments involve measuring the electric field-induced flow of ions through a single nanopore and the changes in this current (i.e. resistive pulses) when single macromolecules pass through the nanopore. Measuring the magnitude and duration of these transient changes in current ($\Delta I$ and $t_d$) during the translocation of thousands of single proteins enables construction of distributions that can reveal dynamic heterogeneities in size[12,20,26,27,29-33], conformation[14,22,23,34], and activity in situ[16,18,24,35-37].

Recently, Fologea et al. translocated nodular Fibrinogen proteins through electrolyte-filled nanopores and observed skewed distributions of $\Delta I$ values, which the authors hypothesized were due to the shape of the protein[13]. We also recently observed broad distributions of $\Delta I$ values that appeared to be bimodal during the translocation of $IgG_1$ antibodies through bilayer-coated nanopores[24]. We hypothesized that this unexpected result was due to the shape of IgG proteins, and we re-introduced a shape and orientation-dependent electrical shape factor, $\gamma^{24}$, that was first described in the 1960's during micropore-based resistive-pulse sensing experiments to characterize spheroid-shaped blood cells and viruses[38-41]. Raillon et al. and Soni et al. have since used the crystal structures of non-spherical proteins to estimate values for the electrical shape factor in order to analyze data obtained during the translocation of non-spherical proteins through nanopores. Interestingly, Raillon et al. also observed what appeared to be bimodal distributions of $\Delta I$ values due to the translocation of a non-spherical RNA polymerase[30]. Despite these first reports, quantitative information about the molecular shape and orientation of a protein has never been obtained from distributions of $\Delta I$ values. Furthermore, single-molecule methods capable of resolving the shape and volume of single, unlabeled proteins in aqueous environments have yet to be reported.

The use of nanopores with fluid walls to facilitate electronic measurements on individual proteins and other biomolecules is described in U.S. Ser. No. 13/400,472, filed Feb. 20, 2012, the contents of which is herein incorporated by reference.

ABSTRACT

In non-limiting fashion, we use bilayer-coated nanopores[24,26,42] to sense proteins exemplified streptavidin, anti-biotin immunoglobulin $G_1$, GPI-anchored acetylcholinesterase, anti-biotin Fab fragment, β-phycoerythrin, glucose-6-phosphate dehydrogenase, L-lactate dehydrogenase, bovine serum albumin, α-amylase, and butyrylcholine esterase and quantitatively analyze the resulting distributions of $\Delta I$ values in order to determine each protein's volume and shape. We demonstrate that the distributions of $\Delta I$ values as well as the time-dependent $\Delta I$ signals during the translocation of single proteins are bimodal for non-spherical proteins. We provide an explanation for this non-intuitive result and show, for the first time, that the time-dependent $\Delta I$ signals of non-spherical proteins can be used to determine the rotational diffusion coefficient and dipole moment of the proteins in the nanopore. Here, we demonstrate the use of lipid-bilayer coated nanopores for determining the shape and volume of single, spherical and non-spherical proteins that are anchored to mobile lipids in the coating. This work shows that individual resistive-pulses can also be used to determine the rotational diffusion coefficient and dipole moment of non-spherical proteins while in the nanopore. This approach extends the power of nanopores for characterizing proteins by adding the parameters of shape, volume, rotational diffusion coefficient, and dipole moment of non-spherical proteins to those that can already be determined in a single experiment such as the volume of spherical proteins, charge, and affinity for a ligand.

DRAWINGS

The drawings described herein are for illustrative purposes only of selected embodiments and not all possible implementations, and are not intended to limit the scope of the present disclosure.

FIG. 1 shows how current recordings through nanopores reveal the shape of single proteins as they translocate through the pore. (A) Experimental setup to measure resistive pulses from the translocation of individual proteins. (B) Top and side views of a nanopore illustrating the two extreme orientations of an ellipsoidal protein that is anchored to a fluid lipid coating on the pore wall. A crosswise orientation disturbs the field lines inside the pore more than a lengthwise orientation. (C) Three different strategies of anchoring proteins to the lipid coating were used to slow down translocation such that rotational diffusion of the proteins could be resolved in time. A lipid anchor with a biotin group selectively captured anti-biotin antibodies and Fab fragments, an intrinsic GPI anchor captured acetylcholinesterase, and a bi-functional, amine-reactive crosslinker provided a general strategy to attach proteins of interest covalently to ethanolamine lipids in the bilayer coating. All proteins analyzed in this work were tethered with a phospholipid anchor to the bilayer by one of these three strategies. These tethers were sufficiently long (≥1.5 nm in their extended conformation) and flexible (≥12 σ-bonds) and nanopore diameters were at least twice the volume-equivalent spherical diameter of the examined proteins, such that the proteins were able to rotate and sample all possible orientations. (D) Comparison of the shape of ten proteins as determined by analysis of resistive pulses (ellipsoids) with crystal structures from the protein data bank (streptavidin: 3RY1, anti-biotin immunoglobulin $G_1$: 1HZH, GPI-anchored acetylcholinesterase: 3LII, anti-biotin Fab fragment: 1F8T, β-phycoerythrin: 3V57, glucose-6-phosphate dehydrogenase: 4EM5, L-lactate dehydrogenase: 2ZQY, bovine serum albumin: 3V03, α-amylase: 1BLI, and butyrylcholine esterase: 1P01).

FIG. 2 shows current traces showing resistive pulses due to the translocation of monoclonal anti-biotin $IgG_1$ antibodies (a-c) through three different bilayer-coated nanopores and the resulting distributions of the maximum $\Delta I$ values (d-f). The volumes of the three nanopores were different resulting in different $\Delta I$ values in each pore. Stars (*) indicate the three pulses shown enlarged above the 5 s current traces. (d-f) Histograms of maximum $\Delta I$ values show empirical distributions of $\Delta I$ values, $P(\Delta I)$. Solid curves show the solution of the convolution model, $p(\Delta I)$, after a non-linear least squares fitting procedure, and dashed curves show the estimated distribution of $\Delta I$ values due to the distribution of shape factors, $p(\Delta I_\gamma)$. Dimensions of all nanopores are shown in Supplementary Section S11, and Supplementary Section S8 shows the values for all fitting parameters.

FIG. 3 shows current traces showing resistive pulses due to the translocation of streptavidin (a), Fab fragments (b), and GPI-AchE (c) and histograms of the maximum $\Delta I$ values determined during the translocation of streptavidin (d), Fab fragments (e), and GPI-AchE (f). d inset, Empirical cumulative distribution (black) fit with a Normal cumulative distribution function (CDF) (white). The derivative of the CDF shows the probability density function (PDF) and is plotted with the histogram in d. e-f, Solid curves show the solution of the convolution model, $p(\Delta I)$, after a non-linear least squares fitting procedure, and dashed curves show the estimated distribution of $\Delta I$ values due to the distribution of shape factors, $p(\Delta I_\gamma)$. Stars (*) indicate the three pulses shown enlarged above the 5 s current traces. Supplementary Section S8 lists the values of all fitting parameters.

FIG. 4 shows possible values of shape factors and their probability distribution. A, Shape factor as a function of m when θ=0 (solid curves) and when θ=π/2 (dashed curves) for prolates (m>10°) and oblates (m<10°). For a sphere, m equals 1, and the shape factor is 1.5. B, Shape factor as a function of θ for prolates and oblates (top line at zero radians) with a defined m. For a sphere, m equals 1, and the shape factor is 1.5. C, Probability distribution of shape factors, p(γ), predicted by Golibersuch (solid curve) and for proteins with a dipole moment pointed parallel to the longest axis of the protein (dashed curves). For the different magnitudes of the dipole moment, the energy difference between θ=0 and θ=π/2 is listed when the electric field equals 2E6 V $m^{-1}$. Supplementary Section S7 describes the electrical shape factor in detail.

FIG. 5 shows resistive pulses due to the translocation of $IgG_1$ antibodies and histograms of intra-event $\Delta I$ values. Experiments were performed in three different nanopores as in FIG. 2 (data from pores 1-3 are shown from top to bottom), and the dotted lines indicate the values of $\Delta I_{min}$ and $\Delta I_{max}$ expected from fitting the convolution model to the distributions in FIG. 2d-f. The current signal between the small dots on the left curves was considered the intra event-$\Delta I$ signal. On the right, the solid curves show the solution of the convolution model, $p(\Delta I)$, after a non-linear least squares fitting procedure, and dashed curves show the estimated distribution of $\Delta I$ values due to the distribution of shape factors, $p(\Delta I_\gamma)$.

FIG. 6 shows the shape, dipole moment, and rotational diffusion coefficient obtained from current modulations within individual resistive pulses from the translocation of a single protein. (A) Resistive pulse from the translocation of a single $IgG_1$ molecule. Dots mark the beginning and end of the resistive pulse as identified by an automated algorithm. (B) Distribution of all current values within this one resistive pulse. The solid curve shows the solution of the convolution model, $p(\Delta I)$, after a non-linear least squares fitting procedure, and the dashed curve shows the estimated distribution of $\Delta I$ values due to the distribution of shape factors, $p(\Delta I_\gamma)$. (C) Mean-squared-angular displacement curve (solid trace) and the initial slope (dashed line). The inset shows the transformation of intra-event $\Delta I(t)$ to θ(t). (D) Comparison of the shape of proteins as determined by analysis of individual resistive pulses with crystal structures (ellipsoids show the median values of m and volume from single event analyses of each protein for the complete distribution of single event analyses). (E) The most frequently observed dipole moments of BSA, Fab, GPI-AChE, $IgG_1$, and BChE agree well with expected reference values of their dipole moments. For the other five proteins, the number of long translocation events (≥0.4 ms) was too small for representative determination of the most probable dipole moment. (F) The most frequently observed rotational diffusion coefficients of $IgG_1$, GPI-AChE, Fab, and BChE agree well with the expected reference values. The signal-to-noise ratio for the other six proteins was too small to determine accurate values of $D_r$.

FIG. 7 illustrates an example of event detection. A moving average of current(time) or I(t) establishes a baseline. The threshold for event detection is the baseline signal minus 5 times the standard deviation of the I(t) signal. Translocation time, $t_d$, is calculated by determining the width of the peak at half of its maximum amplitude. The region circled is the part of the signal considered to be $\Delta I(t)$ signal. It is the region that is between the first and last local minima in the I(t) during an event (designated by the two dots at the baseline.

FIG. 8 is a graphic of a test for normal distribution.

FIG. 9 shows an example convolution of the probability distribution of $\Delta I$ values one expects due to the distribution of shape factors, $p(\Delta I_\gamma)$ (equation (S13)), and the error in determining individual $\Delta I$ values, $p(\Delta I_o)$ (a Normal distribution function). The solution to the convolution is the probability distribution of $\Delta I$ values one expects to observe, $p(\Delta I)$. During the fitting procedure, $p(\Delta I)$ is compared to the empirical distribution of $\Delta I$ values, $P(\Delta I)$, and the Levenberg-Marquardt non-linear least squares fitting algorithm in OriginPro 8 software generates new values for the fitting parameters $\Delta I_{min}$, $\Delta I_{max}$, AU, and σ, thereby creating new iterations of $p(\Delta I_\gamma)$ and $p(\Delta I_o)$. This processes repeats and in all cases the fits converged after approximately 100 to 200 iterations.

FIG. 10 demonstrates fitting experimental parameters.

FIG. 11 shows solutions for the parameter m.

FIG. 12 presents a graph of orientation θ(t).

Figure 15:
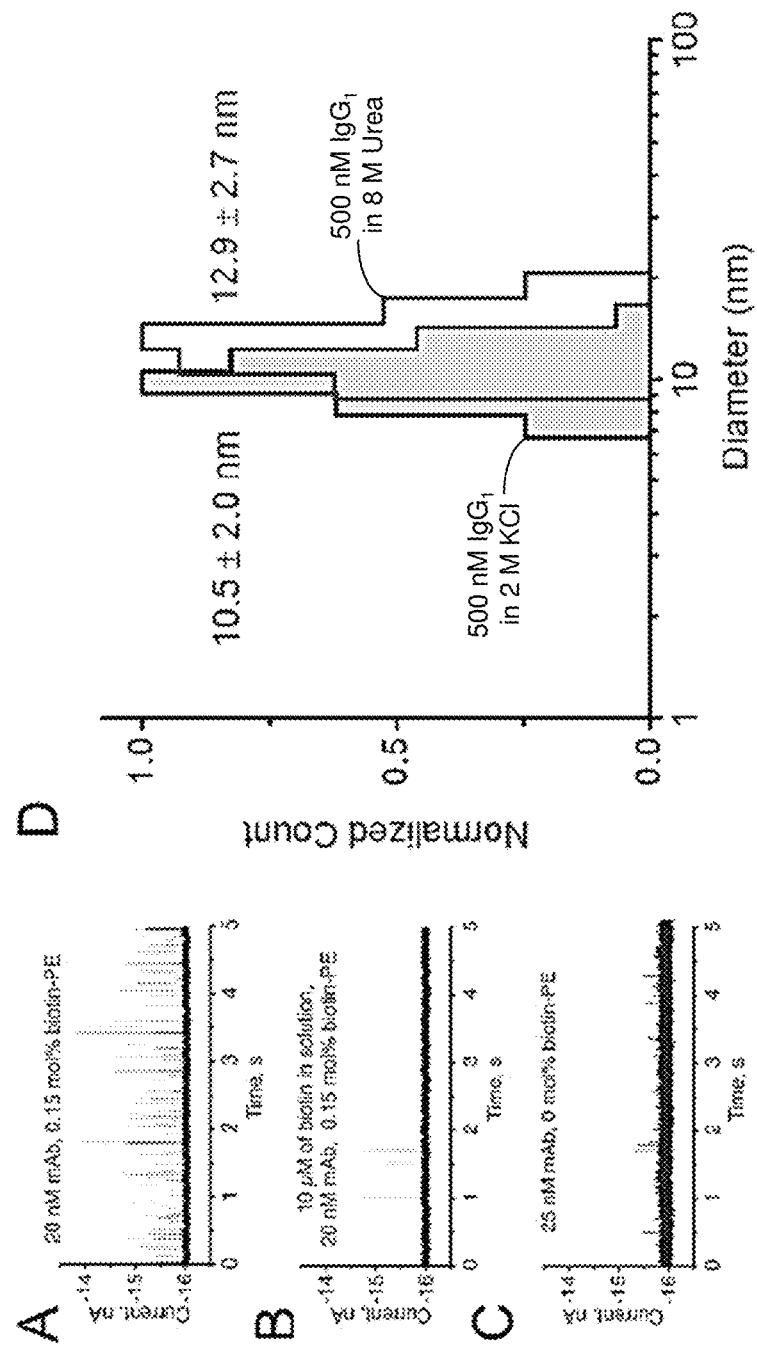

FIG. 15 shows detection of monoclonal anti-biotin $IgG_1$ antibody with a bilayer-coated nanopore and dynamic light scattering experiments. A) Current versus time trace showing resistive pulses due to translocation of $IgG_1$ antibodies that were bound to biotin-PE lipids in the bilayer coating. Resistive pulses occurred at a frequency of 34 $s^{-1}$. B) Current versus time trace recorded after the addition of excess biotin (10 μM) to the solution and containing a reduced frequency of resistive pulses (1.3 $s^{-1}$). C) Current versus time trace recorded using the same nanopore as A and B but with a bilayer coating that did not contain biotin-PE lipids. Resistive-pulses occurred at a frequency of 2 $s^{-1}$. The experiments were performed using nanopore[2] (FIG. S11). D) Hydrodynamic diameter of $IgG_1$ antibodies determined from dynamic light scattering experiments. $IgG_1$ antibodies were at a concentration of 500 nM in aqueous solutions identical to the recording electrolyte (2 M KCl and 10 mM HEPES at pH=7.4) during the dynamic light scattering experiment. Where indicated, 8 M of urea was added to the solution in order to denature all proteins. The dynamic light scattering results are the combination of 5 runs, each 60 s in duration. Results show the intensity-weighted calculation for the hydrodynamic diameter. The instrument was a Brookhaven 90Plus Particle Sizer and used a 658 nm laser at an angle of 90° to the detector. The absence of a second peak indicates that $IgG_1$ antibodies did not form a significant number of dimers in 2 M KCl even at concentrations 500 fold greater than in the resistive-pulse sensing experiments.

Figure 16:
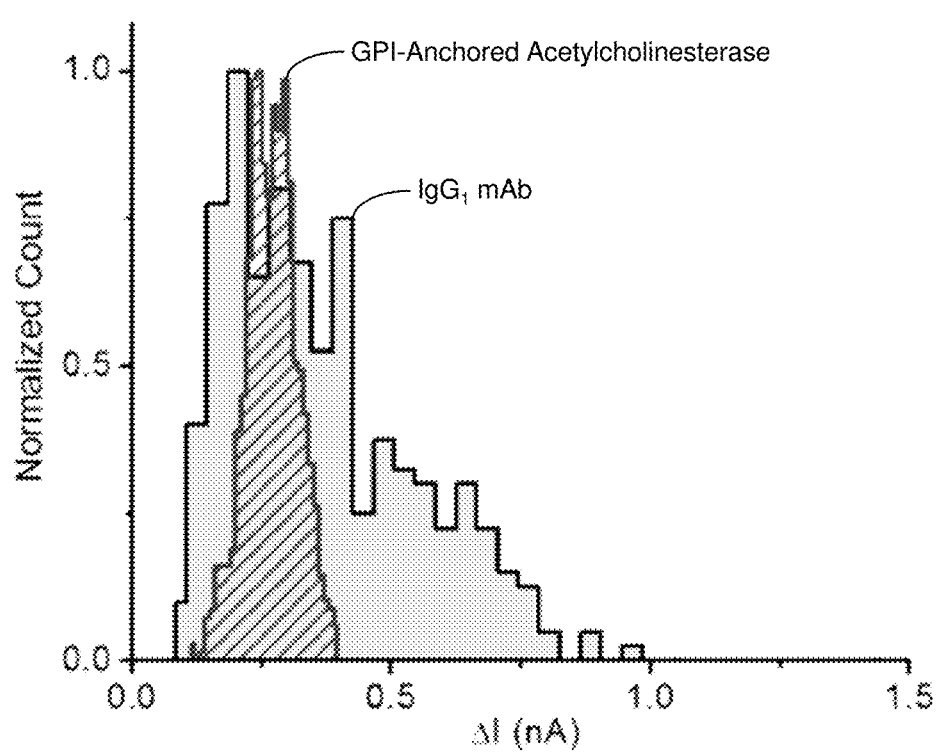

FIG. 16 shows histograms of the $\Delta I$ values due to the translocation of the $IgG_1$ antibody (150 kDa) and GPI-anchored acetylcholinesterase (160 kDa) through the same nanopore.

Figure 17:
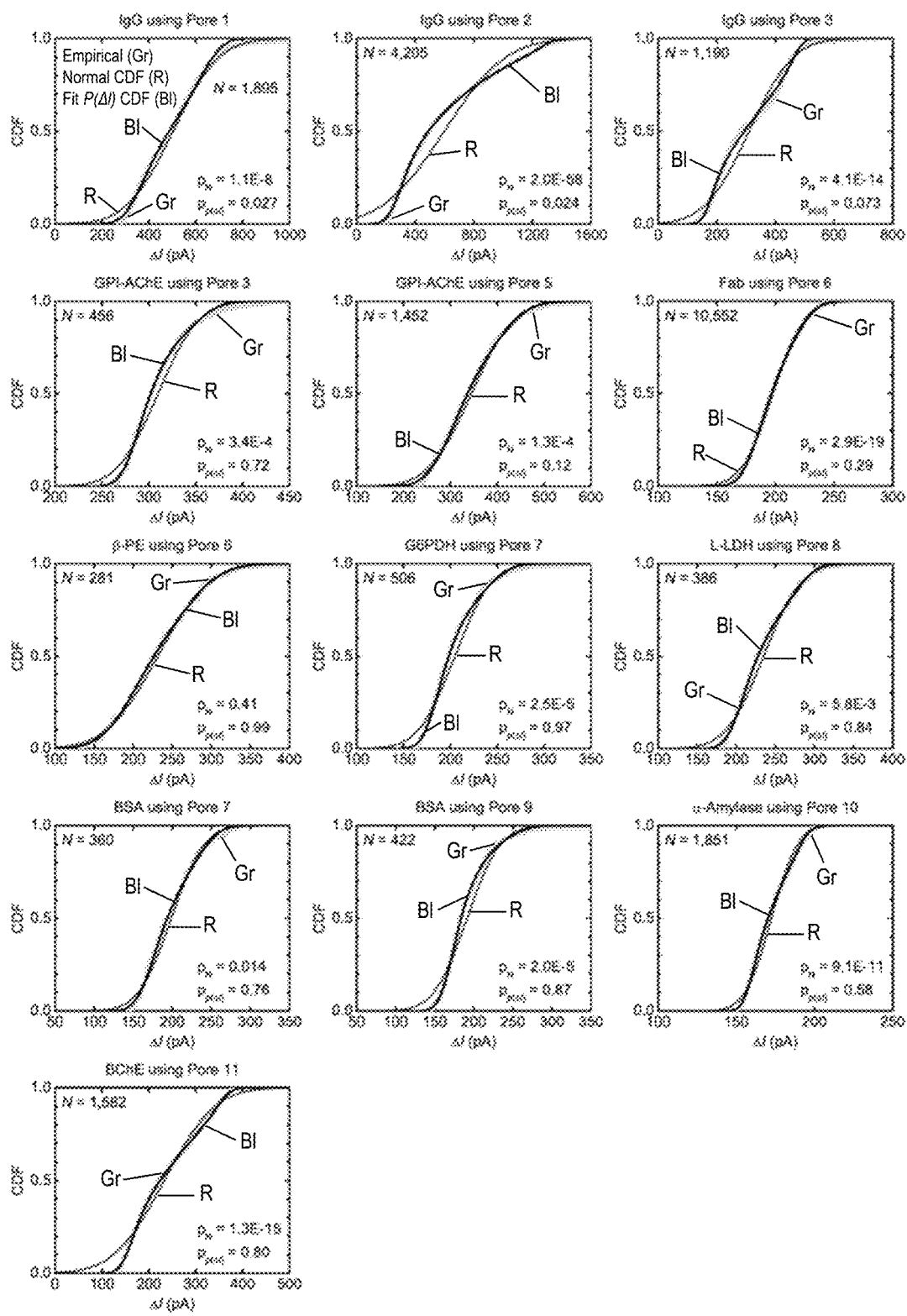

FIG. 17 shows empirical cumulative distributions (grey curves) of $\Delta I$ values due to the translocation of non-spherical proteins compared to a best-fit Normal distribution (thicker curves) and the solution the convolution model, $p(\Delta I)$ (thinner curves).

Figure 18:
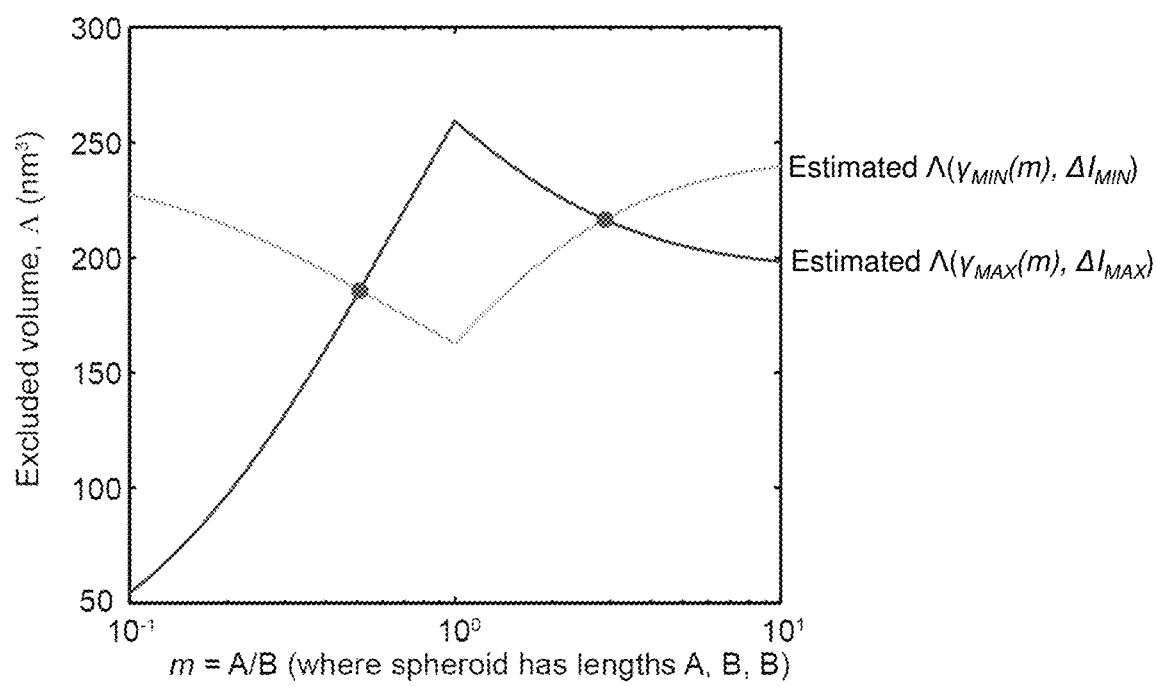

FIG. 18 shows estimating the excluded volume as a function of m using $\Delta I_{min}$ and $\Delta I_{max}$ values illustrates that there are two solutions to equations (S14) and (S15) for prolate shaped proteins.

Figure 19:
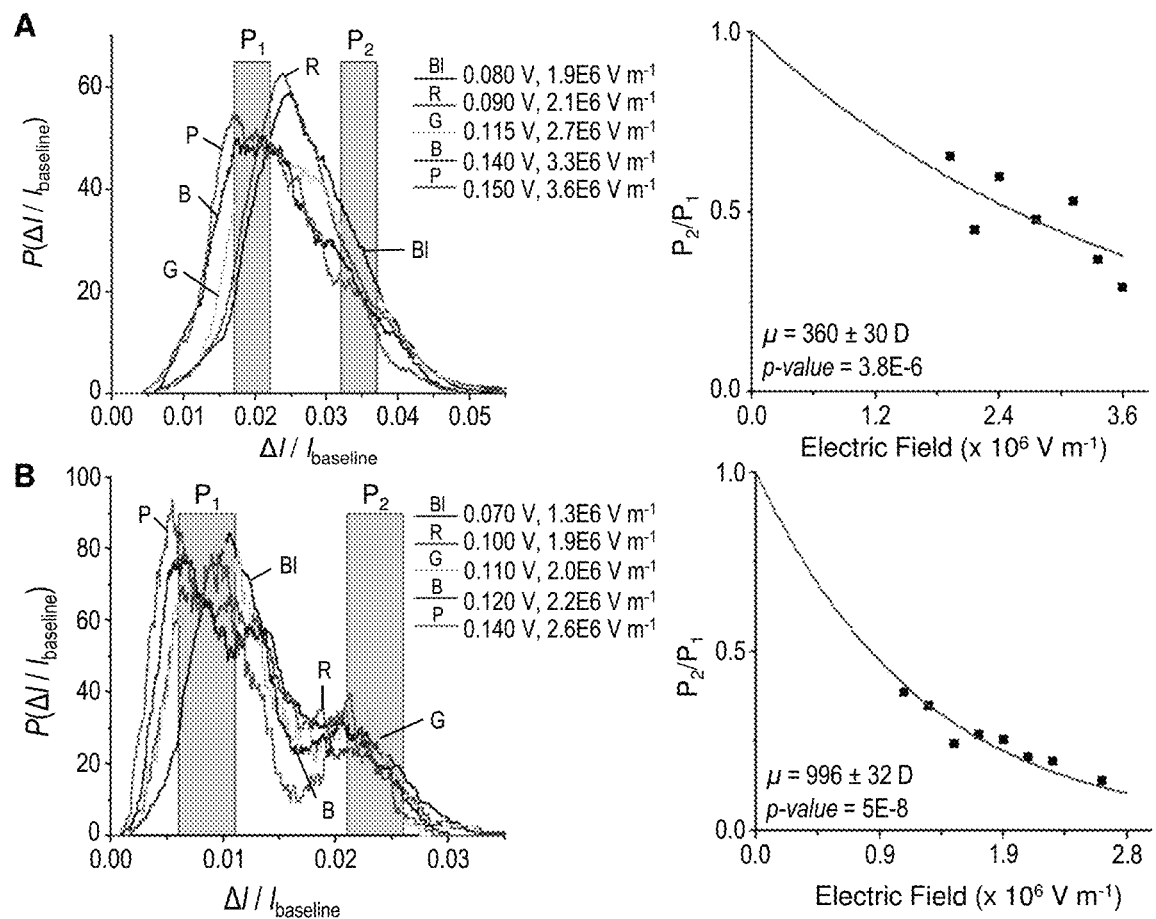

FIG. 19 shows probability distributions of $\Delta I$ due to GPI-acetylcholinesterase (A) and IgG1 antibodies (B) obtained when applying different voltages across the nanopore.

Figure 20:
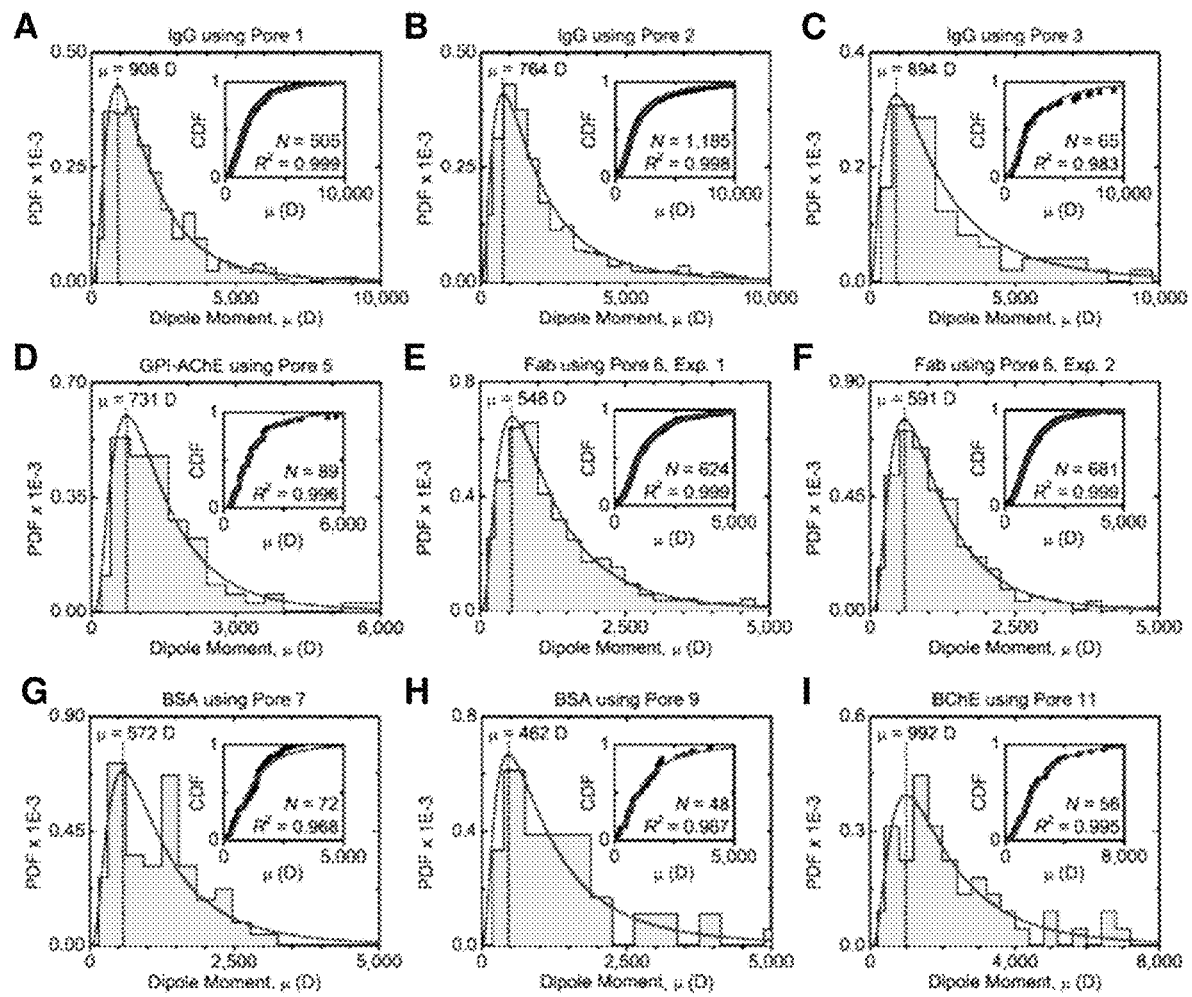

FIG. 20 shows dipole moments, μ, of IgG1 (A-C), GPI-AChE (D), Fab (E-F), BSA (G-H), and BChE (I) determined from fitting intra-event $\Delta I$ values with the convolution model. The inset in each plot shows the empirical cumulative distribution (squares) and corresponding fit with a lognormal cumulative distribution function (CDF) (line). The derivative of the CDF is the probability density function (PDF), which is plotted with the histogram of dipole moments. The most probable value of the dipole moment is indicated by the dotted black line and corresponds to the maximum of the lognormal fit. During the fitting procedure, only events with durations greater than 0.4 ms were analyzed. The applied potential was −100 mV for all experiments with IgG1, Fab, BSA, and BChE and −115 mV for the experiment with GPI-AChE.

Figure 21:
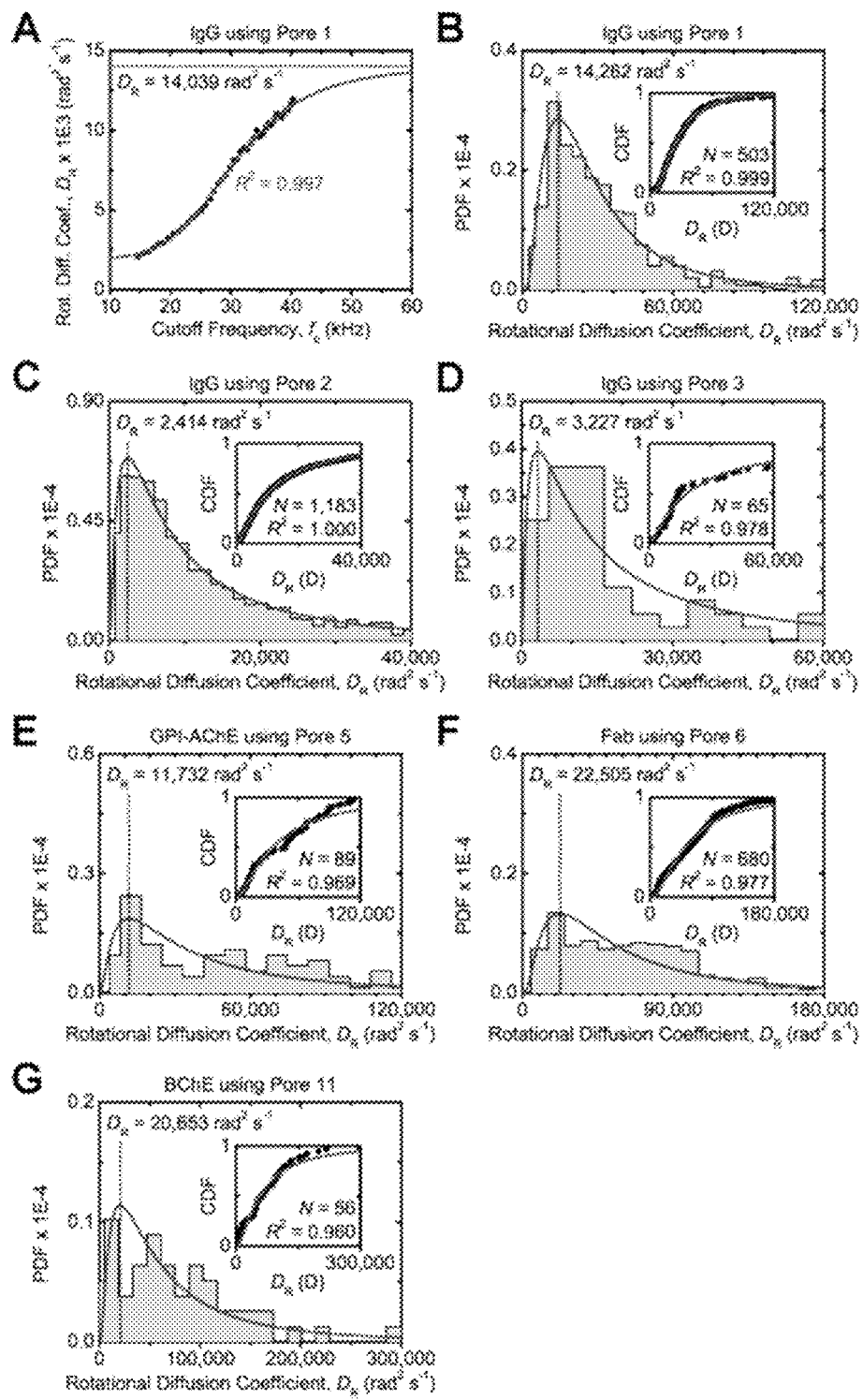

FIG. 21 shows rotational diffusion coefficients, DR, of IgG1 (A-D), GPI-AChE (E), Fab (F), and BChE (G) determined from analysis of intra-event $\Delta I$ values. A) Rotational diffusion coefficient versus the low-pass cutoff frequency for a single event due to IgG1 in pore 1. The curve was fit with the logistic equation to determine DR at infinite bandwidth, which is denoted by the dotted black line. We used this procedure to determine the values of DR for all proteins and subsequently generate the histograms in B-G. B-G) The inset in each plot shows the empirical cumulative distribution (squares) fit with a lognormal cumulative distribution function (CDF) (line). The derivative of the CDF is the probability density function (PDF), which is plotted with the histogram of rotational diffusion coefficients. The most probable value of the rotational diffusion coefficient is indicated by the dotted black line and corresponds to the maximum of the lognormal fit. Only events with durations greater than 0.4 ms were analyzed. The applied potential was −100 mV for all experiments with the IgG1 antibody, Fab, and BChE and −115 mV for the experiment with GPI-AChE.

Figure 22:
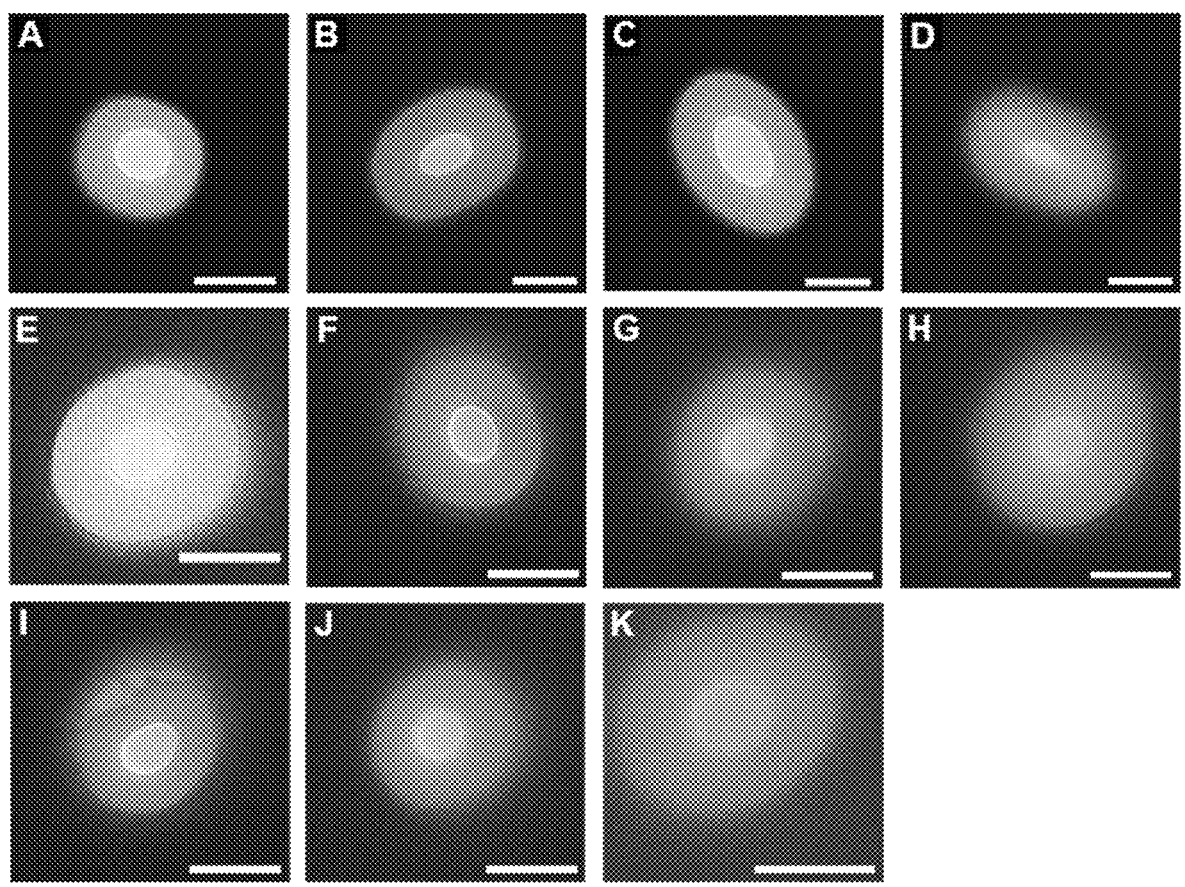

FIG. 22 shows transmission electron micrographs of the nanopores used in this work. The brightest part in the center of each image depicts the shape and size of the nanopore and the surrounding circle with reduced brightness reflects the channel leading to the nanopore.(12, 23) All scale bars are 50 nm. Nanopores shown are pore 1 (A), pore 2 (B), pore 3 (C), pore 4 (D), pore 5 (E), pore 6 (F), pore 7 (G), pore 8 (H), pore 9 (I), pore 10 (J), and pore 11 (K). Using Image J, we measured the area of the nanopore (bright spot in the center) to determine the corresponding radius of a perfect circle with identical area, rP (nm), and we determined the length, lP (nm), of the nanopore from measurements of the electrical resistance of the nanopore.(12) The dimensions of the nanopores (in units of nm) without the lipid bilayer coating were: for pore 1 rP=16.1 and lP=21.3; for pore 2 rP=16.4 and lP=17.3; for pore 3 rP=22.7 and lP=16.2; for pore 4 rP=9.6 and lP=18.0; for pore 5 rP=16.0 and lP=15.0; for pore 6 rP=14.2 and lP=10.0; for pore 7 rP=14.0 and lP=15.4; for pore 8 rP=17.8 and lP=15.5; for pore 9 rP=14.7 and lP=18.0; for pore 10 rP=13.6 and lP=14.0; for pore 11 rP=16.0 and lP=12.0; and for pore 12 (not depicted) rP=21.3 and lP=19.7.

Figure 23:
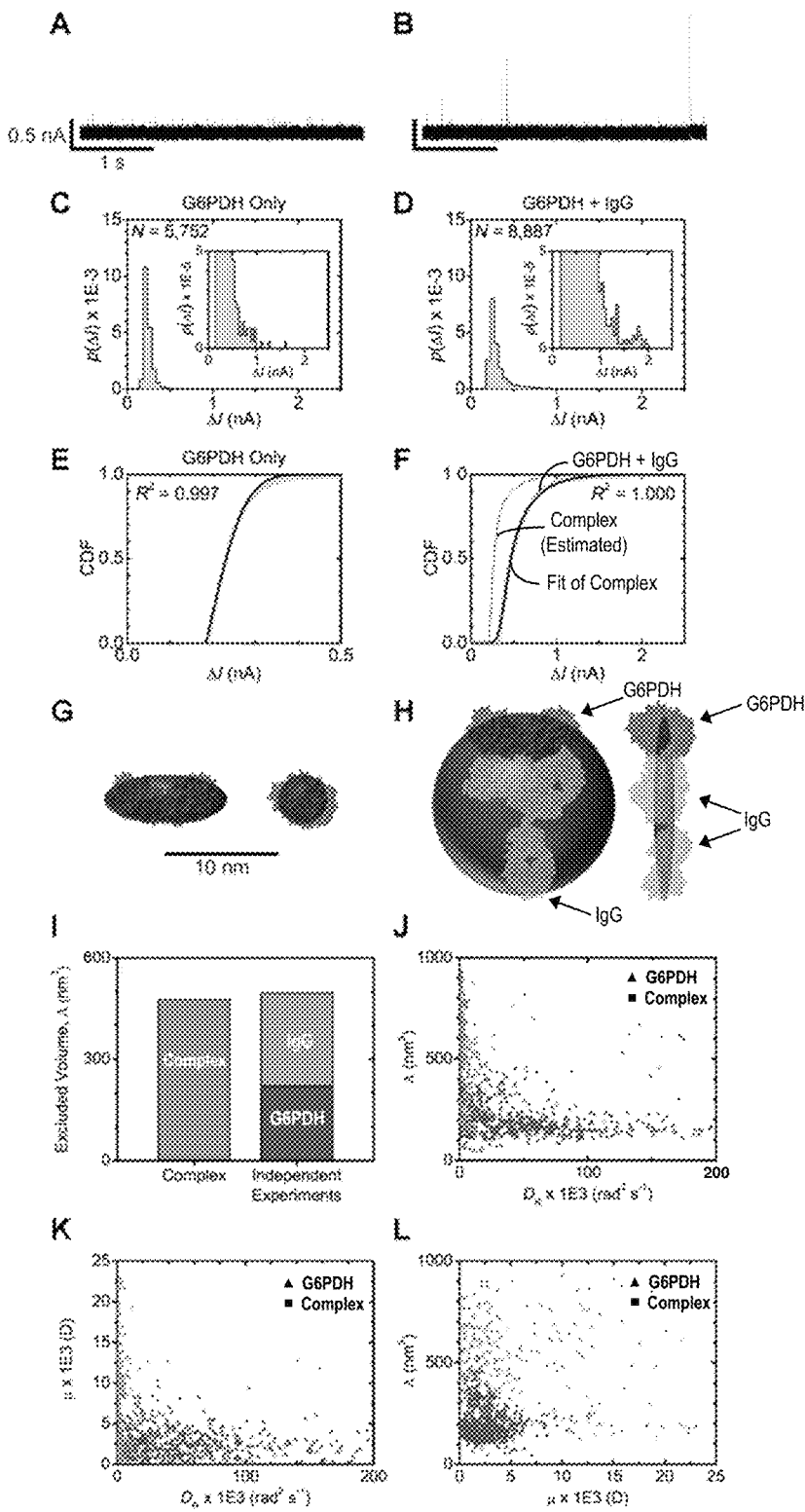

FIG. 23 illustrates determining the volume and shape of an antibody-antigen complex from individual resistive-pulses. A) Current trace showing resistive pulses due to the translocation of G6PDH in the absence of antibody. B) Current trace recorded after incubation with 15 μM polyclonal anti-G6PDH IgG for 1 hr. After incubation, we rinsed the chip with recording buffer to remove unbound IgG. C-D)

Histograms of maximum ΔI values recorded before and after incubation with anti-G6PDH IgG. Insets show the same data over a reduced y-axis scale. We observed a significant increase in the number of events with large ΔI values after incubation with IgG (e.g., the percentage of events with values larger than 500 pA increased from 0.01 to 9 percent). E) Empirical cumulative distribution (CDF) of ΔI values due to the translocation of G6PDH (grey curve) and the fit of this data to the convolution model (black curve). F) Empirical CDF of ΔI values due to the translocation of both G6PDH and the antibody-antigen complex (dotted curve). To generate a CDF due to the translocation of the complex only (i.e., remove ΔI values due to the translocation of unbound G6PDH), we subtracted the CDF due to the translocation of G6PDH only (pane E) after scaling this distribution such that the difference between the two empirical CDFs was minimized at low ΔI values (250 to 350 pA). We expect the majority of ΔI values in this range to result from the translocation of unbound G6PDH. The optimal scaling factor was 0.73, suggesting that roughly 27 percent of translocation events were due to the antibody-antigen complex. G-H) Spheroids show the volume and shape of G6PDH and the antibody-antigen complex determined by fitting the empirical CDFs shown in panes E and F. The crystal structure of G6PDH and IgG are shown. I) Bar plot showing excellent agreement between the volume of the antibody-antigen complex determined from analyzing maximum ΔI values from this experiment and the sum of the volumes of G6PDH and IgG determined that were determined individually in other nanopore experiments (see Table S1). J-L) Scatter plots showing the 2D projections of the 3D plot in FIG. 5C of the main text. These plots show that resistive pulses assigned to the complex correspond to larger molecular volumes and smaller rotational diffusion coefficients than resistive pulses assigned to G6PDH. The dipole moment of G6PDH is relatively clustered as expected for a protein with well-defined shape and position of amino acids. In contrast, the dipole moment of the complex between G6PDH and the polyclonal anti-G6PDH IgG antibody varies widely as expected since IgG may bind at multiple locations and is a relatively floppy molecule. All recordings were obtained with pore 12 at an applied potential of −100 mV and pH of 6.1. We purchased polyclonal anti-G6PDH IgG (A9521) from Sigma Aldrich, Inc.

Figure 24:
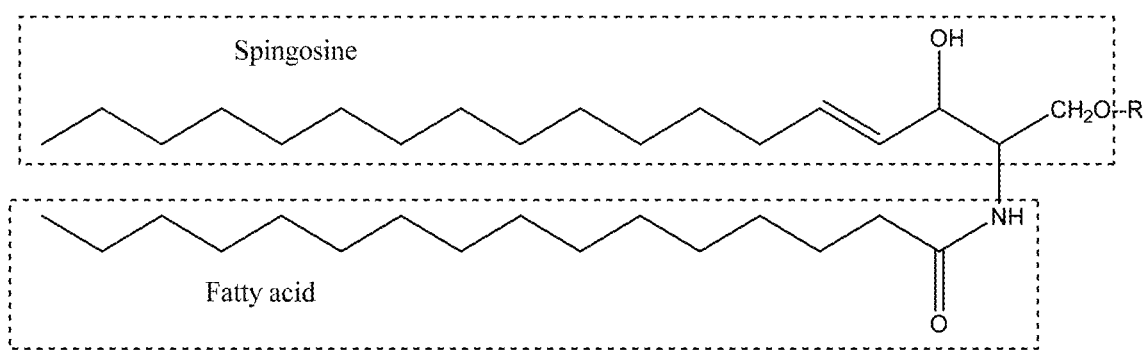

FIG. 24 illustrates a sphingolipid.

DESCRIPTION

In one embodiment, a method of deriving values of physical parameters of macromolecules is provided. The method involves a step of measuring of electrical current I or equivalent electrical parameter as a function of time between two liquid compartments. The liquid compartments are separated by and fluidically coupled through a synthetic nanopore. The electrical current or equivalent electrical parameter is measured upon translocation of a plurality of particles in a plurality of translocation events from one liquid compartment through the nanopore to the other liquid compartment. In various embodiments, the nanopore contains "a fluid wall," as further described below.

The next step of the method is detecting translocation events by recognizing a change in current (ΔI) relative to a baseline current, and afterward collecting values of intra-event values ΔI(t). Then, for a plurality of translocation events, for each translocation event, or at least for a representative sample of the translocation events detected in previous steps, the method involves finding the maximum change in current $\Delta I_{MAX}$ and the minimum change in current $\Delta_{MIN}$. After that, the method involves deriving the volume Λ of the particle and the length to diameter ratio m of the particle from the distribution of values of $\Delta I_{MAX}$ from the translocation events. Finally, the method involves deriving one or more of the rotation diffusion coefficient $D_R$ and of the dipole moment μ of the particle from the volume Λ of the particle, the length to diameter ratio m of particle, and the intra-event values ΔI(t).

In various embodiments, the method involves measuring conductivity, resistivity, resistance, conductance, current flow, voltage, or other electrical parameters measured between the two compartments. In a typical embodiment, current is measured. Thus, in various embodiments, the method involves maintaining a voltage between an anode in one compartment and a cathode in the other compartment, and measuring the current over time as perturbations arising from the passage of individual particles through the nanopore.

Translocation events are analyzed to provide intra-event data. In one embodiment, a translocation event is detected when transient decreases in measured current are greater than a set number of times the standard deviation of the current signal. In a typical embodiment, translocation events are detected when the transient decreases are greater than five times the standard deviation of the current signal. In embodiments, a baseline current is established before introduction of particles into one of the fluid compartments. This baseline and the standard deviation thereof is used to detect translocation in events upon finding a large decrease.

In various embodiments, the particle determined in this way is a macromolecule such as a protein or a spherical protein. In this way a method is provided for detecting the presence of a target molecule in a fluid composition. The method involves determining one or more parameters selected from the volume Λ, the length to diameter ratio m, the rotational diffusion coefficient $D_R$, and the dipole moment μ of the particle in the fluid composition by one of the methods described herein. The measured values of the parameters are compared to corresponding known parameters of a target molecule. As of result, the presence of the target molecule can be determined or confirmed in the composition if the parameters measured from the particle match those of the target macromolecule.

In another embodiment, a method for determining one or more of volume Λ, length to diameter ratio m, the rotational diffusion coefficient $D_R$, and dipole moment μ of a macromolecule in a fluid composition involves a series of data collecting and data transformation steps, some of which can be implicated using a computer or in software written for the computer. The method involves experimentally causing particles in the fluid composition to pass through a nanopore that is disposed between two liquid compartments. The particles flow through the nanopore in a plurality of translocation events, during which the two compartments are held at different voltages, causing an analog signal Ia(t) to flow from one compartment to the other. In the method, the analog signal (for example the analog current signal) is measured and collected as a function of time, both before the particles are added to the fluid composition to establish a baseline, and while the particles are flowing through the nanopore.

After collecting the analog signal, it is converted into a digital signal I(t) and recorded in data files. Thereafter, the I(t) data is transformed to detect translocation events and provide intra-event data. In various embodiments, the data—for example the measured I(t) values—are then further transformed by computing $\Delta I(t)$ for at least a representative sample of events. The $\Delta I(t)$ data are calculated by subtracting $I(t)$ during the events from a baseline $I(t)$ signal.

Thereafter, the method involves finding the maximum $\Delta I$ value of the $\Delta I(t)$ from the events measured in the proceeding step. From the maximum $\Delta I$ value of the measured events, a distribution $P(\Delta I)$ is calculated. If the distribution $P(\Delta I)$ is normal, the volume A is calculated according to equation one given further below, where $\Delta I$ in equation (1) is the maximum of the normal distribution. On the other hand, if $P(\Delta I)$ is not normal, then $P(\Delta I)$ is fit with a model that takes into account the distribution of electrical shape factors, equation (1), and the measurement errors of the technique to estimate $\Delta I_{MIN}$ and $\Delta I_{MAX}$. In various embodiments, a convolution model is used. The estimated values of $\Delta I_{MIN}$ and $\Delta I_{MAX}$ are then substituted into equations S14 and S15, and the equations are solved numerically for the excluded volume A and the value of m for the protein or other macromolecule.

Alternatively, estimates of $\Delta I_{MIN}$ and $\Delta I_{MAX}$ can be obtained from analysis of intra-event $\Delta I(t)$ values. Here, all current values in the intra-event $\Delta I(t)$ signal from one event are used to generate the distribution $P(\Delta I)$. After of the volume of the protein A and the value of m is determined as in the preceding paragraph, those values are used to convert the measured intra-event $\Delta I(t)$ signal to the angle of the particle $\theta$. The rotational diffusion coefficient $D_R$ and dipole moment $\mu$ of the macromolecule are then derived from the values of the angle of the particle $\theta(t)$. As with other methods described herein, in various embodiments, the nanopore between the compartments is lined with a fluid wall. The macromolecule is preferably a bio-macromolecule such as a protein or nucleic acid.

Parameters determined with the methods described herein can be used to identify or quantify macromolecules in a test composition. For example, if known macromolecules are present in a solution, the parameters can be determined as the macromolecules pass through the nanopore in translocation events, and the values of those parameters used to identify the macromolecules.

In a non-limiting example, an affinity assay is provided for determining the binding affinity of a first macromolecule and a second macromolecule, based on the likely situation that a macromolecule and its complex with another macromolecule will have distinguishing parameters of size and shape. The methods described herein are used to essentially count the number of individual macromolecules and complexes in a solution. From the [A], [B], and [AB], an equilibrium constant (affinity constant) $K=[A][B]/[AB]$ is calculated, for example. The value of the equilibrium constant indicates the relative affinity for binding of the first macromolecule to the second macromolecule.

To illustrate, an assay method involves:
(a) combining the first and second macromolecules in a test composition, wherein the test composition comprises the first macromolecule, the second macromolecule, and a complex comprising both macromolecules;
(b) measuring electrical current I or equivalent electrical parameter as a function of time between two liquid compartments separated by and fluidically coupled through a synthetic nanopore upon translocation of particles comprising the first macromolecule, the second macromolecule, and the complex in a plurality of translocation events from one liquid compartment through the nanopore to the other liquid compartment;
(c) detecting translocation events by recognizing a change in current $\Delta I$ relative to a baseline current,
(d) collecting values of intra-event values $\Delta I(t)$;
(e) for a plurality of translocation events, finding the maximum change in current $\Delta I_{max}$ and the minimum change in current $\Delta I_{min}$;
(f) deriving the volume A of the particle and/or the length to diameter ratio m of the particle from the distribution of values of $\Delta I_{max}$ from the translocation events; and/or
(g) deriving one or more of the rotational diffusion coefficient $D_R$ and the dipole moment $\mu$ of the particle from the volume A of the particle, the length to diameter ratio m of the particle, and the intra-event values $\Delta I(t)$
(h) classifying each translocation event as translocation of the first macromolecule, the second macromolecule, or the complex on the basis of the parameter or parameters determined in steps (f) and/or (g); and
(i) deriving an affinity constant for binding of the first macromolecule to the second macromolecule from the data of step (g).

In another embodiment the method permits the simultaneous determination and/or quantification (i.e. measuring the relative concentration) of various macromolecules in a test solution. A method of identifying one or more target macromolecules in a test composition containing a plurality of different macromolecules by measuring and comparing physical parameters of the different macromolecules in solution involves the steps of:
(a) combining the plurality of macromolecules in a test composition, or providing a composition comprising the plurality of macromolecules;
(b) measuring electrical current I or equivalent electrical parameter as a function of time between two liquid compartments separated by and fluidically coupled through a synthetic nanopore upon translocation of particles comprising the plurality of macromolecules in a plurality of translocation events from one liquid compartment through the nanopore to the other liquid compartment, wherein the synthetic nanopore is lined with a fluid wall;
(c) detecting translocation events by recognizing a change in current $\Delta I$ relative to a baseline current,
(d) collecting values of intra-event values $\Delta I(t)$;
(e) deriving the volume A of the particle and/or the length to diameter ratio m of the particle from the intra-event values $\Delta I(t)$; and/or
(f) deriving one or more of the rotational diffusion coefficient $D_R$ and the dipole moment $\mu$ of the particle from the volume A of the particle, the length to diameter ratio m of the particle, and the intra-event values $\Delta I(t)$; and
(g) identifying the presence of a target molecule by matching the derived volume, length to diameter ratio, rotational diffusion coefficient, and/or dipole moment of the particle with the known values of the target macromolecule.

In another embodiment, the method further comprises quantifying the relative number of the individual macromolecules in the solution through the steps of
(h) carrying out step (g) for all translocation events or for a representative sample of translocation events;
(i) classifying each translocation event as translocation of one of the target macromolecules in the test solution; on the basis of the parameter or parameters determined in steps (e) and/or (f); and
(j) counting the data in step (i) to quantify the macromolecule.

In a particular embodiment, the method can be used for an affinity assay. When the test solution comprises a first macromolecule, a second macromolecule, and a complex comprising both the first and second macromolecule, the method further comprises deriving an affinity constant for binding of the first macromolecule to the second macromolecule from the data of step (j).

In various embodiments of the affinity assay, the macromolecules are proteins. In a particular embodiment, the first macromolecule is a protein and the second macromolecule is an antibody that binds the protein.

While methods described herein permit calculation of the charge, volume, length to diameter ratio, rotational diffusion coefficient, and dipole moment of particles and macromolecules as they pass through a nanopore in a translocation event, it is to be understood that in a particular case or situation, not all parameters will necessarily be required to confirm the presence or identity of a particular macromolecule. Thus, in various embodiments, methods involve actual calculation of less than all five of the noted parameters, while still allowing molecules to be identified in a mixture, or equilibrium constants to be generated. In a particular implementation, it may be that full data are collected that would enable a computer software to calculate all the parameters, but that not all the parameters are actually calculated, or if they are calculated, they may not necessarily be output. In various embodiments, enough of the five parameters are calculate d from the data that identification of species can be made for the purposes of the particular investigation.

Preferably but optionally, methods involve processing digital data I(t) with a low pass filter. Standard tests for normality of distribution can be used such as the Kolmogorov-Smirnov test. In methods described herein it is possible to proceed with the analysis by analyzing the intra-event data from every one of the translocation events measured in earlier methods steps. However, if desired, it is also possible to select a representative sample of translocation events for analysis. When an analysis is based on the data from less than all of the translocation events, the representative sample of the events should be chosen with accepted statistical methods.

Fluid Walls

Improved resolution and detection of nanoparticles (which includes proteins and other biomolecules) is achieved when a nanopore connecting liquid compartments, for example in a device running on the Coulter principle, is provided with fluid walls. A fluid wall is provided when a substrate is provided with a fluid coating. A fluid coating in turn is one in which the diffusion coefficient, measured for example by a conventional FRAP (fluorescence recovery after photobleaching) technique is sufficiently high to provide the noted benefits. In one embodiment, a fluid wall is one in which the measured diffusion coefficient measured by FRAP is at least $10^{-18}$ m$^2$ sec$^{-1}$, at least $10^{-16}$ m$^2$ sec$^{-1}$, at least $10^{-14}$ m$^2$ sec$^{-1}$, or at least $10^{-12}$ m$^2$ sec$^{-1}$. Where the fluid lipid walls are made of a lipid monolayer or a lipid bilayer, they can include lipid anchored mobile ligands as part of the lipid bilayer. By varying the nature and concentration of the mobile ligand in the lipid bilayer, multifunctional coatings of lipids are provided that confer unprecedented capabilities to nanopore based sensors. For example, bilayer coatings make it possible to fine tune and actuate pore diameters in sub-nanometer increments. Incorporating lipid anchored mobile ligands confers specificity and slows down the translocation of targeted proteins sufficiently to time resolve translocation events of individual proteins.

In other aspects, advantages are provided because the fluid coatings prevent pore clogging and enable translocation experiments with proteins, peptide oligomers, fibrils, nucleic acids, and other biomolecules. Use of biocompatible fluid coatings described herein nearly eliminates non-specific binding and makes it possible to distinguish proteins by combined analysis of translocation time, volume, charge, shape, ligand affinity, and so on.

A suitable device includes a first liquid compartment, a second liquid compartment, and a synthetic nanopore disposed between the compartments. The nanopore defines a fluid conduit between the first liquid compartment and the second liquid compartment and provides a path for molecules or other nanoparticles in the first compartment to flow to the second compartment. The device also includes electrodes in both liquid compartments and means for controlling the electrodes to measure electrical resistance, voltage difference, or ionic current flow between the first and second electrodes. In an advance for application in so-called nano-Coulter counting, the synthetic nanopore providing a fluid path between the first and second liquid compartments is lined with a fluid wall. In one embodiment, the fluid wall comprises a lipid bilayer. In another, the fluid wall comprises a lipid monolayer. In an exemplary embodiment, a dimension of the synthetic nanopore perpendicular to the fluid flow direction is sub-micrometer, for example on the order of 10 to 500 nm. In preferred embodiments, the dimension is 10 to 50 nm, or 20 to 30 nm.

The length of the fluid path between the first and second liquid compartments, in the fluid flow direction, is about 10 to about 1000 nm, in an exemplary embodiment. For example, the length is about 10 to 300 nm.

A fluid lipid wall lining the nanopore of the Coulter counting device is made of a lipid bilayer, which can include lipid anchored ligands. Exemplary lipids in the bilayer are phospholipids.

A method of using the device involves introducing a solution containing biomolecules into the first liquid compartment. The nanopore connects the first liquid compartment to the second liquid compartment, enabling dissolved molecules to move through the nanopore. As molecules flow through the nanopore, the electric field is perturbed, providing a time based perturbation of the electric field. Current, voltage, resistance and other electrical parameter is measured to provide values of $\Delta I(t)$. The $\Delta I(t)$ values are then analyzed to provide molecular parameters as described below.

In another aspect, a method of measuring the translocation time, ligand affinity, charge, volume, shape, size, rotational coefficient, dipole moment or other characteristic of a biomolecule according to the Coulter principle is provided. The method involves detecting and measuring a change in conductivity, resistivity, resistance, conductance, current flow, voltage, or other electrical parameter measured between two liquid compartments separated by and fluidically coupled through a synthetic nanopore, upon translocation of a biomolecule such as a protein from one liquid compartment through the nanopore to the other liquid compartment. The nanopore comprises a passageway lined with a fluid wall. In one embodiment, the fluid wall comprises a lipid bilayer. The method further involves deriving the desired molecule characteristic from the measured electrical parameter. In preferred embodiments, the nanopore connecting the first and second compartments is about 10 to 100 nm in diameter (the dimension perpendicular to the flow path between the compartments) and is about 10 to 50 nm long (the dimension parallel to the flow path).

The changes in the electrical parameter that are measured in the method arise from the Coulter effect that provides that, in various embodiments, best results are obtained when the diameter or dimension of the molecule is approximately 2% to approximately 65% of the nominal diameter or dimension of the nanopore.

Coulter Counting

In a device operating according the Coulter principle or Coulter effect, particles suspended—or biomolecules dissolved—in an electrolyte solution are drawn through a small aperture, separating two electrodes between which an electric current flows. The aperture is referred to in the current teachings as a nanopore. Nanochannel is sometimes used for the same concept. The voltage applied across the aperture creates a "sensing zone". As particles pass through the aperture (or "sensing zone"), they displace their own volume of electrolyte, momentarily changing the impedance of the aperture.

Fluid coatings include those exhibiting a diffusion coefficient as measured with conventional fluorescence recovery after photobleaching (FRAP) that is sufficiently high to provide the benefits discussed herein, including the ability of the nano-Coulter counter with fluid walls to time resolve the translocation events. In various embodiments, the diffusion coefficient is at least $10^{-18}$ m$^2$ sec$^{-1}$, at least $10^{-16}$ m$^2$ sec$^{-1}$, at least $10^{-14}$ m$^2$ sec$^{-1}$, or at least $10^{-12}$ m$^2$ sec$^{-1}$. Although the invention is not limited by theory, it is believed that the viscosity characteristics of the fluid coatings contribute to the advantages observed when using them. In a preferred aspect, the fluid coating is provided on the nanopore aperture by applying a bilayer or monolayer to the surface of the substrate in the nanopore aperture. Basically, any molecule that is amphipathic is potentially capable of forming a suitable bilayer or monolayer on the substrates to provide nanopores with fluid walls. Examples include a surfactant or detergent having a hydrophilic group and a hydrophobic group. Other examples include without limitation molecules generated from click chemistry that resemble lipids, such as those described in "Vesicle and stable monolayer formation from simple "click" chemistry adducts in water" by Santanu Bhattacharya and Joydeep Biswas in Langmuir 2011 ASAP, the full disclosure of which is incorporated by reference herein. It is preferred in some embodiments to use surfactant, detergent, or lipid materials that have a charged hydrophilic head; in particular embodiments, phospholipids are preferred.

When the surface to which the coating is applied is hydrophilic, amphipathic molecules form or self-assemble on the substrate to make bilayers. When the surface is hydrophobic (or is modified to be hydrophobic, such as by silanization or other technique), amphipathic molecules tend to form a monolayer. In the monolayer, the hydrophobic tail of the amphipathic molecule is attracted to the hydrophobic surface so that the hydrophilic head of the molecule is exposed to the solution being tested. When the substrate has a hydrophilic surface, it attracts the hydrophilic head of the amphipathic molecule, and a bilayer forms such that the hydrophilic head of the second layer is exposed to the solution.

Lipid Coatings

When lipids are applied, they form fluid lipid walls on the nanopore. The lipids that make up the lipid bilayers or monolayers formed on the walls of the substrate to provide the nanopores are amphipathic, having a hydrophilic head and a hydrophobic tail.

Lipid bilayers and monolayers can be applied to the surface of the substrate to provide the nanopores with fluid walls, for example by exposing the substrate to solutions of liposomes made up of lipid components. Lipid bilayers and monolayers are well known.

Suitable phospholipids have a moiety that includes a charged phosphate group forming the hydrophilic head, and one or more fatty acid residues forming the hydrophobic tail. One group of phospholipids is derived chemically from fatty triglycerides by replacing one of the three fatty acid residues with a phosphate group. The phosphate group can be further esterified with functionalizing molecules.

Replacing one of the fatty acid residues on a triglyceride with a phosphate group results in the formation of a phosphatide. The diacylglycerol phosphate formed by a simple substitution of the phosphate for one of the acyl groups is called a phosphatidic acid. If the phosphatidic acid is esterified in turn, the phospholipid is a phosphatidyl lipid. Examples include phosphatidyl choline, phosphatidyl ethanolamine, phosphatidyl serine, phosphatidyl glycerol, and the like.

Phospholipids of the phosphatidic acid and phosphatidyl series are named as glycerol derivatives, naming the acyl or fatty acid group on the one and two hydroxyls of the parent glycerol, with the phosphate or the phosphatidyl group provided at position three of glycerol. Normally two of the three glycerol positions are esterified with fatty acids. In the lysophosphatidyl phospholipids (such as those exemplified in the Table), only the 1 position has a fatty acid moiety, with the phosphate containing group located on the 3-position.

Non-limiting examples of phospholipids in these classes are given in the following table, which illustrates the naming convention and the generic names of the various classes of phospholipid.

TABLE

Representative Phospholipids

| Abbreviation | CAS | Name | Type |
| --- | --- | --- | --- |
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . .) (Sodium Salt) | Phosphatidylglycerol |
| DLOPC | 998-06-1 | 1,2-Dilinoleoyl-sn-glycero-3-phosphocholine | Phosphatidylcholine |

TABLE-continued

Representative Phospholipids

| Abbreviation | CAS | Name | Type |
|---|---|---|---|
| DLPA-NA | | 1,2-Dilauroyl-sn-glycero-3-phosphate (Sodium Salt) | Phosphatidic acid |
| DLPC | 18194-25-7 | 1,2-Dilauroyl-sn-glycero-3-phosphocholine | Phosphatidylcholine |
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . .) (Sodium Salt) | Phosphatidylglycerol |
| DLPG-NH4 | | 1,2-Dilauroyl-sn-glycero-3[Phospho-rac-(1-glycerol . . .) (Ammonium Salt) | Phosphatidylglycerol |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . .) (Sodium Salt) | Phosphatidylglycerol |
| DMPG-NH4 | | 1,2-Dimyristoyl-sn-glycero-3[Phospho-rac-(1-glycerol . . .) (Ammonium Salt) | Phosphatidylglycerol |
| DMPG-NH4/NA | | 1,2-Dimyristoyl-sn-glycero-3[Phospho-rac-(1-glycerol . . .) (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |
| DOPG-NA | 62700-69-0 | 1,2-Dioleoyl-sn-glycero-3[Phospho-rac-(1-glycerol . . .) (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol . . .) (Sodium Salt) | Phosphatidylglycerol |
| DPPG-NH4 | 73548-70-6 | 1,2-Dipalmitoyl-sn-glycero-3[Phospho-rac-(1-glycerol . . .) (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . .) (Sodium Salt) | Phosphatidylglycerol |
| DSPG-NH4 | 108347-80-4 | 1,2-Distearoyl-sn-glycero-3[Phospho-rac-(1-glycerol . . .) (Ammonium Salt) | Phosphatidylglycerol |
| DSPS-NA | | 1,2-Distearoyl-sn-glycero-3-phosphoserine (Sodium Salt) | Phosphatidylserine |
| Egg Sphingomyelin empty Liposome | | | |
| EPC | | Egg-PC | Phosphatidylcholine |
| HEPC | | Hydrogenated Egg PC | Phosphatidylcholine |
| HSPC | | High purity Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |
| Milk Sphingomyelin MPPC | | 1-Myristoyl-2-palmitoyl-sn-glycero 3-phosphocholine | Phosphatidylcholine |

TABLE-continued

Representative Phospholipids

| Abbreviation | CAS | Name | Type |
| --- | --- | --- | --- |
| MSPC | | 1-Myristoyl-2-stearoyl-sn-glycero-3-phosphocholine | Phosphatidylcholine |
| PMPC | | 1-Palmitoyl-2-myristoyl-sn-glycero-3-phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol) . . .] (Sodium Salt) | Phosphatidylglycerol |
| PSPC | | 1-Palmitoyl-2-stearoyl-sn-glycero-3-phosphocholine | Phosphatidylcholine |
| SMPC | | 1-Stearoyl-2-myristoyl-sn-glycero-3-phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholine |

Another class of phospholipids that form bilayers is the sphingolipids. Sphingomyelin is a class of sphingolipids that has a phosphocholine or phosphoethanolamine molecule with an ester linkage to the one hydroxy group of a ceramide. A ceramide in turn consists of a fatty acid chain attached through an amide linkage to sphingosine. An exemplary structure of a sphingolipid is shown in FIG. 24, wherein R is the phosphorocholine or phosphoroethanolamine group. The sphingolipids can vary with the structure of the fatty acid, which is shown in the FIG. as a C17 saturated fatty acid.

Lipid Anchored Ligands

The preferred phospholipids and sphingolipids self-assemble onto the substrate as a bilayer or monolayer when a substrate is exposed to a solution or suspension of liposomes made from the respective phospholipids. The liposomes in turn self-assemble in solution when the component lipids are dissolved in an aqueous system. If desired, a lipid molecule containing a ligand (also called a "liganded phospholipid") is also provided in the solution from which the liposomes are produced. When assembled onto the substrate surface in a bilayer, this provides a lipid anchored ligand in the fluid wall. In certain embodiments, the ligand of the liganded phospholipid serves to bind or otherwise interact with biomolecules or other analytes of interest.

The phospholipid derivatized with the ligand is provided in a suitable mole fraction relative to the other phospholipids. Normally, the mole fraction of the liganded phospholipid is 0.5 or less, and above 0.000001. Depending on the specificity and binding constant of the ligand for the biomolecule, the mole fraction of ligand in the bilayer can be at least 0.000001, at least 0.00001, at least 0.0001, at least 0.001, or at least 0.01 (the numbers are mole fractions ranging from zero to one. A mole percent ligand can be derived by multiplying the mole fraction by 100). In various embodiments, the mole fraction of liganded phospholipid is no more than 0.5, no more than 0.2, no more than 0.1, no more than 0.01, and no more than 0.001. Typical ranges of mole fraction for the liganded phospholipid in the fluid lipid walls are 0.000001-0.2, 0.00001-0.2, 0.001-0.1, 0.01-0.1, 0.000001-0.1, 0.00001-0.1, 0.000001-0.01, 0.000001-0.001, and so on. In a preferred embodiment, the ligand is covalently attached to a structure like that of the other phospholipids in the bilayer. For example, a liganding functional group such as biotin can be covalently attached to the nitrogen of a phosphatidylethanolamine molecule. Many other examples are known or can be synthesized.

The ligand to be incorporated into the bilayer to provide the lipid anchored ligand of the invention is selected from compounds that have a wide range of functional groups. Basically, any functional group to which the biomolecule of interest will bind or link to covalently can be used. For any ligand/biomolecule combination, suitable conditions can be empirically determined. Generally, the stronger the affinity of the ligand and biomolecule (expressed in the conventional way as binding constants or inhibition constants), the lower the mole fraction need be provided of the ligand in the fluid wall. The converse is also true in that the weaker the affinity of the ligand and biomolecule interaction, the higher the mole fraction need be provided of the ligand in the fluid wall. A quick calculation suggests that ~20 mM will be the weakest equilibrium dissociation constant (Kd) that the system will work with for detecting specifically lipid-attached proteins. Stronger affinities (Kd<20 mM) will allow the system to use less ligand in the fluid walls.

The nature of the ligand and its concentration in the bilayer can be varied to provide a suitable amount of binding in the fluid wall lining the nanopore. Although the invention is not limited by theory, this affinity of the biomolecule for the ligand in the fluid wall or the covalent bond of a biomolecule to a lipid in the fluid wall accounts for at least some of the advantages provided by the method. In particular, it is believed that binding to these ligands or covalent bond to a lipid in fluid wall effectively anchors the protein to a lipid in the fluid wall and slows down the translocation of the biomolecule through the nanopore, thereby allowing the electronics to time resolve the translocation events.

Examples of Ligands

Examples of ligands that can be covalently incorporated into the phospholipid bilayers as discussed above include biotin, cholesterol, sulfonamide, nickel (coupled with nickel chelating lipids) and antibodies. Other examples of ligands include proteins. In various embodiments proteins used as ligands contain functional groups or can be modified to contain functional groups that can react for covalent attachment. Examples of such groups on proteins include thiol groups, maleimide groups, N-hydroxysuccimide (NHS) ester groups, or so called "click" chemistry, which proceeds through nitrile, acetylene, or azide groups, or cycloadditions such as the Diels-Alder reaction.

Manufacture of Nanopores

The nanoholes can be fabricated in materials such as silicon nitride, silicon dioxide, borosilicate glass, aluminum oxide, or polyethylene terephthalate. Depending on the material and the size of the desired hole, different fabrication techniques are used. Common techniques include the so called "track etching technique" (Harrell, C. C. et al., (2003), Synthetic single-nanopore and nanotube membranes, *Anal. Chem.* 75:6861-6867), the "ion beam sculpting" technique (Jiali Li et al., (2001), Ion Beam Sculpting at nanometer length scales, *Nature* 412, 166-169), the "electron beam sculpting" technique (Storm, A. J. et al., (2003), Fabrication of solid-state nanopores with single-nanometer precision, *Nat. Mater.* 2:537-540), and "the laser machining in glass" technique (Joglekar et al. (2004), Optics at critical intensity: applications to nanomorphing, *PNAS*, 101: 5856-5861).

When the lipid bilayer is formed in the passageway of the substrate, the effective dimension or diameter of the passageway is reduced by the thickness of the bilayers formed. One speaks then of a nanopore having a nominal dimension that takes into account the lowering of the effective diameter of the passageway as a consequence of the bilayer being formed. Normally the nominal diameter or dimension of the nanopore is the dimension of the passage or hole through the substrate reduced by two times the bilayer thickness plus a layer of water between the lipid bilayer and the substrate surface or one time a monolayers thickness. If the passageway is perfectly round, diameter and dimension are used interchangeably. For shapes other than round, other dimensions can be used, such as chords, long axes, short axes, and the like. Frequently, the dimension of interest is the nominal dimension of the nanopore that permits a non-spherical biomolecule to pass through, in some orientation where the dimension of the biomolecule and the pore are in relation to one another.

The nominal dimension of the nanopore, being a function of the bilayer thickness, is therefore also a function of the length of the "tail" (the acyl chains) on the phospholipids in the bilayer, since the thickness of the bilayer depends on the tail length. The length of the tail in turn depends on the number of carbon atoms and the number of double bonds. These features are illustrated further in the Examples section below. In certain embodiments, the nominal dimension of the nanopores can be fine-tuned by the choice of phospholipid.

Biomolecules

Using the methods and devices described herein, a variety of biomolecules can be detected and studied. Generally speaking, any molecule or particle having nanometer dimensions can be studied a variety of which are exemplified in the examples herein. These include biomolecules such as proteins, nucleic acids, antibodies, polysaccharides, virus capsids, biopolymers such as fibrils and so on as well synthetic particles such as polystyrene particles, gold nanoparticles, or dendritic particles. Additional subjects of study include protein aggregates such as those formed by amyloid beta (Aβ) peptides. Other aggregates include immune complexes and G-protein coupled receptors. By using the nanopores with fluid walls, translocation times of such molecules or particles through nanopores is slowed down sufficiently that the transit or translocation events can be isolated and measured.

Various aspects of the experimental and computational procedures will now be described in non-limiting fashion.

Non-Spherical Proteins Generate a Bimodal Distribution of ΔI Values

To sense proteins (FIG. 1), we mounted nanopores between two fluidic channels (Supplementary Section S1) and coated nanopores with a lipid bilayer comprised of 1-palmitoyl-2-oleoyl-sn-glycero-3-phosphocholine (POPC) lipids and 0.15 mol % 1,2-dipalmitoyl-sn-glycero-3-phosphoethanolamine-N-capbiotinyl (biotin-PE) lipids (FIG. 1a)[24]. The fluid bilayer coating minimizes electroosmotic flow, surface-charge variation, and non-specific interactions with the nanopore surface[24,26,42] and was recently used to improve the sensing characteristics of nanocapillaries for λ-DNA detection[42]. Here, the biotin-PE lipids served as a ligand to bind and effectively lipid-anchor monoclonal anti-biotin IgG$_1$ antibodies, polyclonal anti-biotin IgG fab fragments, and streptavidin on the fluid bilayer surface. In contrast, GPI-AchE self-associated with the lipid bilayer coating via its glycosylphosphatidylinositol (GPI) anchor. The remaining proteins were attached to lipids via a bi-functional, amine-reactive crosslinker to ethanolamine lipids in the bilayer coating. The lipid-anchored proteins are transported to the nanopore via two dimensional diffusion of the lipids in the bilayer coating, and pass through the nanopore with times that are inversely proportional to the product of the diffusion coefficient of the lipids, electric field in the nanopore, and the charge of the protein as predicted theoretically (Supplementary Section S2)[24]. Consequently, the translocation speeds of proteins through the nanopore can be controlled by forming bilayer coatings with different viscosities, and thus, this bilayer-coating strategy enables time-resolved characterization of resistive-pulses due to proteins[24].

Figure 2:
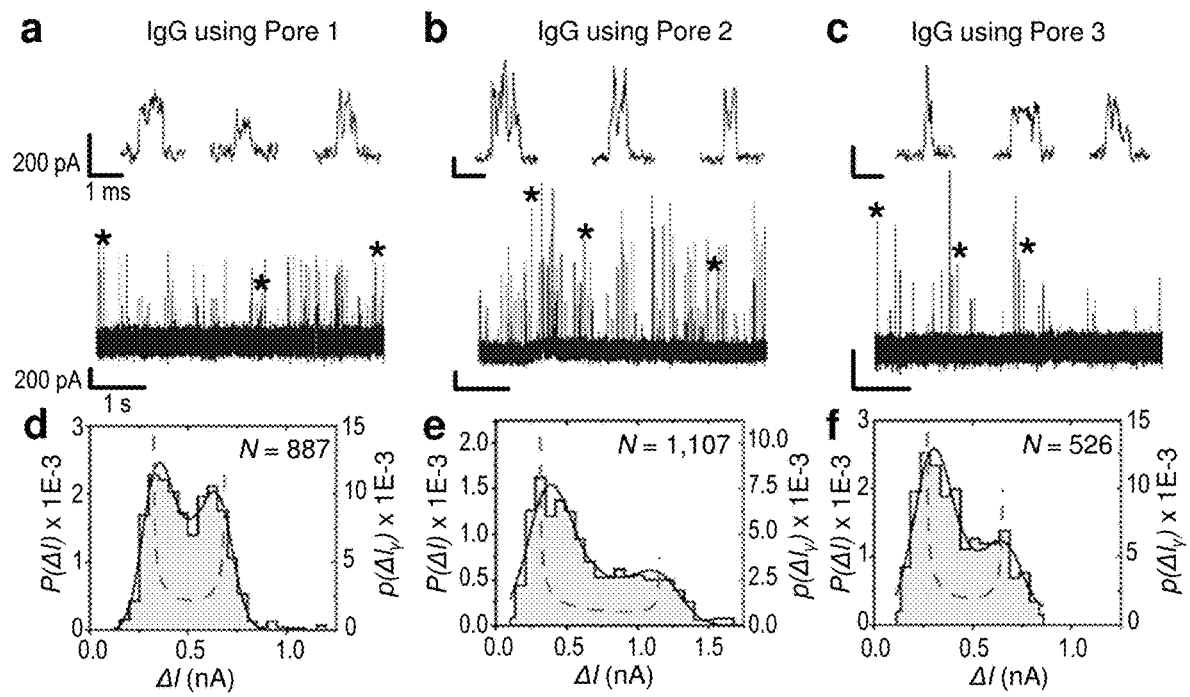
Figure 3:
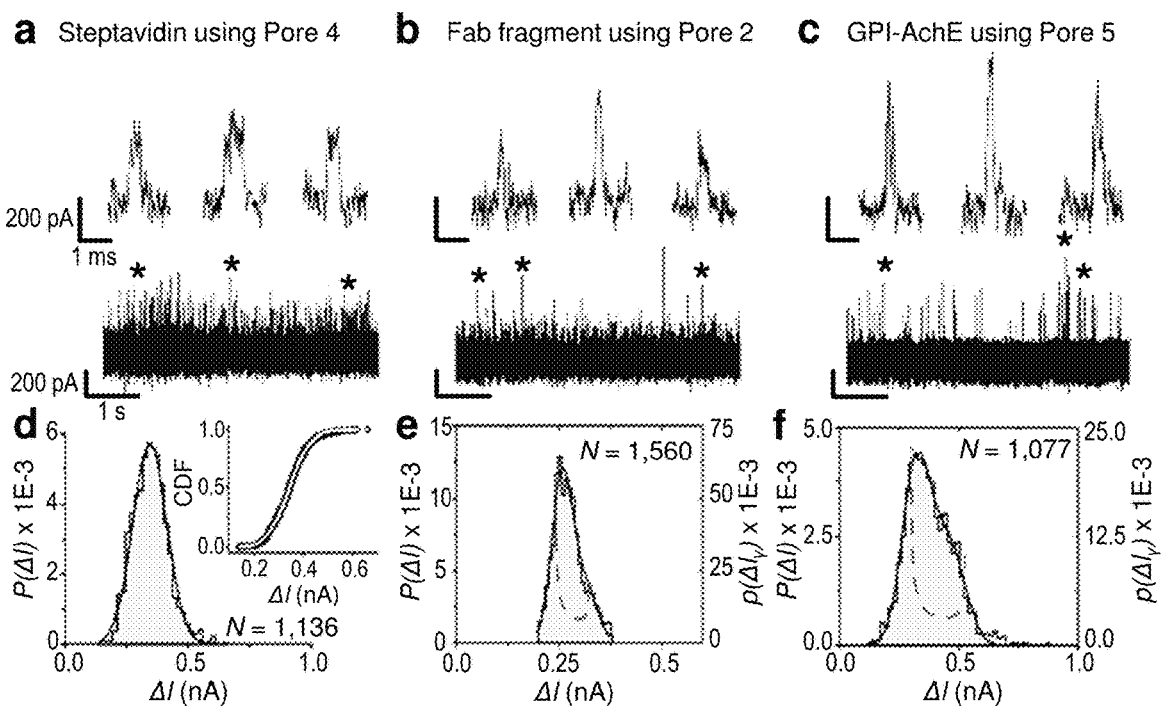

After recording the baseline current, we added the desired protein to the solution on one side of the nanopore and recorded the resulting current pulses. The maximum amplitude of resistive pulses, ΔI, due to the translocation of monoclonal anti-biotin IgG$_1$ antibodies (FIG. 2) were markedly more distributed than the maximum ΔI values due to the translocations of the other proteins (FIG. 3). In fact, the resistive pulses due to long translocation events of IgG$_1$ contained multiple current levels within single translocation events, and we observed these types of distributed ΔI values in three different nanopores of different dimensions. Control experiments confirmed that the widely distributed ΔI values during IgG$_1$ translocations were not due to impurities in the solutions, dimers of IgG$_1$, or translocation of multiple IgG$_1$ proteins simultaneously (Supplementary Section S3). We also confirmed that the large molecular weight of an IgG protein (152 kDa)[43] did not cause the large variations in ΔI, since the translocation of GPI-AchE (160 kDa)[44] through the same nanopore also resulted in a bimodal distribution of ΔI values that was significantly narrower than the distribution of ΔI values due to the IgG antibody (Supplementary Section S4). Furthermore, we compared the distributions of ΔI values due to all of the proteins to the Normal distribution by performing Kolmogorov-Smirnov (KS) tests on empirical cumulative distributions (Supplementary Section S5), and for the three non-spherical proteins (IgG antibody, Fab fragment, and GPI-AchE), the KS-test indicated that the distributions of ΔI values were not Normal (p-values<0.002). In contrast, and as expected[45], the ΔI values due to the translocation of spherical streptavidin proteins were not as widely distributed (FIG. 3A) and were described well by a Normal distribution (p=0.23). Together, these results suggest that the non-Normal distributions were not caused by the geometry of the nanopores or the way in which lipid-anchored proteins diffuse into and out of the nanopore.

Consequently, we hypothesized that the non-spherical shape of the three proteins and their dynamic orientations in the nanopore relative to the electric field generated non-Normal distributions of ΔI values due to the possible values of the orientation-dependent shape factor, γ (unitless)[38,39,41,46-51].

The electrical shape factor has traditionally been set to a value of 1.5 for proteins, and consequently, the average ΔI value is proportional to the volume of the protein according to equation (1)[12,13,20,24,33,35,52]:

$$\Delta I = -\frac{\Lambda V_A \gamma}{\rho(L_p + 0.8D_p)^2} S\left(\frac{d_M}{D_p}\right)$$

where Λ (m³) is the excluded volume of the protein, VA (V) is the applied voltage, LP (m) is the length of the pore, DP (m) is the diameter of the cylindrical pore, and ρ (Ω m) is the resistivity of the electrolyte. $S(d_M/D_P)$ is a correction factor that we set to a value of 1 (Supplementary Section S6)[12,13,24,33,40,52,53]. Thus, for streptavidin, the mean ΔI value corresponds to the molecular volume of 110 nm3 according to equation (1), which is the reported volume (within error) of streptavidin. The width of the Normal distribution reflects measurement errors, σ=70 pA or 25 nm³ (Table 1).

Figure 4:
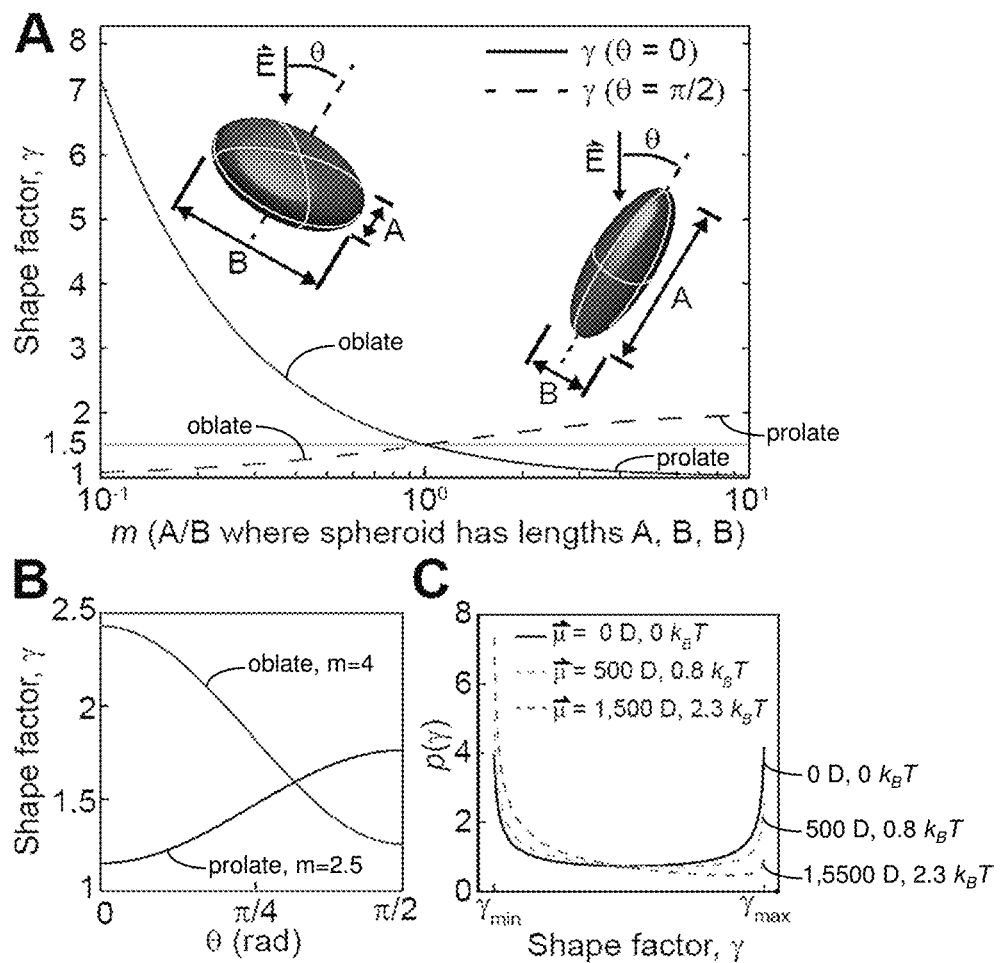

To apply equation (1) for determining the volume and shape of the three non-spherical proteins, we first considered the possible theoretical values of the electrical shape factor. FIG. 4 shows the possible values of the electrical shape factor, γ, as a function of the length to diameter ratio, m, of a spheroid and the angle between the spheroid's axis of revolution and the electric field, θ, (FIGS. 4a and 4b, Supplementary Section S7)[38,39,41,46-51]. Golibersuch derived an expected distribution of shape factors, p(γ), by assuming that the spheroids were randomly oriented when the maximum value of ΔI was determined; the resulting probability distribution of shape factors was bimodal (FIG. 4c black line) and a function of the minimum and maximum possible values of γ for a given shape, $\gamma_{min}$, and $\gamma_{max}$ 38. The two modes of p(γ) occur at $\gamma_{min}$ and $\gamma_{max}$ and correspond to orientations of the particle of θ=0 and θ=π/2. According to equation (1), this bimodal distributions of shape factors would lead to bimodal distributions of maximum ΔI values and, therefore, explain the broad, non-Normal distributions of ΔI values observed with the three non-spherical proteins (FIG. 2 and FIG. 3 e,f).

Furthermore, we considered the time scale of rotation for lipid-anchor proteins and whether the three non-spherical proteins would be prevented from sampling various orientations, and therefore shape factors, by either steric effects or alignment of the dipole moment in the large electric field of the nanopore (Supporting Section S7). Since the rotational diffusion coefficient of GPI-AchE is reported to be $D_r \approx 10,000$ rad² s⁻¹,[54] we expect that a lipid-anchored protein would require approximately 120 μs on average to rotate π/2 radians, which is within the time resolution of these experiments. FIG. 1c shows that the expected lipid anchoring locations on the three non-spherical proteins permits various orientations of the protein that would result in the full range of shape factors, and FIG. 4c shows that even for proteins with a dipole moment of 1,500 Debyes (D) (the average dipole moment of proteins in the Weizmann database is 550 D, according to the website http://biofo.weizmann.ac.il/dipol/aves2.html) a bimodal distribution of shape factors can be expected. Consequently, we hypothesize that the experimentally observed bimodal distributions of maximum ΔI values (FIGS. 2 and 3 e,f) reflect the distribution of shape factors with modes at $\gamma_{min}$ and $\gamma_{max}$, as predicted by Golibersuch[38]. This prediction is supported by our recent discovery of bimodal distributions of ΔI values from translocation of a single, pure protein[24] and subsequent observations made by Raillon et al[30]. In both cases, the bimodal nature of the ΔI distribution was unexpected and a quantitative understanding of this phenomenon was not available. Here, we elucidate the physical mechanism for bimodal distributions of ΔI values based on Golibersuch's pioneering work, and we take this insight further to calculate the shape and volume of proteins based solely on measured ΔI values.

Fitting Distributions of ΔI Values Enables Calculation of a Protein's Shape and Volume.

To determine the excluded volume, Λ, and length to diameter ratio, m, of the proteins from the non-Normal distributions of maximum ΔI values, we first considered that ΔI is directly proportional to γ according to equation (1). Consequently, $\gamma_{min}$ and $\gamma_{max}$ for a given shape correspond to the minimum and maximum ΔI values, $\Delta I_{min}$ and $\Delta I_{max}$, of a given particle, where $\Delta I_{min}$ is a function of $\gamma_{min}(m)$ and Λ, and $\Delta I_{max}$ is a function of $\gamma_{max}(m)$ and Λ (Supplementary Section S8). By determining $\Delta I_{min}$ and $\Delta I_{max}$ from the measured distributions of ΔI values, we can solve for the values of Λ and m of each protein.

Figure 1:
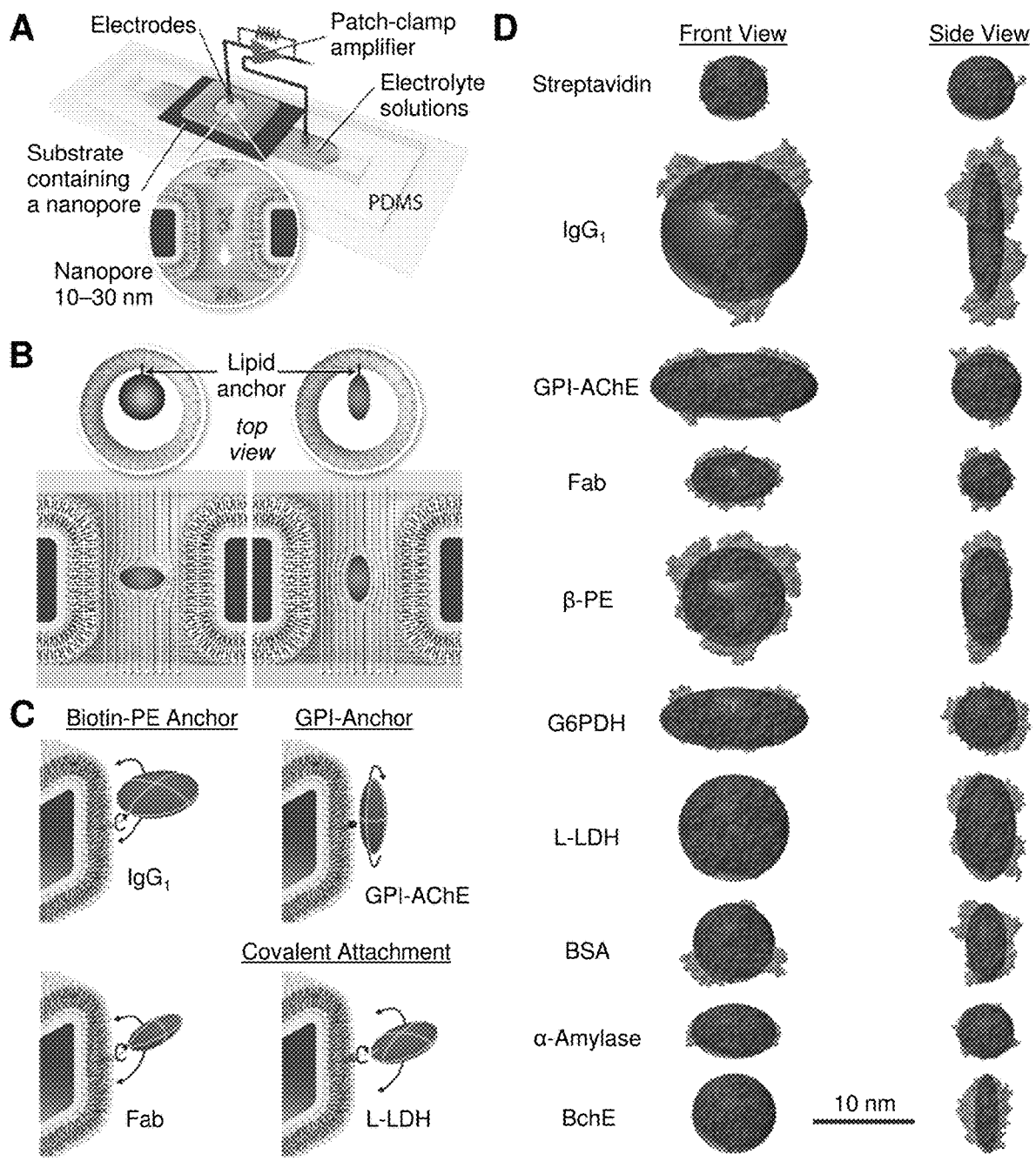

To describe the non-Normal distributions of ΔI values quantitatively based on the distribution of shape factors, p(γ), and to determine $\Delta I_{min}$ and $\Delta I_{max}$, we first converted the distribution of shape factors into a corresponding distribution of ΔI values, $p(\Delta I_\gamma)$ (Supplementary Section S7 and S8). Complicating the analysis is the fact that $p(\Delta I_\gamma)$ is convolved with experimental and analytical noise in determining individual ΔI values, which we describe as a Normal distribution, $p(\Delta I_\sigma)$. Thus, the empirical distributions of ΔI values, P(ΔI), should be described by the theoretical model p(ΔI)= $p(\Delta I_\gamma) \oplus p(\Delta I_\sigma)$, where ⊕ is the convolution operator (Supplementary Section S8)[55]. We fit this model to the empirical distributions of ΔI values using the Levenberg-Marquardt nonlinear-least-squares fitting algorithm in the software Origin Pro 8. The procedure compared the experimental distribution of ΔI values, P(ΔI), to estimates of p(ΔI)[55], and generated new values for the four fitting parameters $\Delta I_{min}$, $\Delta I_{max}$, ΔU, and σ after each iteration (ΔU represents a biasing parameter which is likely dominated by the potential energy of a dipole moment in an electric field, and σ represents the noise). The solid curves in FIGS. 2d-f and 3e-f show the resulting estimate of p(ΔI) and the dashed curves show the estimate of $p(\Delta I_\gamma)$, which is bimodal with modes at $\Delta I_{min}$ and $\Delta I_{max}$. The estimates of p(ΔI) described the empirical distributions of ΔI values well (R2>0.92), and we confirmed by KS-tests that the differences between each empirical P(ΔI) and each estimated p(ΔI) were not statistically significant (p-values>0.31, Supplementary Section S5). Using the resulting estimates of $\Delta I_{min}$ and $\Delta I_{max}$, we solved for the excluded volume of the proteins, Λ, and the length to diameter ratio, m, (Table 1). The calculated values of Λ and m agree well with the expected values for all ten proteins (FIG. 1). For the prolate-shaped Fab fragments and GPI-AchE, we found two solutions to the system of equations, indicating that either an oblate or prolate shaped protein could have generated these non-normal distributions of ΔI values (Supplementary Section S8). In both cases, the value of m that corresponds to a prolate shape (m>1) was close to the value we estimated from the crystal structure of the protein (Table 1), suggesting this solution was correct. FIG. 1b shows the crystal structure of each protein next to the corresponding spheroid and illustrates the close agreement between the shape of the proteins calculated from the analysis presented here and the expected shape based on crystal structures. This result and the good fits of p(ΔI) to the empirical distributions of ΔI values demonstrates that non-Normal distributions of ΔI can be used to determine the volume and shape of proteins in solution.

To provide additional evidence that the orientation and shape of non-spherical proteins affects the distribution of ΔI values, we biased the orientation of $IgG_1$ antibodies and GPI-AchE proteins in the nanopore by changing the electric field in the nanopore (Supplementary Section S9). For both proteins, increasing the strength of the electric field skewed the distribution of ΔI values toward their respective $ΔI_{min}$ values (i.e. θ=π/2 for an oblate and θ=0 for a prolate) and reduced the proportion of events with magnitudes close to the value $ΔI_{max}$. These results indicate that the strong electric field inside the nanopore biased the alignment of the proteins in the pore such that the longest axis of the protein was parallel to the electric field; for a detailed discussion see Supplementary Section S9.

Determining Apparent Rotational Diffusion Coefficients and Dipole Moments.

Figure 5:
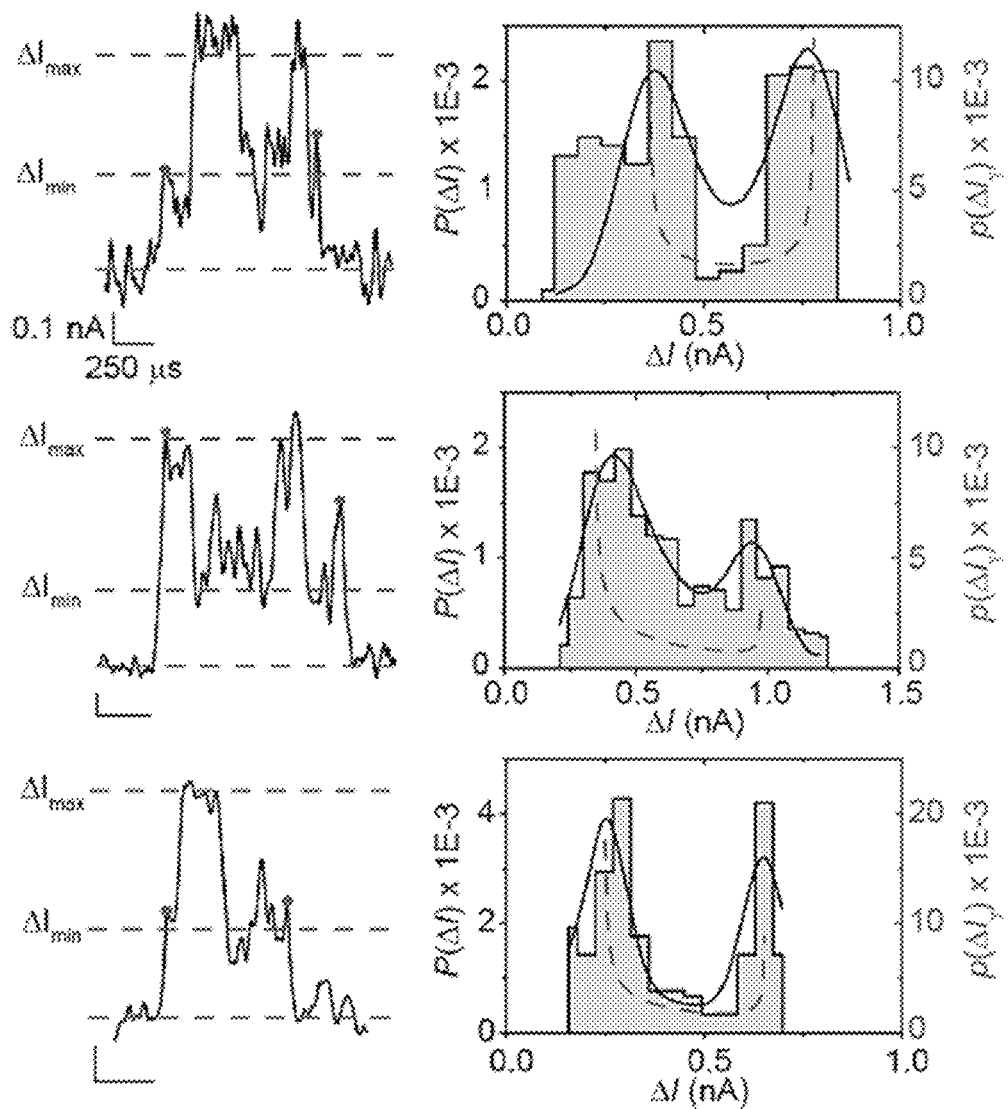
Figure 6:
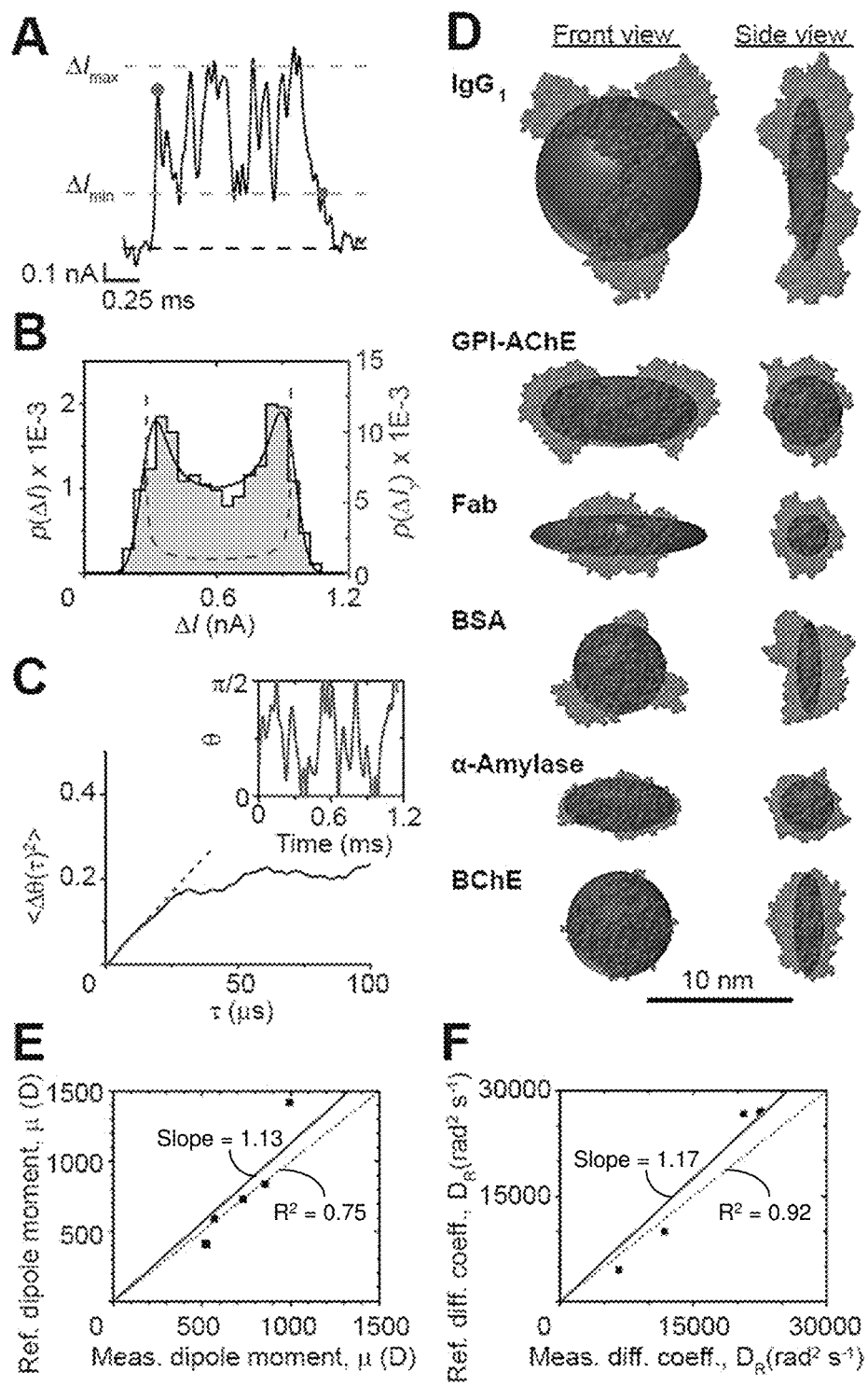

In addition to analyzing the distribution of maximum ΔI values from hundreds of resistive pulses, FIGS. 5 and 6 shows that it is possible to determine the shape of proteins from individual translocation events—and therefore from a single protein in real time during its passage through the pore—by restricting the analysis to resistive pulses with a duration of at least 400 μs. In this case, all recorded values of the electrical current within each individual resistive pulse are analyzed; for example, FIG. 6B shows an empirical probability density distribution of ΔI values from all of the sampled values of the electrical current during a single resistive-pulse. These distributions of single event (or intra-event) ΔI values are analyzed in the same way as the distributions of maximum ΔI values from hundreds of resistive pulses. This intra-event analysis has the additional benefit that it can determine the dipole moment and rotational diffusion coefficient of single proteins by relating time-dependent changes in current to time-dependent changes in the shape factor, γ, which originate from rotations of single proteins during their translocation through the nanopore. To estimate the dipole moment, μ, we characterized the bias in each protein's orientation under the influence of the electric field within the nanopore by fitting the cumulative ΔI distribution to a model that considers the energy difference of a dipole rotating in an electric field (FIG. 6B). To estimate the rotational diffusion coefficient, $D_R$, we transformed the time-dependent intra-event current signal into a time-dependent change in the angle of the protein over short time scales (Supplementary Section S10), plotted the mean-square-angular displacement during a time interval, τ, and fit with a 1-D model for rotational diffusion (FIG. 6C). FIG. 6D shows that the protein shapes determined from this intra-event analysis are in reasonable agreement with their crystal structure, and FIG. 6E,F shows that the values of dipole moment and $D_R$ from this nanopore-based analysis agree well with expected reference values; the average deviation was less than 25% for both parameters.

EXAMPLES

Materials. All phospholipids were obtained from Avanti Polar Lipids. Bis(succinimidyl) penta(ethylene glycol) (21581) was purchased from Thermo Scientific. Monoclonal anti-biotin $IgG_1$ (B7653), GPI-anchored acetylcholinesterase (C0663), glucose-6-phosphate dehydrogenase (G5885), L-lactate dehydrogenase (59747), bovine serum albumin (A7638), α-amylase (A4551), and streptavidin were purchased from Sigma Aldrich, Inc. Polyclonal anti-biotin IgG-Fab fragments (800-101-098) were purchased from Rockland and β-phycoerythrin (P-800) was purchased from Life Technologies.

Methods of Nanopore-Based Sensing Experiments. To sense proteins, we first formed a supported lipid bilayer of 1-palmitoyl-2-oleoyl-sn-glycero-3-phosphocholine (POPC) lipids (Avanti Polar Lipids, Inc.) and a 0.15 mol % fraction of 1,2-dipalmitoyl-sn-glycero-3-phosphoethanolamine-N-capbiotinyl (biotin-PE) lipids on the silicon-nitride surface that contained a nanopore. We described details of the bilayer formation in Yusko et al.[24] and in U.S. Ser. No. 13/400,472, filed Feb. 20, 2012. The dimensions of all nanopores are shown in FIG. 22. After measuring the expected baseline ionic current and confirming the absence of irregular noise, we added solutions containing the desired protein to the top solution compartment of the fluidic setup such that the final concentration of protein ranged from 5 pM to 10 nM. When sensing GPI-anchored acetylcholinesterase, we started recording resistive pulses after incubating the bilayer-coated nanopore for 1 h with GPI-anchored acetylcholinesterase (where the solution was 150 mM KCl, 10 mM HEPES, pH=7.4) to allow time for the GPI-lipid anchor of the protein to insert into the fluid lipid bilayer coating. When POPE lipids were present in the bilayer, we first dissolved bis(succinimidyl) penta(ethylene glycol), a bifunctional crosslinker, in a buffer containing 2 M KCl and 100 mM KHCO3 (pH=8.4) and immediately added this solution to the top compartment of the fluidic setup such that the final concentration of crosslinker was 10 mg/mL. After 10 min, we rinsed away excess crosslinker and subsequently added β-phycoerythrin, glucose-6-phosphate dehydrogenase, L-lactate dehydrogenase, bovine serum albumin, α-amylase, or butyrylcholinesterase dissolved in the same buffer as the preceding step to the top compartment such that final protein concentration ranged from 1 to 3 μM. After at least 30 minutes, we rinsed away excess protein and began recording. We recorded resistive pulses at an applied potential difference of −0.1 V with the polarity referring to the top fluid compartment relative to the bottom fluid compartment, which was connected to ground. The electrolyte contained 2 M KCl with 10 mM HEPES at pH 7.4 (pH=6.1 to 6.5 for experiments with GPI-AchE). We used Ag/AgCl pellet electrodes (Warner Instruments) to monitor ionic currents through electrolyte-filled nanopores with a patch-clamp amplifier (Axopatch 200B, Molecular Devices Inc.) in voltage-clamp mode (i.e., at constant applied voltage). We set the analog low-pass filter of the amplifier to a cutoff frequency of 100 kHz. We used a digitizer (Digidata 1322) with a sampling frequency of 500 kHz in combination with a program written in LabView to acquire and store data.[66] To distinguish resistive pulses reliably from the electrical noise, we first filtered the data digitally with a Gaussian low-pass filter (fc=15 kHz) in MATLAB and then used a modified form of the custom written MATLAB routine described in Pedone et al.[67] We calculated the translocation time, $t_d$, as the width of individual resistive-pulse at half of their peak amplitude, also known as the full-width-half-maximum value[14,24]. From this analysis we obtained the ΔI and td values for each resistive pulse, and we only analyzed ΔI values for resistive-pulses with td values greater than 50 μs, since resistive pulses with translocation times faster than 50 µs have attenuated $\Delta I$ values due to the low-pass filter$^{24,67}$.

REFERENCES

1. Pandey, A. & Mann, M. Proteomics to study genes and genomes. Nature 405, 837-846, (2000).
2. Jachimska, B., Wasilewska, M. & Adamczyk, Z. Characterization of globular protein solutions by dynamic light scattering, electrophoretic mobility, and viscosity measurements. Langmuir 24, 6866-6872, (2008).
3. Erickson, H. P. Size and shape of protein molecules at the nanometer level determined by sedimentation, gel filtration, and electron microscopy. Biol. Proced. Online 11, 32-51, (2009).
4. Wakabayashi, K., Tokunaga, M. et al. Small-angle synchrotron x-ray scattering reveals distinct shape changes of the myosin head during hydrolysis of atp. Science 258, 443-447, (1992).
5. Nierhaus, K. H., Lietzke, R. et al. Shape determinations of ribosomal proteins in situ. Proceedings of the National Academy of Sciences 80, 2889-2893, (1983).
6. Clarke, J., Wu, H. C. et al. Continuous base identification for single-molecule nanopore DNA sequencing. Nat. Nanotechnol. 4, 265-270, (2009).
7. Branton, D., Deamer, D. W. et al. The potential and challenges of nanopore sequencing. Nat. Biotechnol. 26, 1146-1153, (2008).
8. McDougall, Z. Oxford nanopore introduces DNA 'strand sequencing' on the high-throughput gridion platform and presents minion, a sequencer the size of a USB memory stick, <http://www.nanoporetech.com/news/press-releases/view/39> (2012).
9. Kasianowicz, J. J., Brandin, E., Branton, D. & Deamer, D. W. Characterization of individual polynucleotide molecules using a membrane channel. Proc. Natl. Acad. Sci. U.S.A. 93, 13770-13773, (1996).
10. Keyser, U. F. Controlling molecular transport through nanopores. J. R. Soc. Interface 8, 1369-1378, (2011).
11. Majd, S., Yusko, E. C. et al. Applications of biological pores in nanomedicine, sensing, and nanoelectronics. Curr. Opin. Biotech. 21, 439-476, (2010).
12. Han, A. P., Creus, M. et al. Label-free detection of single protein molecules and protein-protein interactions using synthetic nanopores. Anal. Chem. 80, 4651-4658, (2008).
13. Fologea, D., Ledden, B., David, S. M. & Li, J. Electrical characterization of protein molecules by a solid-state nanopore. Appl. Phys. Lett. 91, 053901, (2007).
14. Talaga, D. S. & Li, J. L. Single-molecule protein unfolding in solid state nanopores. J. Am. Chem. Soc. 131, 9287-9297, (2009).
15. Movileanu, L. Interrogating single proteins through nanopores: Challenges and opportunities. Trends in Biotechnology 27, 333-341, (2009).
16. Howorka, S. & Siwy, Z. Nanopore analytics: Sensing of single molecules. Chem. Soc. Rev. 38, 2360-2384, (2009).
17. Kowalczyk, S. W., Blosser, T. R. & Dekker, C. Biomimetic nanopores: Learning from and about nature. Trends in Biotechnology 29, 607-614, (2011).
18. Dekker, C. Solid-state nanopores. Nat. Nanotechnol. 2, 209-215, (2007).
19. Martin, C. R. & Siwy, Z. S. Learning nature's way: Biosensing with synthetic nanopores. Science 317, 331-332, (2007).
20. Sexton, L. T., Horne, L. P. et al. Resistive-pulse studies of proteins and protein/antibody complexes using a conical nanotube sensor. J. Am. Chem. Soc. 129, 13144-13152, (2007).
21. Sexton, L. T., Mukaibo, H. et al. An adsorption-based model for pulse duration in resistive-pulse protein sensing. J. Am. Chem. Soc. 132, 6755-6763, (2010).
22. Merstorf, C., Cressiot, B. et al. Wild type, mutant protein unfolding and phase transition detected by single-nanopore recording. ACS Chemical Biology 7, 652-658, (2012).
23. Oukhaled, G., Mathe, J. et al. Unfolding of proteins and long transient conformations detected by single nanopore recording. Physical Review Letters 98, 158101, (2007).
24. Yusko, E. C., Johnson, J. M. et al. Controlling protein translocation through nanopores with bio-inspired fluid walls. Nat. Nanotechnol. 6, 253-260, (2011).
25. Bayley, H. & Cremer, P. S. Stochastic sensors inspired by biology. Nature 413, 226-230, (2001).
26. Yusko, E. C., Prangkio, P. et al. Single-particle characterization of Ab oligomers in solution. ACS Nano 6, 5909-5919, (2012).
27. Siwy, Z., Trofin, L. et al. Protein biosensors based on biofunctionalized conical gold nanotubes. J. Am. Chem. Soc. 127, 5000-5001, (2005).
28. Ding, S., Gao, C. L. & Gu, L. Q. Capturing single molecules of immunoglobulin and ricin with an aptamer-encoded glass nanopore. Anal. Chem. 81, 6649-6655, (2009).
29. Uram, J. D., Ke, K., Hunt, A. J. & Mayer, M. Submicrometer pore-based characterization and quantification of antibody-virus interactions. Small 2, 967-972, (2006).
30. Raillon, C., Cousin, P. et al. Nanopore detection of single molecule RNAP-DNA transcription complex. Nano Lett 12, 1157-1164, (2012).
31. Soni, G. V. & Dekker, C. Detection of nucleosomal substructures using solid-state nanopores. Nano Lett, (2012).
32. Robertson, J. W. F., Rodrigues, C. G. et al. Single-molecule mass spectrometry in solution using a solitary nanopore. Proc. Natl. Acad. Sci. U.S.A. 104, 8207-8211, (2007).
33. Ito, T., Sun, L. & Crooks, R. M. Simultaneous determination of the size and surface charge of individual nanoparticles using a carbon nanotube-based Coulter counter. Anal. Chem. 75, 2399-2406, (2003).
34. Bacri, L., Oukhaled, A. G. et al. Dynamics of colloids in single solid-state nanopores. Journal of Physical Chemistry B 115, 2890-2898, (2011).
35. Yusko, E. C., Billeh, Y. N., Yang, J. & Mayer, M. in Nanopores: Sensing and fundamental biological interactions (eds S. M. Iqbal & R. Bashir) 203-225 (Springer Publishing Co., 2011).
36. Wei, R., Gatterdam, V., Wieneke, R., Tampe, R. & Rant, U. Stochastic sensing of proteins with receptor-modified solid-state nanopores. Nat. Nanotechnol. 7, 257-263, (2012).
37. Rigler, R. & Vogel, H. in Springer series in biophysics (Springer-Verlag, Berlin, 2008).
38. Golibersuch, D. C. Observation of aspherical particle rotation in Poiseuille flow via the resistance pulse technique. Part 1. Application to human erythrocytes. Biophys. J. 13, 265-280, (1973).
39. Golibersuch, D. C. Observation of aspherical particle rotation in Poiseuille flow via the resistance pulse technique. Part 2. Application to fused sphere dumbbells. J. Appl. Phys. 44, 2580-2584, (1973).

40. DeBlois, R. W., Uzgiris, E. E., Cluxton, D. H. & Mazzone, H. M. Comparative measurements of size and polydispersity of several insect viruses. Anal. Biochem. 90, 273-288, (1978).
41. Deblois, R. W. & Wesley, R. K. A. Viral sizes, concentrations, and electrophoretic mobilities by nanopar analyzer. Biophys. J. 16, A178-A178, (1976).
42. Hernandez-Ainsa, S., Muus, C. et al. Lipid-coated nanocapillaries for DNA sensing. Analyst Advanced Article, (2013).
43. Schneider, S. W., Larmer, J., Henderson, R. M. & Oberleithner, H. Molecular weights of individual proteins correlate with molecular volumes measured by atomic force microscopy. Pflugers Arch. 435, 362-367, (1998).
44. Goodsell, D. Acetylcholinesterase. June 2004 molecule of the month., <http://www.rcsb.org/pdb/101/motm.do?momID=54> (2004).
45. Davenport, M., Healy, K. et al. The role of pore geometry in single nanoparticle detection. ACS Nano, (2012).
46. Grover, N. B., Naaman, J., Ben-sasson, S. & Doljansk, F. Electrical sizing of particles in suspensions. I. Theory. Biophys. J. 9, 1398-1414, (1969).
47. Grover, N. B., Naaman, J., Ben-sasson, S., Doljansk, F. & Nadav, E. Electrical sizing of particles in suspensions. 2. Experiments with rigid spheres. Biophys. J. 9, 1415-1425, (1969).
48. Hurley, J. Sizing particles with a Coulter counter. Biophys. J. 10, 74-79, (1970).
49. Osborn, J. A. Demagnetizing factors of the general ellipsoid.
Physical Review 67, 351-357, (1945).
50. Carbonaro, A., Mohanty, S. K., Huang, H. Y., Godley, L. A. & Sohn, L. L. Cell characterization using a protein-functionalized pore. Lab Chip 8, 1478-1485, (2008).
51. Berge, L. I., Feder, J. & Jossang, T. in Particle size analysis (eds N. G. Stanley-Wood & R. W. Lines) 374-383 (The Royal Society of Chemistry, 1992).
52. Qin, Z. P., Zhe, J. A. & Wang, G. X. Effects of particle's off-axis position, shape, orientation and entry position on resistance changes of micro Coulter counting devices. Meas. Sci. Technol. 22, (2011).
53. Smythe, W. R. Flow around a spheroid in a circular tube. Phys.
Fluids 7, 633-638, (1964).
54. Yuan, Y. & Axelrod, D. Subnanosecond polarized fluorescence photobleaching— rotational diffusion of acetylcholine-receptors on developing muscle-cells. Biophys. J. 69, 690-700, (1995).
55. Woodside, M. T., Anthony, P. C. et al. Direct measurement of the full, sequence-dependent folding landscape of a nucleic acid. Science 314, 1001-1004, (2006).
56. Ozinskas, A. J. in Topics in fluorescence spectroscopy Vol. 4 (ed Joseph R. Lakowicz) 487 (Kluwer Academic Publishers, 1994).
57. Carrasco, B., Garcia de la Torre, J. et al. Crystallohydrodynamics for solving the hydration problem for multi-domain proteins: Open physiological conformations for human IgG. Biophysical Chemistry 93, 181-196, (2001).
58. Cheng, Z., Chaikin, P. M. & Mason, T. G. Light streak tracking of optically trapped thin microdisks. Physical Review Letters 89, (2002).
59. Mason, T. G., Gang, H. & Weitz, D. A. Diffusing-wave-spectroscopy measurements of viscoelasticity of complex fluids. J. Opt. Soc. Am. A 14, 139-149, (1997).
60. Porschke, D., Creminon, C. et al. Electrooptical measurements demonstrate a large permanent dipole moment associated with acetylcholinesterase. Biophys. J. 70, 1603-1608, (1996).
61. Antosiewicz, J., Wlodek, S. T. & McCammon, J. A. Acetylcholinesterase: Role of the enzyme's charge distribution in steering charged ligands toward the active site. Biopolymers 39, 85-94, (1996).
62. Janssen, X. J. A., Lipfert, J. et al. Electromagnetic torque tweezers: A versatile approach for measurement of single-molecule twist and torque. Nano Lett 12, 3634-3639, (2012).
63. Longman, E., Kreusel, K. et al. Estimating domain orientation of two human antibody IgG4 chimeras by crystallohydrodynamics. Eur. Biophys. J. Biophys. Lett. 32, 503-510, (2003).
64. Rosenstein, J. K., Wanunu, M., Merchant, C. A., Drndic, M. & Shepard, K. L. Integrated nanopore sensing platform with sub-microsecond temporal resolution. Nat Meth 9, 487-492, (2012).
65. Avanti Polar Lipids. Conjugation to liposomes brochure, <http://avantilipids.com/download.php?file=Brochures/Avanti_Brochure_Conjugation.pdf> (2012).
66. Uram, J. D., Ke, K. & Mayer, M. Noise and bandwidth of current recordings from submicrometer pores and nanopores. ACS Nano 2, 857-872, (2008).
67. Pedone, D., Firnkes, M. & Rant, U. Data analysis of translocation events in nanopore experiments. Anal. Chem. 81, 9689-9694, (2009).
68. Janeway, C. A. Immunobiology: The immune system in health and disease. 5th edn, (Garland Publishing, 2001).
69. de la Torre, J. G. & Carrasco, B. Hydrodynamic properties of rigid macromolecules composed of ellipsoidal and cylindrical subunits. Biopolymers 63, 163-167, (2002).
70. Neish, C. S., Martin, I. L., Henderson, R. M. & Edwardson, J. M. Direct visualization of ligand-protein interactions using atomic force microscopy. Br. J. Pharmacol. 135, 1943-1950, (2002).

Analysis Flowchart

In the following section, DI and $\Delta I$ are used interchangeably.

Current I, voltage V, resistance R, or other electrical parameter is measured as a function of time between two fluid compartments connected by a nanopore with fluid walls as a biomolecule is made to pass through the nanopore from one compartment to the other. The parameters are interchangeable, but the invention will be illustrated with measurements of current I(t). the following steps are carried out. Some of the steps of the method involving generating data from the experimental set-up. Other steps involve transforming the data, where necessary with the aid of a computer, to provide useful information about the materials passing from one compartment to the other. Here follows a general outline of steps.

1. Convert the Analog I(t) into a Digital Signal and Record I(t) in Data Files

This process is performed with commercial analog-to-digital converters. It is a combination of hardware and software that is part of the recording setup.

2. Transforming the Data to Detect Translocation Events and Intra-Event Data

Optionally but preferably the data I(t) are processed with a low-pass filter. This establishes a baseline I(t) signal, usually with a moving average also being calculated. An event is recognized when the transient decreases in I(t) are greater than a set multiple of the standard deviation or noise in the I(t) signal. A typical threshold for event location is 5 times the standard deviation of I(t). The method then further transforms the current measurements by computing ΔI(t) for each event by subtracting I(t) during events from the baseline I(t) signal. These are intra-event ΔI(t).

Next the method finds the maximum ΔI value of each event and computes td for each event, commonly by taking the full-width-half-maximum (i.e. half-width) of each event peak.

Various event detection methods exist in the resistive-pulse sensing field. A basic method suitable for use is based on one published (and provided by) Pedone et al. "Data analysis of translocation events in nanopore experiments" Analytical Chemistry 2010.

Figure 7:
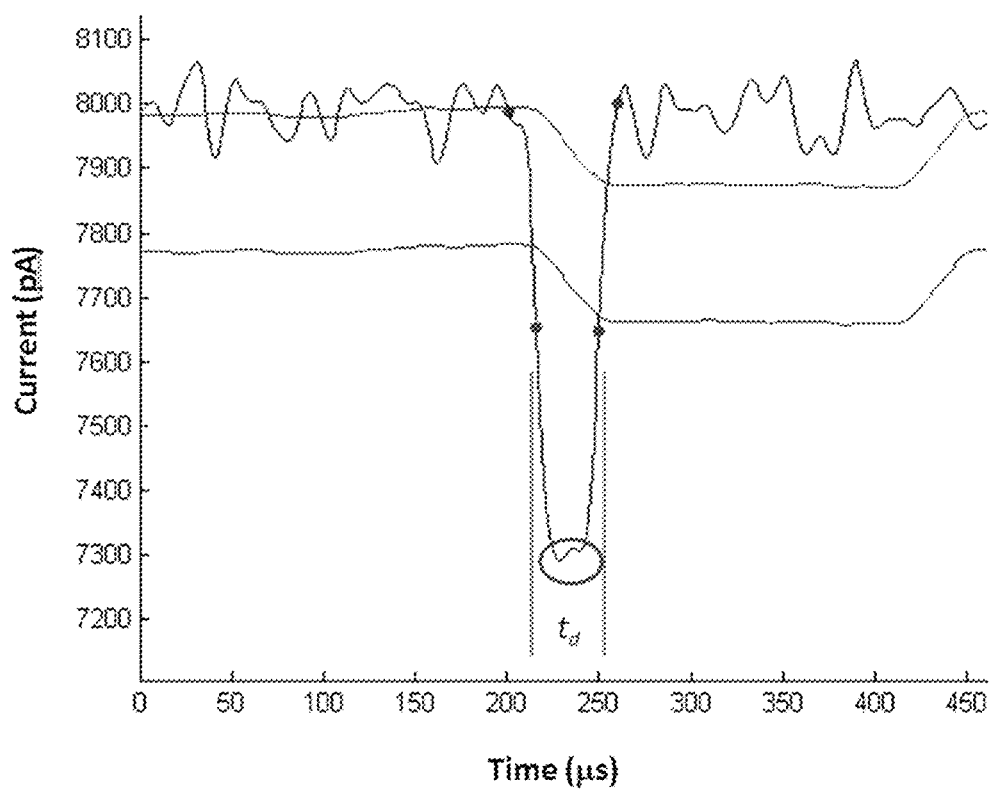

An illustration of the signal, noise, and event detection is given in FIG. 7.

3. Check Distributions of the Maximum ΔI Value, P(ΔI), for Normality

3a. If P(ΔI) is Normal, the Particle is Spherical; Calculate Volume Using Eq. (1)

If the distribution is normal, m is set to a value of 1, and therefore γ=1.5 (FIG. 4), and equation (1) is used to determine the volume of the particle.

Figure 8:
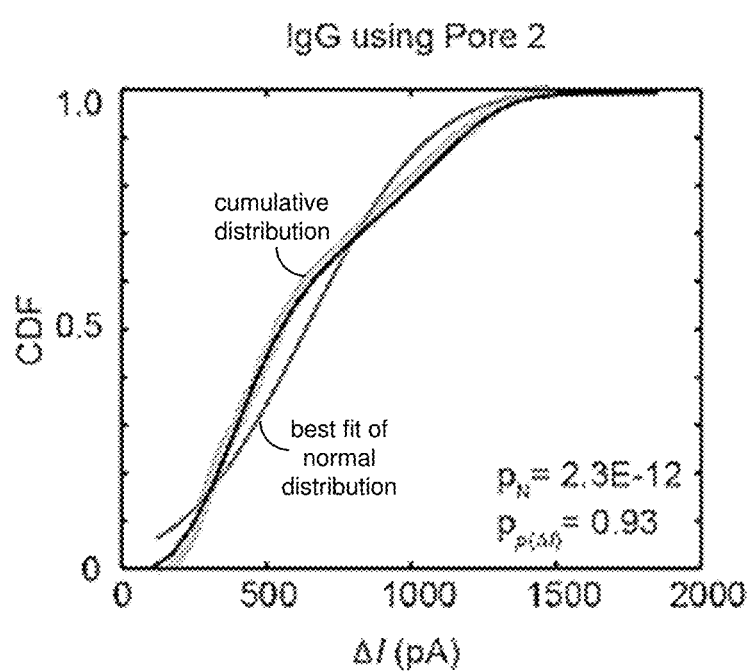

After the event-finding algorithm has processed all of the data (typically finding several hundred or thousands of events), it checks whether the distribution of maximum ΔI values follows a Normal distribution (i.e. Gaussian). We used Kolmogorov-Smirnov test (KS-Test). The test compares cumulative distributions, which can be generated without binning any data. Graphically it looks like FIG. 8:

In FIG. 8, the thicker line illustrates a measured cumulative distribution of the maximum—ΔI values. The thinner line shows the best fit of Normal distribution to the data. Performing a KS-test compares these two distributions (i.e. curves), taking into account the number of observations, and returns a p-value. For a KS-Test the null hypothesis is that the two distributions are the same. Generally when a p-value is considered significant when less than 0.05, 0.01, or 0.001. Depending on what confidence level you want a p-value less than any of these values would indicate that the distributions are different (i.e. not normal). If they are the same, the method considers the protein to be spherical and uses equation (1) to determine the volume of the particle. This is a proper conclusion because the electrical shape factor of a sphere is independent of orientation (i.e. a sphere "appears" the same from all vantage points).

3b. If P(ΔI) is not Normal, Fit P(ΔI) with the convolution model to estimate $\Delta I_{min}$ and $\Delta I_{max}$ This transformation step convolves equation (S13) with a Normal distribution, and compares the resulting distribution to P(ΔI). The 1st convolution requires initial values for the fitting procedure, which can be user defined or estimated in the process; estimates of values are needed for $\Delta I_{min}$, $\Delta I_{max}$ the potential energy of a dipole in an electric field (ΔU), and the noise of the experiment (σ). The method uses non-linear least squares algorithms (e.g. Levenberg-Marquardt) to generate new values for each parameter iteratively.

Consider FIG. 4C and see that the expected distribution of shape factors, g, has two local maxima that correspond to $g_{\parallel}$ and $g_{\perp}$. The subscripts of the symbols for parallel and perpendicular indicate the orientation of the particle relative to the electric field—specifically the angle between the electric field and the axis of rotation of the particle (FIG. 4). Equation (S12) describes this behavior when the variable g ranges between $\gamma_{\parallel}$ and $\gamma_{\perp}$. Because DI is directly related to the value of the electrical shape factor by equation 1, equation 12 can be rewritten in terms of DI to arrive at equation S13 (See Supporting Info S7). Note $g_{\parallel}$ and $g_{\perp}$ are described in eq. S5-S7.

$$P(\gamma)d\gamma = \frac{1}{A}\cosh\left[\frac{E\mu\left(\frac{\gamma-\gamma_{\perp}}{\gamma_{\parallel}-\gamma_{\perp}}\right)^{1/2}}{k_B T}\right]\left[\frac{1}{\pi[(\gamma-\gamma_{\perp})(\gamma_{\parallel}-\gamma)]^{1/2}}\right]d\gamma \quad (S12a)$$

$$P(\gamma)d\gamma = \frac{1}{A}\cosh\left[\frac{E\mu\left(\frac{\gamma-\gamma_{\parallel}}{\gamma_{\perp}-\gamma_{\parallel}}\right)^{1/2}}{k_B T}\right]\left[\frac{1}{\pi[(\gamma-\gamma_{\perp})(\gamma_{\parallel}-\gamma)]^{1/2}}\right]d\gamma \quad (S12b)$$

$$P(\Delta I_\gamma)d\Delta I_\gamma = \frac{1}{A}\cosh\left[\frac{E\mu\left(\frac{\Delta I-\Delta I_{max}}{\Delta I_{min}-\Delta I_{max}}\right)^{1/2}}{k_B T}\right]$$
$$\left[\frac{1}{\pi[(\Delta I-\Delta I_{max})(\Delta I_{min}-\Delta I)]^{1/2}}\right]d\Delta I_\gamma \quad (S13a)$$

and $$P(\Delta I_\gamma)d\Delta I_\gamma = \frac{1}{A}\cosh\left[\frac{E\mu\left(\frac{\Delta I-\Delta I_{min}}{\Delta I_{max}-\Delta I_{min}}\right)^{1/2}}{k_B T}\right]$$
$$\left[\frac{1}{\pi[(\Delta I-\Delta I_{max})(\Delta I_{min}-\Delta I)]^{1/2}}\right]d\Delta I_\gamma \quad (S13b)$$

The analytical expressions of S13 allow us to estimate a starting point for the fitting procedure, but as is evident the plots in FIG. 4 for the distribution of shape factors do not resemble the distributions of maximum ΔI values that were obtained. That fact is because there are experimental and analytical errors in the experiment that are convolved (or overlaid) with the distribution of shape factors (i.e. equation S12 in terms of ΔI in equation S13). So what the method does is estimate an initial $\Delta I_{max}$ (corresponding to the maximum shape factor) and an $\Delta I_{min}$ value (corresponding to the minimum shape factor) (Left Plot in FIG. 9)—it then convolves this distribution with a Normal distribution (center)—resulting in an estimate of the distribution of ΔI values might look like. The method compares the plot on the left to the experimentally observed distribution of ΔI values and generates new fitting parameters using non-linear least squares fitting procedures.

The fitting parameters are $\Delta I_{min}$, $\Delta I_{max}$, and the value of s in the normal distribution. At the end of the fitting procedure, the convolved signal (black curve from the plot on the right in FIG. 9) should resemble the experimental distribution of ΔI values. For instance—the solid curve is the solution in FIG. 10, and it describes the data very well.

4. Solve for the volume of the particle, Λ, and the length to diameter ratio, m, of the particle This step solves a system of equations (numerically); equations are summarized in eq. (S14) and (S15). This step is possible because $\Delta I_{min}$ and $\Delta I_{max}$ are both a function of m and Λ.

Steps 3-4 of the method can also be applied to intra-event ΔI(t) values, where the distribution P(ΔI) is the distribution of the intra-event ΔI(t) values (e.g. FIG. 5), in cases where the macromolecule has been observed long enough.

As a help for understanding this step, consider what FIG. 4 (which plots equations S5-S7) is showing. The electrical shape factor depends on the orientation of particle as well as its shape, characterized here by a parameter m—the length to diameter ratio of the general spheroid. This FIG. and FIG. 4B (in particular) shows something important: for any value of m, that is for any shape, there are a range of electrical shape factors depending on the orientation of the particle. This FIG. shows the minimum and maximum shape factors for a given value of m. Depending on whether the particle is a prolate or an oblate, these min and max shape factors occur when the particle's axis of rotation is parallel or perpendicular (the angle theta) to the electric field. To simplify the discussion in the next steps reference will be made to $g_{max}$ or $g_{min}$, but, as seen in this FIG., whether it refers to $g_{II}$ or $g_{I}$ depends on whether the spheroid is prolate or oblate (equations S5-S7).

Equation 1 shows that the magnitude of the current reduction, ΔI, is a function of the size of the nanopore, the magnitude of the applied voltage, the volume of the particle, and the electrical shape factor. Since we know the first two parameters from the experiment, the only two parameters we do not know for a protein are its volume and electrical shape factor. The electrical shape factor is itself dependent on the orientation of the particle and the shape (i.e. the length to diameter ratio of the spheroid, which we label with a parameter m). In principle this step is relatively simple. Keep in mind that the parameter we have designated ΔImin corresponds to the minimum electrical shape factor, and the parameter ΔImax value corresponds to the maximum electrical shape factor. Since we have fit the distribution of ΔI values to estimate $ΔI_{min}$ and $ΔI_{max}$, there are 2 equations with 2 unknown parameters—meaning one can find a solution. To demonstrate this concept, first take equation (1) and rearrange it such that volume of the protein is a function of the electrical shape factor, symbol, the value of DI, and the dimensions of the nanopore:

$$\Lambda(\Delta I, \gamma(m)) = \frac{\Delta I \rho (l_P + 1.6 r_P)^2}{\gamma(m) V_A}$$

which in turn can be re-written as $$\Delta I(\gamma(m), \Lambda) = \frac{\gamma(m) V_A \Lambda}{\rho (l_P + 1.6 r_P)^2}$$

With this rearranged equation, it follows, with the assumption that $\Delta I_{min}$ is due to the minimum electrical shape factor, that:

$$\Lambda(\Delta I, \gamma) = \frac{\Delta I_{min} \rho (l_P + 1.6 r_P)^2}{\gamma_{min} V_A}$$

and likewise for the ΔImax:

$$\Lambda(\Delta I, \gamma) = \frac{\Delta I_{max} \rho (l_P + 1.6 r_P)^2}{\gamma_{max} V_A}$$

Since $g_{min}$ and $g_{max}$ are only a function of m (Eq. S5-S7) and we have different equations describing them, we have a system with two equations and two unknowns, and thus, we can solve it.

Based on the value of $DI_{max}$ (and the rearranged version of equation 1), the line with the higher peak shows the estimated volume of the protein given the maximum electrical shape factor for a spheroid of various values of m (x-axis). The same goes for the other line, except this time for the minimum electrical shape factor. Since the protein is a constant volume, the solution to the system of equations occurs where the two lines intersect. Hence we know have an estimate of the Volume and Shape.

5. Convert intra-event ΔI(t) signals to angle of the non-spherical particle, θ(t), and solve for rotational diffusion coefficient, DR, and dipole moment, μ.

This step uses the value of m, determined in the previous step from distributions of maximum DI values or it can use the value of m determined by analysis distributions of intra-event DI values from a single protein, to calculate the orientation-dependent electrical shape factor using equations (S4)-(S7); thus γ for the particle can be expressed as γ(θ). The method then uses γ(θ), the volume A of the protein calculated in the previous step, and the quantitative relationship shown in equation (1) to convert intra-event ΔI(t) to θ(t). From the θ(t) signal, mean-squared-angular displacement curves or auto-correlation curves are created in order to apply physical principles for determining DR and μ.

Basically, this step involves using the estimates of the protein's volume and shape to convert the ΔI(t) signal for an event into the angle of a particle as a function of time. We can do this because we know all of the equations (S5-S7) to estimate gII and g☐, and therefore the electrical shape factor as a function of the angle of the particle (equation S4): FIG. 4B plots this particular equation graphically.

$$\gamma(\theta) = \gamma_\perp + (\gamma_\parallel - \gamma_\perp)\cos^2(\theta)$$

Figure 13:
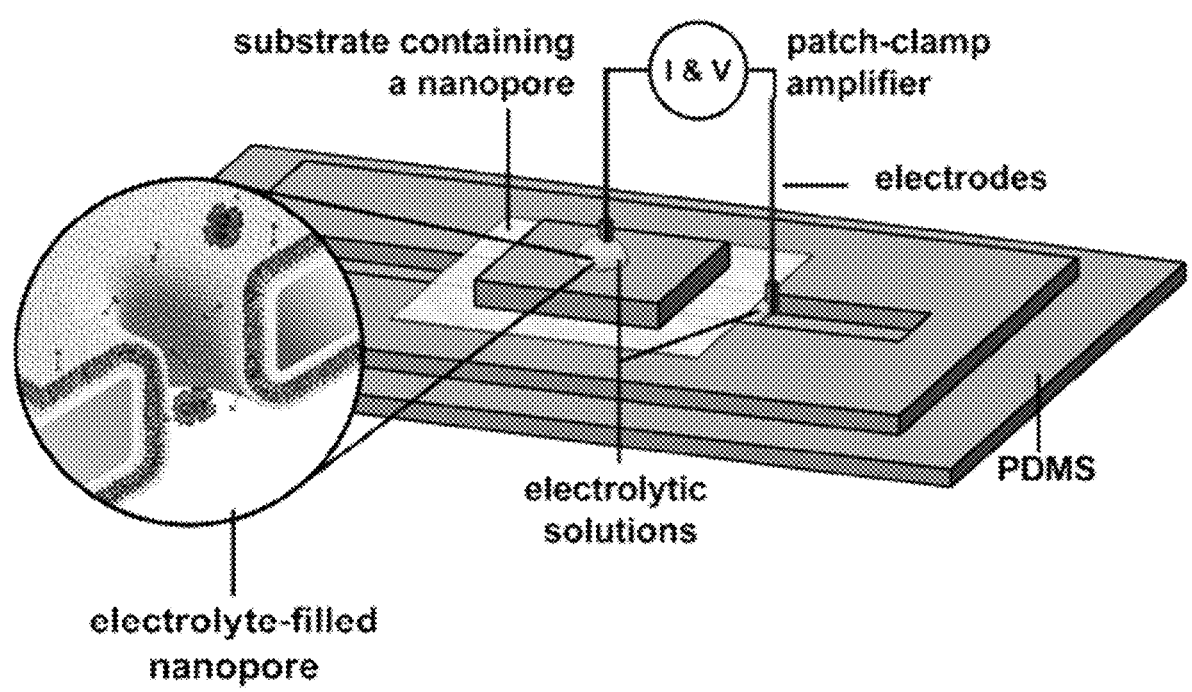
FIG. 13 is a schematic diagram of the experimental setup for recording ion currents through nanopores. Polydimethylsiloxane (PDMS) supports with fluid channels sandwich a silicon chip, thereby creating a single fluidic connection through the nanopore[1-3].

Plugging this equation, γ(θ), into equation 1, and rearranging to solve for theta allows us to convert the electrical signal into an estimate of the particles angle (see FIG. 13).

Figure 12:
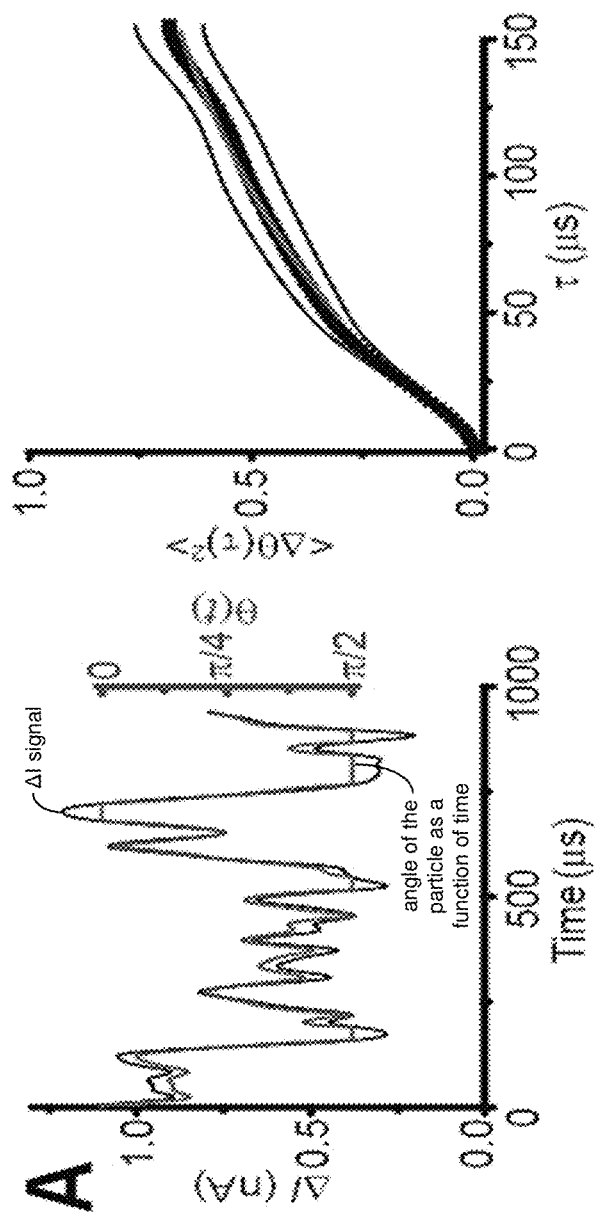

With the angle of the particle as a function of time (lighter line in the left plot of FIGS. 6 and 12; darker line is the ΔI signal) we can then apply physical principles to determine the rotational diffusion coefficient and dipole moment of the protein. In particular, in this case we plotted the mean-squared-angular displacement (left plot)

Steps 3.-4. can be applied to individual resistive pulses if they are sufficiently long to resolve $\Delta I_{min}$ and $\Delta I_{max}$ values. If a resistive pulse is sufficiently long (e.g., ~0.4 ms) we can observe enough ΔI values to construct distributions of the ΔI values from that individual event—from the presence of the ONE protein in the pore. In that case it is conceivable to run the entire data transformation method in the same manner as before. The caveat in this analysis is that the protein must sample a range of orientations such that we estimate $DI_{min}$ and $DIi_{max}$, in order to estimate the proteins volume and shape. FIG. 5 and FIG. 6 show example analyses and events.

Figure 10:
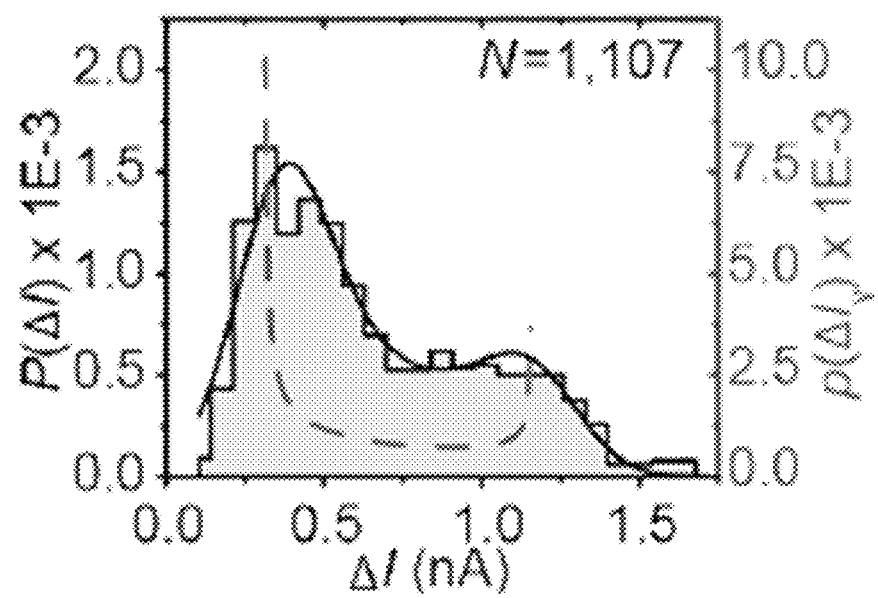
Figure 11:
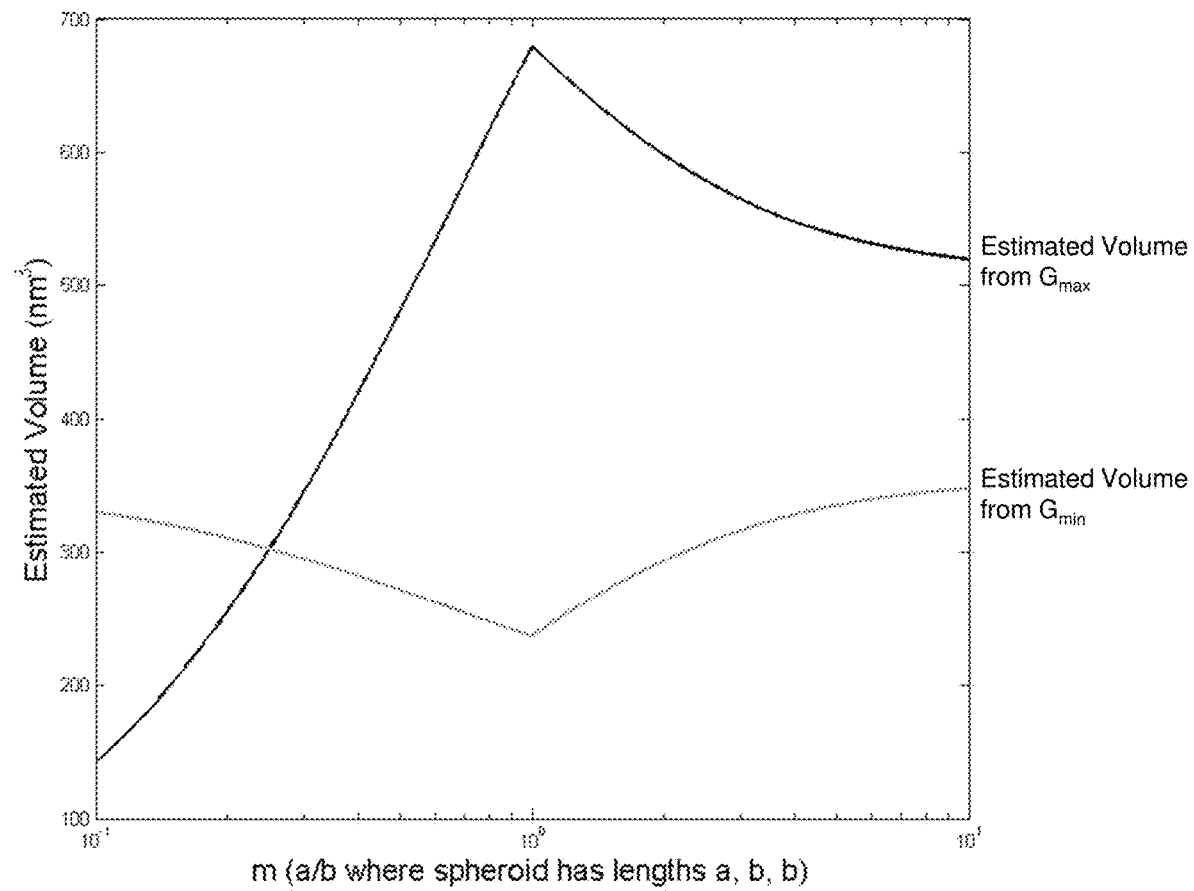

The histogram shows all ΔI values recorded during the event (i.e. between the two dots in the current signal). Note: in the case a decrease in current is upward on the page. So with these events we check whether the distributions are Normal (FIG. 8), fit them with the convolution model to estimate $\Delta I_{min}$ and $\Delta I_{max}$ (FIGS. 9-11), and then determining the shape and volume of that one protein (FIG. 4)—by truly measuring only ONE protein for ~0.5 ms.

That capability opens the door (or at least the possibility) of applying this technique for distinguishing different proteins in a complex mixture of many different proteins—at truly the single protein level. Since we can determine the Size, Volume, Dipole moment, and rotational diffusion coefficient it is basically a 4-Dimensional characterization. (an analogy would be 2D gel electrophoresis which characterize size and isoelectric point).

Supplemental Information Section

Referring to FIG. 13, a nanopore is fabricated in a silicon nitride membrane (inset) that is supported by the silicon chip. Ag/AgCl electrodes in the top solution compartment and bottom solution compartment were used to measure the ionic currents. The electrode connected to the bottom fluidic compartment was connected to ground, and therefore, the polarity of the applied voltage refers to the electric potential in the top fluid compartment relative to the bottom fluid compartment.

S2. Determining the Charge on a Macromolecule

Figure 14:
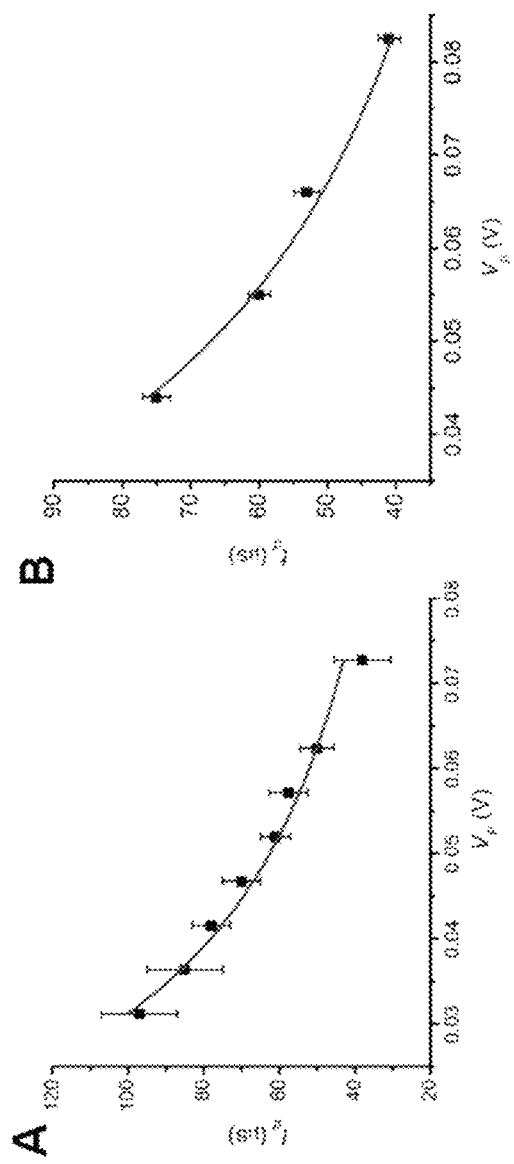
FIG. 14 shows most probable td values for the monoclonal anti-biotin $IgG_1$ antibody (A) and GPI-AchE (B) as a function of the voltage drop, VP, across a bilayer-coated nanopore containing biotin-PE.

Referring to FIG. 14, The inverse relationship between translocation time and electric field across the nanopore (i.e. the applied voltage) provides strong evidence that the lipid-anchored proteins translocate entirely through the nanopore. Moreover, the excellent agreement between theory and experiment further provide evidence that the resistive-pulses observed here and with these applied voltages are due to complete translocation of lipid-anchored proteins. The curve was obtained by a best fit of equation $t_d = l_p^2 k_B T/(|z|eV_p D_L)$ as described in Yusko et al.[4] Briefly, $l_p$ is the length of the nanopore with the bilayer coating, $k_B T$ is the thermal energy (1.38E-23 J K$^{-1}$×295 K), z is the net charge valence of the protein and the only fitting parameter, $V_p$ is the voltage drop across the nanopore, and $D_L$ is the diffusion coefficient of the lipids in the bilayer as determined from FRAP experiments. For the IgG$_1$ antibody (A), the fit returned a value for z of −3.5±0.1 (in 2 M KCl with pH=7.4 in 10 mM HEPES) with $R^2$=0.98, p-value<0.001 (N=8). DL was 1.35E-12 m$^2$ s$^{-1}$ and $l_p$=24 nm. For the GPI-AchE (B), the fit returned a value for z of −2.7±0.1 (in 2 M KCl with pH=6.1 in 10 mM HEPES) with $R^2$=0.99, p-value<0.001 (N=4). For comparison, the theoretical charge of GPI-AchE at zero ionic strength and pH 7.4 is −12 to −16[5,6]. DL was 1.6 E-12 m$^2$ s$^{-1}$ and 1p=24 nm. The bilayer coating in (A) contained 0.15% biotin-PE, 0.8% Rh-PE, and ~99% POPC, and the bilayer coating in (B) contained only 0.8% Rh-PE, and ~99.2% POPC.

S3. Control Experiments Indicate that Broad Distributions of IgG$_1$ Antibodies were not Due to Impurities, Dimers, or Simultaneous Translocations To confirm that the distributions of ΔI values during experiments with monoclonal anti-biotin IgG$_1$ antibodies were not affected by potential impurities in the solution, we performed two control experiments. In one control experiment, we added an excess concentration of soluble biotin to the aqueous solution of an ongoing experiment (FIG. 15A) in order to inhibit competitively the binding of the IgG$_1$ antibodies to the biotin-PE lipids on the surface (FIG. 15B). Fifteen minutes after the addition of the soluble biotin we observed the frequency of resistive pulses decrease from 34 s$^{-1}$ to 1.3 s$^{-1}$. In the second control experiment, we generated a lipid bilayer coated nanopore that did not contain biotin-PE lipids in the coating and therefore was not specific for the translocation of IgG$_1$ antibodies (FIG. 15C). In this experiment, the concentration of the IgG$_1$ antibody was even higher (25 nM compared to 20 nM) than in the original experiment (FIG. 15A), and the frequency of translocation events was 2 s$^{-1}$. Since the frequency of events is proportional to concentration, we estimated that if the concentration of IgG$_1$ in this control experiment was 20 nM, we would expect to observe an event frequency of approximately 1.6 s$^{-1}$. From these two control experiments, we estimated that during experiments with biotin-PE lipids in the bilayer coating only 3.8 to 4.7% of translocation events were due to proteins that were not bound to biotin-PE lipids. Furthermore, almost all of the translocation times calculated from resistive-pulses observed in control experiments (where binding to biotin-PE was not possible) were less than 50 μs, and we did not include resistive-pulses with translocation times less than 50 μs in the analysis of ΔI distributions because the amplitude would be attenuated due to electronic filtering[4,7]. Consequently, we concluded that the protein we detected in the purified solution of anti-biotin IgG$_1$ antibodies was bound to biotin-PE lipids specifically. We also concluded that the resistive-pulses were not due to Fab fragments of the IgG$_1$ in solution because the translocation of Fab Fragments through the same nanopore resulted in resistive pulses with ΔI values less than those observed for the IgG$_1$ antibody (244-325 pA compared to 383-1085 pA, Table S1).

Since IgG antibodies can occasionally form dimers[8], we performed dynamic light scattering (DLS) experiments to characterize the hydrodynamic diameter of the IgG$_1$ antibodies. If dimers of IgG$_1$ antibodies were present in solution and contributing to the bimodal distribution of ΔI values in FIG. 2, we would expect the dimers to be reflected in DLS experiments in a significant fraction because approximately ½ of the resistive pulses had ΔI values within the second bimodal peak of ΔI values. Consequently, if dimers were present, we would expect to observe two peaks in the distributions of estimated hydrodynamic diameters of the particles (in this case proteins) in DLS experiments[8]. FIG. 15D shows that we only observed one peak corresponding to a hydrodynamic diameter of 10.5±2.0 nm. This value is in good agreement with previously published hydrodynamic diameters of IgG antibodies of 10.9-11.0 nm[8,9]. As additional evidence, we added urea to a concentration of 8 M to denature all proteins and disassociate potential aggregates. Again we only observed one peak corresponding to a hydrodynamic diameter of 12.9±2.7 nm (FIG. 15D). This hydrodynamic diameter is slightly larger because of the random-coil and ball-like structure of denatured IgG$_1$ antibodies compared to their native, oblate-shaped structures[8]. These results confirm that dimers of IgG$_1$ antibodies were not responsible for the bimodal distribution of ΔI values.

To rule out the possibility that the widely distributed ΔI values were due to two proteins passing through the nanopore simultaneously, we compared the frequency of translocation events with the translocation times for each protein[10]. In the case of streptavidin translocations, we observed approximately 45 translocation events per second and a most-probable translocation time of about 115 μs. Consequently, on average there was a 0.52% probability of a molecule occupying the nanopore at any time, and the probability of two streptavidin proteins occupying the nanopore at the same time would be 0.003%. In the case of the IgG$_1$ translocation events, the maximum frequency we observed was approximately 30 events per second and a most probable translocation time of about 55 μs. Consequently, on average there was a 0.16% probability of an IgG$_1$ protein occupying the nanopore at any time, and the probability of two IgG$_1$ proteins occupying the nanopore at the same time would then be 0.0027%. Even if the first translocation event of an IgG antibody would be exceptionally long lived (e.g. 1000 μs), the probability of a second antibody to enter the pore during that time would still only be around 3% at an average translocation frequency of 30 Hz. This analysis neglects steric effects, which we expect would be significant given the size of an IgG$_1$ antibody and the dimensions of the nanopores. For GPI-anchored acetylcholinesterase the estimated probability of a two proteins being in the nanopore at the same time was 0.000036% and for Fab fragments it was 0.0016%.

Even during the resistive-pulse sensing experiments with streptavidin in which we estimated the highest probability of observing a protein in the nanopore, we did not observe resistive-pulses with multiple current levels that might suggest the translocation of two proteins simultaneously. Consequently, we conclude that the resistive pulses due to the $IgG_1$, Fab fragments, and GPI-anchored acetylcholinesterase proteins were due to the translocation of one protein at a time.

S4. Events Due to GPI-AchE and $IgG_1$ Antibodies in the Same Nanopore

FIG. 16 shows histograms of the $\Delta I$ values due to the translocation of the $IgG_1$ antibody (150 kDa) and GPI-anchored acetylcholinesterase (160 kDa) through the same nanopore. The experiments were performed using nanopore 3. Though both distributions are bimodal, the relatively narrow distribution of $\Delta I$ values due to GPI-anchored acetylcholinesterase compared to that of the $IgG_1$ antibody confirms that the large molecular weight of the $IgG_1$ antibody was not the reason for broadly distributed $\Delta I$ values. Currents were recorded at an applied potential difference of −0.1 V.

S5. Statistical Comparisons of Empirical and Theoretical Distributions

FIG. 17 shows empirical cumulative distributions (grey curves) of $\Delta I$ values due to the translocation of non-spherical proteins compared to a best-fit Normal distribution (idealized grey curves) and the solution the convolution model, $p(\Delta I)$ (dark curves). In each case, Kolmogorov Smirnov (KS) tests were used to determine if the empirical distribution was different than the Normal distribution and $p(\Delta I)$. Resulting p-values are shown in the FIG. panels. In KS-tests, the null hypothesis is that the two distributions are the same, and therefore, a p-value 0.05 indicates that the difference between two distributions is statistically significant at the $\alpha=0.05$ level. For all of these non-spherical proteins, the distribution of $\Delta I$ values was different from a Normal distribution ($p_N<0.002$). In contrast, the solution to the convolution model, $p(\Delta I)$, described the empirical distributions of $\Delta I$ values well ($p_{p(\Delta I)}>0.31$).

S6. Details Regarding Equation (1)

The relationship between the magnitude of $\Delta I$ and the volume of a particle stems from Maxwell's derivation[11], and it is shown in equation (S1).[12-15]

$$\frac{\Delta I}{I} = -\frac{4\Delta\gamma}{\pi D_P^2(L_P+0.8D_P)}S\left(\frac{d_M}{D_P}\right) \Rightarrow \Delta I = -\frac{\Lambda V_A \gamma}{\rho(L_P+0.8D_P)^2}S\left(\frac{d_M}{D_P}\right) \quad (S1)$$

where $\gamma$ is the electrical shape factor[13,16-20], $\Lambda$ (m³) is the excluded volume of the particle, $L_P$ (m) is the length of the pore, $D_P$ (m) is the diameter of the pore, $\Delta I$ (A) is the magnitude of the change in the current during translocation of a particle, I (A) is the baseline current, $V_A$ (V) is the applied voltage, and p (S2 m) is the resistivity of the electrolyte. $S(d_M/D_P)$ is a correction factor applied when the diameter of the particle, $d_M$, approaches the diameter of the pore, $D_P$, (i.e. $d_M>0.5\ D_P$).[12,13] Under these conditions the electric field in the pore is additionally distorted between the particle and the pore walls resulting in a non-linear increase in the resistance with increasing particle volume.[12,13] Qin et al. recently reviewed these correction factors and showed that the most accurate correction factor for all $d_M/D_P$ ratios was developed by Smythe[21] and Deblois et al.[12], equation (S2):[22]

$$S\left(\frac{d_M}{D_P}\right) = \frac{1}{1-0.8(d_M/D_P)^3}. \quad (S2)$$

Note that in the majority of resistive-pulse sensing literature, particles and proteins have been considered spherical and consequently $\gamma$ was set to a value of 1.5 and was constrained to equal $\frac{1}{6}\pi d_M^3$. Substituting these values into equation (S1) simplifies it to the more commonly seen form in equation (S3):[11,12,14,15,20,22]

$$\frac{\Delta I}{I} = -\frac{d_M^3}{D_P^2(L_P+0.8D_P)}S\left(\frac{d_M}{D_P}\right) \Rightarrow \Delta I = -\frac{\pi V_A d_M^3}{4\rho(L_P+0.8D_P)^2}S\left(\frac{d_M}{D_P}\right), \quad (S3)$$

Since in this work we analyzed resistive-pulses due to the translocation of non-spherical proteins and we expected $d_M$ to be less than ½ $D_P$, we set the correction factor to a value of 1.[4,14,15] We used equation (S1) and expressed the impeded flow of ions through the nanopore during protein translocation events as reductions in current, $\Delta I$.

S7. Electrical Shape Factor and Distributions of Shape Factors

To relate the value of $\Delta I$ to the volume and shape of non-spherical proteins, we considered the possible values of the electrical shape factor, $\gamma$, with the condition that a protein may have an oblate, prolate or spherical shape. Oblates and prolates have an axis of revolution (shown as the dashed line in FIG. 4) with length A and secondary axes with length B. Golibersuch elegantly pointed out that equation (S4) describes the electrical shape factor, $\gamma$, for these ellipsoids as a function of the angle between the axis of symmetry and the electric field, $\theta$, (FIG. 4):[16,23]

$$\gamma(\theta)=\gamma_\perp+(\gamma_\parallel-\gamma_\perp)\cos^2(\theta) \quad (S4)$$

where $\gamma_\parallel$ and $\gamma_\perp$ are the electrical shape factors when the axis of symmetry is parallel to the electric field (i.e. $\theta=0, \pi, \ldots$) and perpendicular to the electric field (i.e. $\theta=\pi/2, 3\pi/2, \ldots$), respectively. Equation S4 implies that the shape factor for any orientation will range between the values of $\gamma_\parallel$ and $\gamma_\perp$. These factors, $\gamma_\parallel$ and $\gamma_\perp$, are related to the well-described depolarization factors for ellipsoids, and, by equation (S5) and are a function of the length to diameter ratio, $m=A/B$, of an ellipsoid.[16,17,24,25]

$$\gamma_\parallel = \frac{1}{1-n_\parallel} \text{ and } \gamma_\perp = \frac{1}{1-n_\perp} = \frac{1}{1-n_\perp} \quad (S5)$$

where for a prolate spheroid with m=A/B>1 is described by equation S6:

$$n_{\|} = \frac{1}{m^2 - 1}\left[\frac{m}{\sqrt{m^2-1}}\ln\left(m + \sqrt{m^2-1}\right) - 1\right] \quad (S6)$$

and for an oblate spheroid with m=A/B<1 is described by equation S7:

$$n_{\|} = \frac{1}{1-m^2}\left[1 - \frac{m}{\sqrt{1-m^2}}\cos^{-1}(m)\right] \quad (S7)$$

and $n_{\perp} = (1-n_{\|})/2$.[16,20,24]

To derive the distribution of shape factors, we considered the simplest scenario that an ellipsoid protein rotates freely around the chemical linker with only one axis of rotation such that, by symmetry, values of θ ranged between 0 and π/2. We also assumed that all angles of θ were equally likely when the maximum ΔI was measured. According to Golibersuch, these assumptions enable using substitution of variables to write a probability distribution function for electrical shape factors P(γ) based on the probability of observing a certain orientation P(θ(γ)), where θ is a function of γ (equation S8):[16]

$$P(\gamma)d\gamma = P[\theta(\gamma)]\frac{d\theta}{d\gamma}d\gamma \quad (S8)$$

Since by symmetry, the value of θ ranges between 0 and π/2 and we assumed that all angles of θ were equally likely, we solved for P(θ) by noting that the integral of a probability distribution function equals 1:

$$\int_0^{\pi/2} P(\theta)d\theta = 1 = \int_0^{\pi/2}\frac{2}{\pi}d\theta \Rightarrow P(\theta)d\theta = \frac{2}{\pi}d\theta \quad (S9)$$

Combining equation (S8) with (S9), we obtained:

$$P(\gamma)d\gamma = \frac{2}{\pi}\left(\frac{d\gamma}{d\theta}\right)^{-1}d\gamma \quad (S10)$$

Differentiating equation (S4) with respect to θ, i.e.

$$\frac{d\gamma}{d\theta},$$

and combining the result with equation (S10), we obtained a probability density function for the possible shape factors [16].

$$P(\gamma)d\gamma = \frac{1}{2\pi[(\gamma - \gamma_{\perp})(\gamma_{\|} - \gamma)]^{1/2}}d\gamma \quad (S11)$$

FIG. 4C of the main text (black line) shows this probability density function (equation S11) is bimodal and symmetric with peaks at $\gamma_{\|}$ and $\gamma_{\perp}$. The bimodal character of this distribution reflects the fact that for small deviations in θ near 0 and near π/2, there is little change in the value of the shape factor compared to deviations in θ around π/4 (FIG. 4B).

Before attempting to describe the non-Normal distributions of ΔI values as a consequence of p(γ), we considered whether the three non-spherical proteins could sample various orientations, and therefore shape factors, in these experiments as well as whether the time-scale of rotation would bias the measurement of maximum ΔI values. We first considered potential steric limitations on the orientations of the proteins in the nanopore. FIG. 1C in the main text shows the expected lipid anchoring locations on spheroids approximately the shape of a Fab fragment, GPI-AchE 26, and an IgG antibody. Since the chemical linker between the lipid head group and the ligand for the IgG1 and Fab fragments was approximately 1.5 nm in length, we expect the anchoring positions shown in FIG. 1C to permit rotation of the proteins in orientations that could generate the minimum and maximum shape factors.

We next examined whether the dipole moment of a protein may align completely in the large electric field in the nanopore (~106 V m-1). Combining the potential energy, ΔU, of a dipole moment in an electric field and the Boltzmann distribution of energies while assuming that the dipole moment was pointed parallel to the longest axis of the protein, we expanded on Golibersuch's probability distribution of shape factors to develop a p(γ) for proteins with dipole moments (FIG. 4C in the main text and Appendix A1). To expand on the theories developed by Golibersuch, we considered the possible probability distribution of shape factors if the orientation of the protein were biased by the electric field in the nanopore. The electric field in the nanopore is on the order of 106 V m-1, and consequently, we expect the orientation of a protein to be biased by alignment of its dipole moment, $\vec{\mu}$ (Debye≈3.33564×10-30 C m), in the electric field, $\vec{E}$ (V m-1).

Taking into account the potential energy of a dipole in an electric field, $\Delta U = \vec{E} \cdot \vec{\mu} = -E\mu\cos(\phi)$, using the Boltzmann distribution of energies, and assuming the dipole was aligned along the symmetry or equatorial axis, we derived equations (S12a) and (S12b), respectively (Supplementary Section S9). Equations (S12a) and (S12b) describe probability distribution functions of shape factors for spheroid proteins when their orientation is biased by the dipole energy in an electric field.

$$P(\gamma)d\gamma = \frac{1}{A}\cosh\left[\frac{E\mu\left(\frac{\gamma - \gamma_{\perp}}{\gamma_{\|} - \gamma_{\perp}}\right)^{1/2}}{k_B T}\right]\left[\frac{1}{\pi[(\gamma - \gamma_{\perp})(\gamma_{\|} - \gamma)]^{1/2}}\right]d\gamma \quad (S12a)$$

$$P(\gamma)d\gamma = \frac{1}{A}\cosh\left[\frac{E\mu\left(\frac{\gamma - \gamma_{\|}}{\gamma_{\perp} - \gamma_{\|}}\right)^{1/2}}{k_B T}\right]\left[\frac{1}{\pi[(\gamma - \gamma_{\perp})(\gamma_{\|} - \gamma)]^{1/2}}\right]d\gamma \quad (S12b)$$

In equation (S12), A is a normalization constant described in Appendix A1. Equation (S12a and S12b) assumes that the dipole moment is either aligned with or perpendicular to the axis of symmetry of the spheroid. FIG. 4C of the main text demonstrates that for spheroid proteins with dipoles of several thousand D, it is theoretically possible to observe a bimodal distribution of shape factors. The average dipole moments of proteins is approximately 550 Debye (http://bioinfo.weizmann.ac.il/dipol/indexj.html), suggesting that many aspherical proteins may generate a skewed bimodal distribution of shape factors. Additional factors may bias the orientation of proteins in the nanopore including steric effects, hydrodynamics, and interactions with the pore wall. All of these factors could affect the estimated value of ΔU or μ in this model. Therefore, an alternative interpretation of these parameters is that they describe the overall bias of the protein's orientation toward θ=0 or π/2. Equations (S12a) and (S12b) cannot describe distributions of ΔI accurately for proteins that are significantly biased (i.e. ΔU>~4 $k_BT$ or μ>~3000 D for a typical pore at 100 mV applied potential) toward intermediate orientations relative to the electric field (i.e. θ=π/4). Under these circumstances, the model would not resolve $\Delta I_{min}$ and $\Delta I_{max}$ accurately, underestimating the shape of the protein (i.e. m would approach 1) and overestimating the volume of the protein. Consequently, equations (S12a) and (S12b) are an approximation of how the orientation, and therefore distribution of shape factors, of a protein with a dipole moment may be biased, and they allow the theoretical distribution of shape factors to become asymmetric.

Finally, we considered whether the proteins would rotate in the pore too quickly to be time resolved or whether their rotation would bias the measurement of ΔI values such that we would only observe ΔI values corresponding to $\gamma_{max}$, and therefore, not resolve ΔI values corresponding to $\gamma_{min}$. Axelrod observed that GPI-AchE has rotational diffusion coefficients, $D_r$, of 10,000±4,000 $rad^2s^{-1}$ and Timbs et al. have observed very reduced mobility (i.e. $D_r$≈0.003 rad2 s-1) of IgG antibodies bound to lipid bilayers 27-29. Consequently, we estimate that the average time for a protein to rotate π/2 radians to be at least 125 μs. Since the majority of the translocation times in these experiments were between 50 and 100 μs (FIG. 14), we expect the majority of ΔI values to reflect a single orientation or a very limited range of orientations of the protein in the nanopore. Consequently, we expect the bimodal distributions of ΔI values observed here to reflect accurately the underlying distribution of shape factors with modes at γmin and γmax[16]. This prediction is supported by our recent discovery of bimodal distributions of ΔI values from translocation of a single, pure protein 4 and subsequent observations made by Raillon et al.[19].

Since the value of ΔI is directly proportional to the electrical shape factor, γ, according to equation (S1), we expressed equations (S12a) and (S12b) in terms of ΔI. For an oblate this procedure results in equations (S13a) and (S13b), where the parameters $\Delta I_{min}$ and $\Delta I_{max}$ correspond to $\gamma_{min}$ and $\gamma_{max}$.

$$P(\Delta I_\gamma)d\Delta I_\gamma = \frac{1}{A}\cosh\left[\frac{E\mu\left(\frac{\Delta I - \Delta I_{max}}{\Delta I_{min}-\Delta I_{max}}\right)^{1/2}}{K_BT}\right]\left[\frac{1}{\pi[(\Delta I - \Delta I_{max})(\Delta I_{min}-\Delta I)]^{1/2}}\right] d\Delta I_\gamma \quad (S13a)$$

and $$P(\Delta I_\gamma)d\Delta I_\gamma = \frac{1}{A}\cosh\left[\frac{E\mu\left(\frac{\Delta I - \Delta I_{min}}{\Delta I_{max}-\Delta I_{min}}\right)^{1/2}}{K_BT}\right]\left[\frac{1}{\pi[(\Delta I - \Delta I_{max})(\Delta I_{min}-\Delta I)]^{1/2}}\right] d\Delta I_\gamma \quad (S13b)$$

Figure 9:
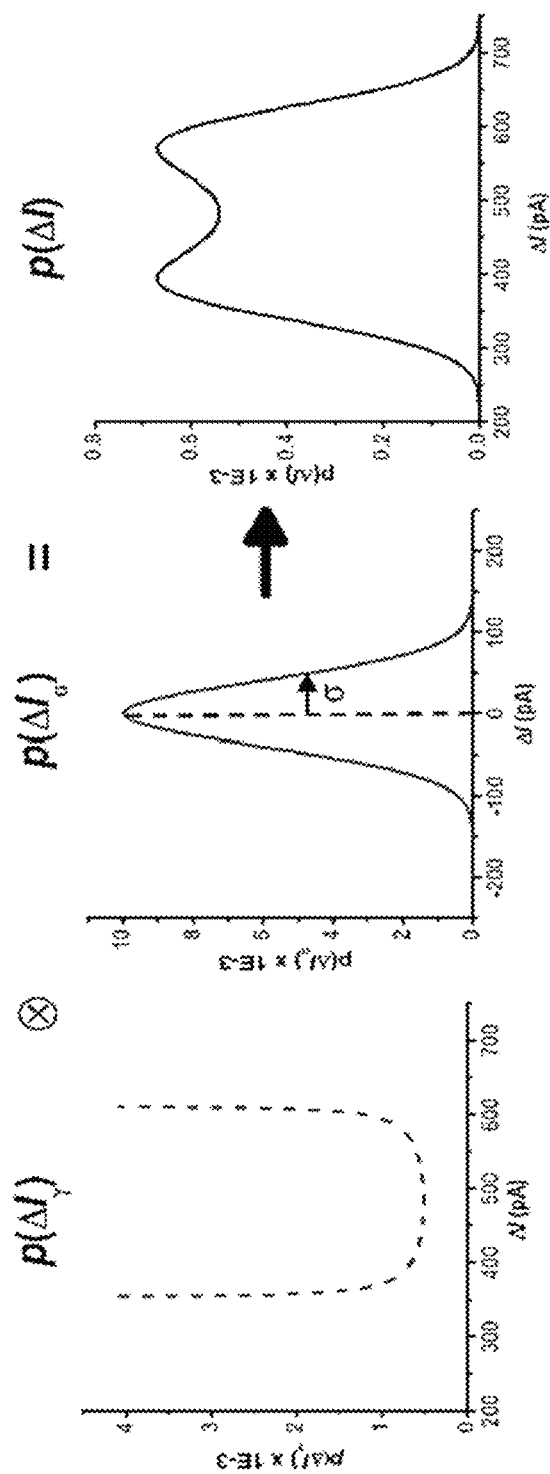

For a prolate, equations (S13a) and (S13b) are interchanged. These probability distributions are the expected distributions of ΔI values due only to the possible values of the shape factor—they do not include effects such as experimental or analytical errors in determining ΔI values. Since the distribution of ΔI values resulting from the distribution of shape factors, $p(\Delta I_\gamma)$, is different depending whether the dipole moment is assumed to be parallel to the symmetry or equatorial axis of the protein (equations (S13a) and (S13b), respectively), we fit each empirical distribution of ΔI values, P(ΔI), with both of the resulting solutions to the convolution model (FIG. 9). Subsequently, we selected the fit that yielded the larger adjusted $R^2$ value as the correct solution. Since the orientation of the dipole moment dictates the preferred orientation of the protein, this procedure effectively determined whether the distribution of ΔI values was skewed towards $\Delta I_{min}$ or $\Delta I_{max}$.

S8. Using ΔImin and ΔImax to Solve for the Volume and Shape of Proteins

Given that the probability distribution of shape factors has modes at $\gamma_\parallel$ and $\gamma_\perp$ corresponding to either $\Delta I_{min}$ or $\Delta I_{max}$ values according to equation (S1), we expected that if the value of $\Delta I_{min}$ and $\Delta I_{max}$ could be determined quantitatively from the empirical distribution of ΔI values then the volume and shape of a protein could also be determined. For example, the minimum shape factor for an oblate spheroid occurs at θ=π/2 and has a value of $\gamma_\perp$ (m) (equation S4). Thus, according to equation (1), the minimum mode in the bimodal ΔI distribution, $\Delta I_{min}$, is a function of Λ and $\gamma_\perp$ (m), and the maximum mode in the bimodal ΔI distribution, $\Delta I_{max}$, is a function of Λ and $\gamma_\parallel$ (m). Since both $\gamma_\parallel$ and $\gamma_\perp$ are solely a function of m, we developed the system of equations (S14) and (S15) in which the values of m and Λ are the only two unknowns and the values of $\Delta I_{min}$ and $\Delta I_{max}$ are determined from fitting the empirical distributions of ΔI with the convolution model. By rearranging equation (S3), we can write for oblate spheroids with m<1:

$$\Lambda(m) = \begin{cases} \Lambda(\gamma_\perp(m), \Delta I_{min}) \\ \Lambda(\gamma_\parallel(m), \Delta I_{max}) \end{cases} \text{if } m < 1, \quad (S14)$$

and for prolate spheroids with m>1:

$$\Lambda(m) = \begin{cases} \Lambda(\gamma_\parallel(m), \Delta I_{min}) \\ \Lambda(\gamma_\perp(m), \Delta I_{max}) \end{cases} \text{if } m > 1. \quad (S15)$$

Since this system of equations has a piecewise dependence on the value of m, we substituted the determined values of $\Delta I_{min}$ and $\Delta I_{max}$ into equations (S14) and (S15) and used MATLAB to solve the system numerically for the excluded volume of the protein, Λ and the value of m.

In FIG. 18, estimating the excluded volume as a function of m using ΔImin and ΔImax values illustrates that there are two solutions to equations (S13) and (S14) for prolate shaped proteins. This FIG. shows this result graphically by plotting the estimated volume of GPI-anchored acetylcholinesterase as a function of m. The two dots indicate the two solutions to the system of equations (m=0.51, Λ=186 $nm^3$ and m=2.9, Λ=216 $nm^3$). In order to simplify the graph, we described the electrical shape factor with the notation $\gamma_{MAX}$ or $\gamma_{MIN}$. We used this notation because for prolates (m>1) $\gamma_{MAX}=\gamma_\perp$ and for oblates (m<1)=$\gamma_{MAX}=\gamma_\parallel$ (see equations S13 and S14). The opposite is true for $\gamma_{Min}$.

Table 1. Values of fitting parameters determined from fitting the convolution model to the empirical distributions of ΔI values as well as the resulting calculations of protein volume, Λ, and shape parameter, m.

TABLE 1

Values of fitting parameters determined from fitting the convolution model to the empirical distributions of ΔI values as well as the resulting calculations of protein volume, Λ, and shape parameter, m.

| Experiment | E† (MV m⁻¹) | $\Delta I_{min}$ (pA) | $\Delta I_{max}$ (pA) | σ (pA) | μ (D) | $R^2$ | Λ* (nm³) | m* |
|---|---|---|---|---|---|---|---|---|
| IgG₁, Pore 1 | −1.5 | 329 | 678 | 58 | 596 | 0.998 | 292 | 0.37 |
| IgG₁, Pore 2 | −1.6 | 258 | 1,320 | 65 | 1,911 | 1.000 | 223 | 0.13 |
| Intra-event (FIG. 4) | −1.6 | 281 | 938 | 48 | 302 | 0.998 | 232 | 0.21 |
| IgG₁, Pore 3 | −0.6 | 164 | 483 | 21 | 2,020 | 0.997 | 319 | 0.24 |
| IgG₁, Pore 8 | −1.4 | 266 | 1,132 | 64 | 1,493 | 0.999 | 217 | 0.16 |
| GPI-AChE, Pore 3 | −1.0 | 280 | 375 | 14 | 3,530 | 0.999 | 278 or 306 | 0.64 or 1.8 |
| GPI-AChE, Pore 5 | −1.3 | 279 | 451 | 40 | 1,712 | 0.999 | 222 or 259 | 0.50 or 3.1 |
| Fab, Pore 6 | −2.1 | 178 | 231 | 11 | 972 | 1.000 | 71 or 77 | 0.67 or 1.6 |
| β-PE, Pore 6 | −0.8 | 181 | 302 | 31 | 2,125 | 0.999 | 192 or 227 | 0.48 or 3.5 |
| G6PDH, Pore 7 | −1.0 | 178 | 264 | 12 | 3,590 | 0.999 | 193 or 220 | 0.56 or 2.3 |
| G6PDH, Pore 12 | −1.1 | 169 | 254 | 58 | 2,822 | 0.997 | 181 or 207 | 0.55 or 2.4 |
| L-LDH, Pore 8 | −0.8 | 195 | 296 | 16 | 2,802 | 0.999 | 267 or 307 | 0.54 or 2.5 |
| BSA, Pore 7 | −1.9 | 165 | 258 | 17 | 1,263 | 0.998 | 91 or 105 | 0.52 or 2.7 |
| BSA, Pore 9 | −1.7 | 165 | 276 | 13 | 2,925 | 0.998 | 110 or 130 | 0.48 or 3.5 |
| α-Amylase, Pore 10 | −1.6 | 157 | 196 | 5 | 1,243 | 1.000 | 92 or 99 | 0.71 or 1.5 |
| BChE, Pore 11 | −1.7 | 150 | 364 | 18 | 1,007 | 1.000 | 82 | 0.30 |

The electric field intensity was calculated according to the following equation: E = $V_A$ * $R_p$/($R_{total}$ * $l_p$), where $R_p$ is the resistance of the pore, $R_{total}$ is the total resistance of the circuit, and $l_p$ is the length of the pore.
*Values of Λ and m shown in bold are those corresponding to the correct shape (i.e. the shape that matches the crystal structure).

For most proteins the value of a determined during the fitting procedure (Table 1) is of a reasonable value given the standard deviation of the baseline noise, which was typically between 30 and 55 pA. Fitting distribution of ΔI values from the IgG1 protein in pore 2 returned quite a large standard deviation compared to the other experiments; however, when we fixed the sigma parameter to the average standard deviation obtained during the other experiments (<σ>=64) and re-ran the fitting procedure, the fit returned similar values of: Λ=302 nm3 and m=0.25. Several factors influence the noise in these experiments, including the stability of the bilayer coating as well as additional noise during individual resistive-pulses due to motion of the protein in the pore. The fact that 4 of the 5 experiments listed in Table 1 have very reasonable values for sigma indicates that this procedure is in general a reasonable method to account for the electrical noise in the system. Furthermore, the excellent agreement between the estimated volume of the proteins and their respective shapes (Table 1 of the main text) provide strong evidence that this procedure enables one to approximate the shape and determine the volume of non-spherical proteins by analyzing the distributions of ΔI values. This method does not assume any information about the protein to extract the parameters shown in Table 1.

S9. Orientation of IgG1 and GPI-AchE can be Biased by the Applied Voltage

The ratio between the number of events with magnitudes near $\Delta I_{max}$ compared to $\Delta I_{min}$ declined exponentially with increasing electric field strength (FIG. 19), suggesting that the potential energy of proteins in the orientation corresponding to $\Delta I_{min}$ was lower than the energy of those in the orientation corresponding to $\Delta I_{max}$. Considering a best-case-scenario where the orientations of the two proteins were biased only due to the energy of a dipole moment in an electric field, we fit these curves with a two-state Boltzmann model and estimated a dipole moment of 996±32 D for the IgG₁ antibody and 360±30 D for GPI-AchE. This simple model assumed that the dipole moment of the proteins was aligned along the longest axis of the protein. Moreover, many factors could bias the alignment of the proteins and the accuracy of these values, however, including alignment of the slender proteins in the electric field gradient prior to entering the nanopore[30,31], entropic barriers affecting orientation inside the nanopore, and dipole moments that are not aligned perpendicular or parallel to the axis of symmetry of these non-spherical proteins.

The empirical probability distributions shown in FIG. 19 were generated by creating a histogram with a bin-width of 1 pA and smoothing the histogram using a moving average (span=75 pA); distributions were then normalized such that the total area under the curves equaled 1. To compare the distributions obtained during different applied voltages, the x-axis was normalized by dividing the ΔI value by the baseline current. The proportion of events in orientation $P_2$ or $P_1$ was determined by taking the area under the curves at $\Delta I_{min}/I_{baseline}\pm 0.025$ and $\Delta I_{max}/I_{baseline}\pm 0.025$, respectively. $\Delta I_{min}$ and $\Delta I_{max}$ for each protein were determined during the fitting procedure described in the main text and FIG. 9. Interestingly, the ratio of events in $P_2$ to $P_1$ ($P_2/P_1$) declines exponentially with increasing voltage, suggesting that the energy of each protein's dipole moment in an electric field biases the orientation of the proteins in the nanopore. Consequently, we fit the ratio $P_2/P_1$ with a two-state Boltzmann model: $P_2/P_1 = e^{-\vec{E}\mu/k_BT}$ where $\vec{E}$ is the electric field (i.e. V/($l_P$+1.6$r_P$)), μ is the dipole moment in Debyes (1 Debye~3.336E-30 C m), and $k_BT$ is the thermal energy (4.11×10⁻²¹ J). This procedure returned estimates of the dipole moments of the proteins of ≈360±30 D for GPI-AchE and ≈996±32 D for the monoclonal IgG₁ antibodies.

S10. Determining the Dipole Moment and Rotational Diffusion Coefficient

In the main text, we plotted the most probable value of the biasing parameter or dipole moment, μ, determined from fitting the convolution model to all intra-event signals longer than 0.4 ms for IgG₁, GPI-AChE, Fab, BSA, and BChE. FIG. 20 shows histograms of the values of μ that were returned from fitting each event in all experiments. In every case, the distribution of µ was described well by a lognormal distribution ($R^2>0.96$); we expected distributions of this shape based on simulations (see Supplementary Section S4). Moreover, the most probable value of µ in each distribution was indicative of the dipole moment of the protein. The dipole moment estimates were in good agreement with measurements from dielectric impedance spectroscopy and calculations from crystal structures returned by the software HydroPro (Table S4). Dielectric impedance spectroscopy was performed as described previously [R. Chari, S. N. Singh, S. Yadav, D. N. Brems, D. S. Kalonia, Determination of the dipole moments of rnase sa wild type and a basic mutant. Proteins: Structure, Function, and Bioinformatics 80, 1041-1052 (2012)] using a buffer of 1 mM KCl and 1 mM HEPES (pH=7.4) for $IgG_1$ and Fab or 1 mM phosphate (pH=5.2) for BSA. Moreover, these results were repeatable between different nanopores; the difference in the estimated dipole moment (i.e. most probable values of µ) from experiments with different nanopores was always less than 20 percent, indicating that pore-dependent effects did not significantly bias the orientation of the protein.

To determine the rotational diffusion coefficient, $D_R$, of a protein during a translocation event, we first fit the convolution model to the intra-event ΔI signal at a bandwidth of 15 kHz to estimate $\Delta I_{min}$ and $\Delta I_{max}$. Using these values, we determined the volume and shape of the protein; this procedure also reveals the maximum and minimum shape factors of the protein based on equations S5-S7. Using these values we calculated θ(t) based on equation (S4). From this trajectory, we calculated the mean-squared-angular displacement (MSAD) of the protein using overlapping time intervals (i.e. 0 to 4 µs, 2 to 6 µs, 4 to 8 µs, etc.). Since θ(t) can be "clipped" (i.e. equation (S4) yields imaginary values of θ(t) for ΔI values that are not between $\Delta I_{min}$ and $\Delta I_{max}$), we only calculated angular displacement between two non-clipped values when computing the MSAD. By symmetry of the spheroid, multiple orientations of the particle are equivalent to θ in the range of 0 to π/2 (for example, the orientation of 3π/2 is equivalent in this equation to the orientation of π/2). This degeneracy in the estimate of θ means that the trajectory of the MSAD will fail to describe the rotation of the protein accurately for long time scales; rather, the trajectory of θ(t) should be used only to estimate changes in θ over short time scales. This degeneracy, combined with the periodicity of rotation, causes the MSAD curve to level off asymptotically (see FIG. 4C in the main text for an example). Hence, we only fit the MSAD curve with a tangent line that passes through the origin to estimate the initial slope of the MSAD curve and reveal the rotational diffusion coefficient, $D_R$. According to the Langevin torque equation, $D_R$ is equal to the initial slope of the MSAD curve divided by 2 for one-dimensional rotation [Z. Cheng, P. M. Chaikin, T. G. Mason, Light streak tracking of optically trapped thin microdisks. Physical Review Letters 89 (2002)]. Since filtering attenuates frequency components of the ΔI signal at which rotation occurs, we calculated $D_R$ at various cut-off frequencies and fit this data with the logistic equation to estimate the value of $D_R$ at infinite bandwidth, which corresponds to the upper horizontal asymptote of the fit (FIG. 21A shows an example). On average, these fits described the experimental data extremely well ($R^2>0.96$). We calculated the overall bandwidth of the signal according to the following equation (101):

$$f_c = \sqrt{1/[1/f_{c1}^2 + 1/f_{c2}^2]}$$

where $f_{c1}$ is the cutoff frequency of the recording electronics (57 kHz) (24) and $f_{c2}$ is the cutoff frequency of the digital Gaussian filter (ranges from 5 to 57 kHz).

FIG. 21 shows histograms of the values of $D_R$ that were returned from fitting all events longer than 0.4 ms for experiments with IgG1, GPI-AChE, Fab, and BChE. We excluded all other experiments from this analysis due to their relatively low signal-to-noise ratios, which yielded values of DR that were erroneously high and similar to values obtained from analyzing signals consisting of only Gaussian noise (~50,000 $rad^2s^{-1}$). As with the distributions of µ, each distribution of DR was described well by a lognormal distribution ($R^2>0.96$), wherein the most probable value was in reasonable agreement with the expected rotational diffusion coefficient for each protein. The rotational diffusion coefficient of the relatively flexible $IgG_1$ antibody was similar in two of the three nanopores; this result suggests that additional pore-dependent effects (e.g. steric effects) not taken into account by this model might impact the rotation of proteins in a nanopore.

S11. Distinguishing an Antigen and Antibody-Antigen Complex in a Single Nanopore Experiment FIG. 23 illustrates the ability of the methods developed in this work to characterize and identify a single protein, exemplified as G6PDH, and a protein-protein complex, exemplified by G6PDH-IgG, in the same solution. FIG. 23A-I shows results from analysis of maximum ΔI values (the procedures for this analysis are described in the figure caption). FIG. 23J-L shows results from analysis of all intra-event ΔI values.

To classify each translocation event as either G6PDH or G6PDH-IgG, we analyzed intra-event ΔI values as described in Section S5 to determine the volume, shape, charge-related $t_d$ value, rotational diffusion coefficient, and dipole moment from each protein or protein complex moving through the nanopore. This procedure identified 787 translocation events that were longer than 400 µs. We normalized the values for each parameter by their standard deviations and classified each event using the clustering algorithm kmeans in MATLAB (16, 45). Briefly, the kmeans clustering algorithm minimizes, across all clusters, the sum of the distance between all points in the cluster to the centroid of the cluster. To assess the quality of all cluster analyses and provide an error for the values assigned to parameters, we ran a bootstrap method in which 1,000 datasets were created by random resampling with replacement of the original dataset (102). We then ran the cluster analysis on these 1,000 datasets. The clustering procedure was always robust with approximately 90% of the data (727 events) consistently being classified as either G6PDH or G6PDH-IgG (at least 95% of the time).

We performed the cluster analysis on several combinations of these five parameters and found that a 3D cluster analysis based on the volume, dipole moment, and rotational diffusion coefficient provided the best separation between clusters as well as the most accurate characterization of the volumes for G6PDH (3% difference) and the G6PDH-IgG complex (7% difference). For instance, FIG. 5C shows that this technique determined a volume for G6PDH of 227±9 $nm^3$ compared to the volume of 220 $nm^3$ determined from distributions of maximum ΔI values in an independent experiment; similarly, this analysis determined the volume of the complex to be 530±64 $nm^3$, and we expected a volume for the complex of 497 $nm^3$ (the volume of G6PDH plus the volume of an IgG protein). The volume of the complex determined from this intra-event analysis was also in excellent agreement with that determined from analysis of distributions of maximum ΔI values, which is shown in FIG. 23I. Furthermore, both the analysis of maximum ΔI values (FIG. 23F) and analysis of intra-event ΔI values followed by cluster analysis revealed that after the addition of anti-G6PDH IgG, the proportion of events due to the G6PDH-IgG complex was between 27 to 28 percent. The agreement between these two values provides additional evidence that the classification of events from single-event analysis was accurate. For reference, two-dimensional projections of the 3D scatter plot are shown in FIG. 23J-L.

Example S11—Cluster Analysis

Prior to this work, the standard practice for distinguishing between proteins in a mixture would have been to analyze scatter plots of td values vs. ΔI values. To illustrate the benefits of the multi-parameter characterization based on methods developed in this work, we performed a two-dimensional cluster analysis on the same data set used above, using only td values and average ΔI values. This analysis found that the protein complex represented only 2.5±0.5% of events, which is ~90% lower than the values determined by single-event analysis or analysis of distributions of maximum ΔI values (FIG. 23). Moreover, this analysis failed to determine the volume of the complex accurately as it returned a value of 833±50 nm3, which is 68% greater than the estimated volume of the complex of 497 nm$^3$ determined from independent experiments.

S12. References for the Supplemental Section

1. Uram, J. D., Ke, K., Hunt, A. J. & Mayer, M. Submicrometer pore-based characterization and quantification of antibody-virus interactions. Small 2, 967-972, (2006).
2. Uram, J. D., Ke, K., Hunt, A. J. & Mayer, M. Label-free affinity assays by rapid detection of immune complexes in submicrometer pores. Angew. Chem.-Int. Edit. 45, 2281-2285, (2006).
3. Yusko, E. C., Billeh, Y. N., Yang, J. & Mayer, M. in Nanopores: Sensing and fundamental biological interactions (eds S. M. Iqbal & R. Bashir) 203-225 (Springer Publishing Co., 2011).
4. Yusko, E. C., Johnson, J. M. et al. Controlling protein translocation through nanopores with bio-inspired fluid walls. Nat. Nanotechnol. 6, 253-260, (2011).
5. Tan, R. C., Truong, T. N., McCammon, J. A. & Sussman, J. L. Acetylcholinesterase: Electrostatic steering increases the rate of ligand binding. Biochemistry 32, 401-403, (1993).
6. Porschke, D., Creminon, C. et al. Electrooptical measurements demonstrate a large permanent dipole moment associated with acetylcholinesterase. Biophys. J. 70, 1603-1608, (1996).
7. Uram, J. D., Ke, K. & Mayer, M. Noise and bandwidth of current recordings from submicrometer pores and nanopores. ACS Nano 2, 857-872, (2008).
8. Bermudez, 0. & Forciniti, D. Aggregation and denaturation of antibodies: A capillary electrophoresis, dynamic light scattering, and aqueous two-phase partitioning study. J. Chromatogr. B 807, 17-24, (2004).
9. Jossang, T., Feder, J. & Rosenqvist, E. Photon-correlation spectroscopy of human-IgG. J. Protein Chem. 7, 165-171, (1988).
10. Skinner, G. M., van den Hout, M., Broekmans, O., Dekker, C. & Dekker, N. H. Distinguishing single- and double-stranded nucleic acid molecules using solid-state nanopores. Nano Lett 9, 2953-2960, (2009).
11. Maxwell, J. C. A treatise on electricity and magnetism. 3rd edn, 435-441 (Clarendon Press, 1904).
12. Deblois, R. W. & Bean, C. P. Counting and sizing of submicron particles by resistive pulse technique. Rev. Sci. Instrum. 41, 909-915, (1970).
13. Grover, N. B., Naaman, J., Ben-sasson, S. & Doljansk, F. Electrical sizing of particles in suspensions. I. Theory. Biophys. J. 9, 1398-1414, (1969).
14. Han, A. P., Creus, M. et al. Label-free detection of single protein molecules and protein-protein interactions using synthetic nanopores. Anal. Chem. 80, 4651-4658, (2008).
15. Ito, T., Sun, L. & Crooks, R. M. Simultaneous determination of the size and surface charge of individual nanoparticles using a carbon nanotube-based Coulter counter. Anal. Chem. 75, 2399-2406, (2003).
16. Golibersuch, D. C. Observation of aspherical particle rotation in Poiseuille flow via the resistance pulse technique. Part 1. Application to human erythrocytes. Biophys. J. 13, 265-280, (1973).
17. Hurley, J. Sizing particles with a Coulter counter. Biophys. J. 10, 74-79, (1970).
18. Soni, G. V. & Dekker, C. Detection of nucleosomal substructures using solid-state nanopores. Nano Lett, (2012).
19. Raillon, C., Cousin, P. et al. Nanopore detection of single molecule RNAP-DNA transcription complex. Nano Lett 12, 1157-1164, (2012).
20. DeBlois, R. W., Uzgiris, E. E., Cluxton, D. H. & Mazzone, H. M. Comparative measurements of size and polydispersity of several insect viruses. Anal. Biochem. 90, 273-288, (1978).
21. Smythe, W. R. Flow around a spheroid in a circular tube. Phys. Fluids 7, 633-638, (1964).
22. Qin, Z. P., Zhe, J. A. & Wang, G. X. Effects of particle's off-axis position, shape, orientation and entry position on resistance changes of micro Coulter counting devices. Meas. Sci. Technol. 22, (2011).
23. Golibersuch, D. C. Observation of aspherical particle rotation in Poiseuille flow via the resistance pulse technique. Part 2. Application to fused sphere dumbbells. J. Appl. Phys. 44, 2580-2584, (1973).
24. Osborn, J. A. Demagnetizing factors of the general ellipsoid. Physical Review 67, 351-357, (1945).
25. Deblois, R. W. & Wesley, R. K. A. Viral sizes, concentrations, and electrophoretic mobilities by nanopar analyzer. Biophys. J. 16, A178-A178, (1976).
26. Goodsell, D. Acetylcholinesterase. June 2004 molecule of the month., <http://www.rcsb.org/pdb/101/motm.do-?momID=54> (2004).
27. Axelrod, D., Koppel, D. E., Schlessinger, J., Elson, E. & Webb, W. W. Mobility measurement by analysis of fluorescence photobleaching recovery kinetics. Biophys. J. 16, 1055-1069, (1976).
28. Yuan, Y. & Axelrod, D. Subnanosecond polarized fluorescence photobleaching—rotational diffusion of acetylcholine-receptors on developing muscle-cells. Biophys. J. 69, 690-700, (1995).
29. Timbs, M. M. & Thompson, N. L. Slow rotational mobilities of antibodies and lipids associated with substrate-supported phospholipid monolayers as measured by polarized fluorescence photobleaching recovery. Biophys. J. 58, 413-428, (1990).

30. Solomentsev, Y. & Anderson, J. L. Electrophoresis of slender particles. J. Fluid Mech. 279, 197-215, (1994).
31. Ai, Y. & Qian, S. Direct numerical simulation of electrokinetic translocation of a cylindrical particle through a nanopore using a poisson-boltzmann approach. Electrophoresis 32, 996-1005, (2011).
32. Cheng, Z., Chaikin, P. M. & Mason, T. G. Light streak tracking of optically trapped thin microdisks. Physical Review Letters 89, (2002).
33. Russel, W. B., Saville, D. A. & Schowalter, W. R. Colloidal dispersions. 65-68 (Cambridge University Press, 1989).
34. Mason, T. G., Gang, H. & Weitz, D. A. Diffusing-wave-spectroscopy measurements of viscoelasticity of complex fluids. J. Opt. Soc. Am. A 14, 139-149, (1997).
35. Janssen, X. J. A., Lipfert, J. et al. Electromagnetic torque tweezers: A versatile approach for measurement of single-molecule twist and torque. Nano Lett 12, 3634-3639, (2012).
36. Li, J., Stein, D. et al. Ion-beam sculpting at nanometre length scales. Nature 412, 166-169, (2001).

What is claimed is:

1. A method of detecting a target biomolecule in a solution comprising a plurality of different biomolecules, the method comprising:
measuring an electrical parameter as a function of time between two liquid compartments separated by and fluidically coupled through a synthetic nanopore upon translocation of individual biomolecules of the plurality of different biomolecules in a plurality of translocation events from one liquid compartment through the synthetic nanopore to the other liquid compartment;
detecting the translocation events by recognizing a change in the electrical parameter relative to a baseline;
collecting values of intra-event values $\Delta I(t)$;
deriving a parameter selected from the group consisting of the volume $\Lambda$, the length to diameter ratio m, the rotational diffusion coefficient DR, and the dipole moment $\mu$ for each individual biomolecule of the plurality from the intra-event values $\Delta I(t)$;
comparing the parameter for each individual biomolecule of the plurality of different biomolecules to a corresponding known parameter for the target biomolecule; and
determining the presence of the target biomolecule in the solution when the parameter for an individual biomolecule of the plurality of different biomolecules matches the corresponding known parameter for the target biomolecule.

2. The method according to claim 1, wherein the target biomolecule is a protein, a peptide oligomer, a nucleic acid, an antibody, a polysaccharide, a virus capsid, a biopolymer, or a protein aggregate.

3. The method according to claim 2, wherein the protein aggregate is an aggregate formed by amyloid beta (A$\beta$) peptides, an immune complex, or a G-protein coupled receptor.

4. The method according to claim 1, wherein the method comprises detecting a plurality of target biomolecules in the solution by:
comparing the parameter for each individual biomolecule of the plurality of different biomolecules to a corresponding known parameter for each target biomolecule; and
individually determining the presence of each target biomolecule in the solution when the parameter for an individual biomolecule of the plurality of different biomolecules matches the corresponding known parameter for each target biomolecule.

5. The method according to claim 1, wherein the electrical parameter is conductivity, resistivity, resistance, conductance, current flow, or voltage.

6. The method according to claim 1, wherein the measuring an electrical parameter as a function of time between the two liquid compartments comprises measuring current flow between the two liquid compartments.

7. The method according to claim 1, wherein the synthetic nanopore is lined with a fluid wall.

8. The method according to claim 7, wherein the fluid wall comprises a ligand that binds to the target biomolecule.

9. The method according to claim 8, wherein the ligand is biotin, cholesterol, sulfonamide, nickel, an antibody, or a protein.

10. The method according to claim 8, wherein the ligand is a protein comprising a thiol group, a maleimide group, or a N-hydroxysuccimide (NHS) ester group, or a group that proceeds through a nitrile group, an acetylene group, or an azide group.

11. The method according to claim 1, further comprising measuring a concentration of the target biomolecule relative to a total biomolecule concentration in the solution.

12. The method according to claim 11, wherein the measuring the concentration the target biomolecule relative to the total biomolecule concentration in the sample is performed by:
deriving the parameter for each individual biomolecule of the plurality of different biomolecules;
obtaining data by classifying each translocation event as translocation of one of the target biomolecules in the sample on the basis of the parameter; and
counting the data to quantify the target biomolecule.

13. A method of deriving an affinity constant K for binding of a first biomolecule to a second biomolecule in a sample comprising the first biomolecule, the second biomolecule, and a complex comprising the first biomolecule and the second biomolecule, the method comprising:
measuring an electrical parameter as a function of time between two liquid compartments separated by and fluidically coupled through a synthetic nanopore upon translocation of individual sample biomolecules in a plurality of translocation events from one liquid compartment through the synthetic nanopore to the other liquid compartment;
detecting the translocation events by recognizing a change in the electrical parameter relative to a baseline;
collecting values of intra-event values $\Delta I(t)$;
deriving a parameter selected from the group consisting of the volume $\Lambda$, the length to diameter ratio m, the rotational diffusion coefficient DR, and the dipole moment $\mu$ for each individual sample biomolecule from the intra-event values $\Delta I(t)$;
comparing the parameter for each individual sample biomolecule to corresponding known parameters for the first biomolecule, the second biomolecule, and the complex;
determining the presence of the first biomolecule, the second biomolecule, and the complex when the parameter for the first biomolecule, the parameter for the second biomolecule, and the parameter for the complex each match to corresponding known parameters for the first biomolecule, the second biomolecule, and the complex;

determining the concentration of each of the first biomolecule ([A]) in the sample, the second biomolecule ([B]) in the sample, and the complex ([AB]) in the sample; and deriving the affinity constant K by calculating K=[A][B]/[AB].

14. The method according to claim 13, wherein the first biomolecule is a protein, the second biomolecule is an antibody, and the complex is a complex between the protein and the antibody.

15. The method according to claim 13, wherein the first biomolecule is a first protein, the second biomolecule is a second protein, and the complex is a protein-protein complex between the first protein and the second protein.

16. The method according to claim 13, wherein the electrical parameter is conductivity, resistivity, resistance, conductance, current flow, or voltage.

17. A method of identifying biomolecules in a sample comprising a plurality of different biomolecules, the method comprising:

measuring an electrical parameter as a function of time between two liquid compartments separated by and fluidically coupled through a synthetic nanopore upon translocation of individual biomolecules of the sample in a plurality of translocation events from one liquid compartment through the synthetic nanopore to the other liquid compartment;

detecting the translocation events by recognizing a change in the electrical parameter relative to a baseline;

collecting values of intra-event values $\Delta I(t)$;

deriving a parameter selected from the group consisting of the volume $\Lambda$, the length to diameter ratio m, the rotational diffusion coefficient DR, and the dipole moment $\mu$ for each individual biomolecule of the plurality from the intra-event values $\Delta I(t)$;

comparing the parameter for each individual biomolecule of the sample to corresponding known parameters for known biomolecules; and identifying individual biomolecules in the sample when the parameter for one of the individual biomolecules of the sample matches one of the known parameters.

18. The method according to claim 17, wherein the plurality of different biomolecules comprises proteins, peptide oligomers, nucleic acids, antibodies, polysaccharides, virus capsids, biopolymers, protein aggregates, or a combination thereof.

19. The method according to claim 17, wherein the protein aggregate is an aggregate formed by amyloid beta (A$\beta$) peptides, an immune complex, or a G-protein coupled receptor.

20. The method according to claim 17, further comprising quantifying the relative number of the biomolecules in the sample by:

carrying out the identifying individual biomolecules in the sample for all translocation events or for a representative sample of translocation events;

obtaining data by classifying each translocation event as translocation of one of the biomolecules in the sample on the basis of the parameters; and counting the data to quantify the biomolecules.

* * * * *

UNITED STATES PATENT AND TRADEMARK OFFICE
CERTIFICATE OF CORRECTION

PATENT NO. : 10,656,117 B2
APPLICATION NO. : 16/436591
DATED : May 19, 2020
INVENTOR(S) : Michael Mayer et al.

It is certified that error appears in the above-identified patent and that said Letters Patent is hereby corrected as shown below:

On the Title Page

(54) and in the Specification, Column 1, Lines 1-4, "NANOPORE-BASED DETERMINATION OF PROTEIN CHARGE, SHARP, VOLUME, ROTATIONAL DIFFUSION COEFFICIENT, AND DIPOLE MOMENT" should be -- NANOPORE-BASED DETERMINATION OF PROTEIN CHARGE, SHAPE, VOLUME, ROTATIONAL DIFFUSION COEFFICIENT, AND DIPOLE MOMENT --

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*